(12) United States Patent
Watanuki et al.

(10) Patent No.: US 7,488,739 B2
(45) Date of Patent: Feb. 10, 2009

(54) QUINOLONE DERIVATIVE OR SALT THEREOF

(75) Inventors: Susumu Watanuki, Chuo-ku (JP); Yuji Koga, Chuo-ku (JP); Hiroyuki Moritomo, Chuo-ku (JP); Issei Tsukamoto, Chuo-ku (JP); Daisuke Kaga, Chuo-ku (JP); Takao Okuda, Chuo-ku (JP); Fukushi Hirayama, Chuo-ku (JP); Yumiko Moritani, Chuo-ku (JP); Jun Takasaki, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 3 days.

(21) Appl. No.: 10/562,128

(22) PCT Filed: Jul. 22, 2004

(86) PCT No.: PCT/JP2004/010781

§ 371 (c)(1),
(2), (4) Date: Dec. 23, 2005

(87) PCT Pub. No.: WO2005/009971

PCT Pub. Date: Feb. 3, 2005

(65) Prior Publication Data

US 2006/0148806 A1    Jul. 6, 2006

(30) Foreign Application Priority Data

Jul. 24, 2003    (JP) .............................. 2003-278852

(51) Int. Cl.
*A61K 31/47* (2006.01)
*C07D 215/233* (2006.01)
*C07D 237/28* (2006.01)
*C07D 407/02* (2006.01)

(52) U.S. Cl. ..................... 514/312; 514/248; 514/300; 546/123; 546/156; 544/235; 544/236

(58) Field of Classification Search ................. 514/248, 514/300, 312; 544/235, 236; 546/123, 156
See application file for complete search history.

(56) References Cited

U.S. PATENT DOCUMENTS

| | | | |
|---|---|---|---|
| 3,943,141 A | 3/1976 | Ellis et al. | |
| 4,024,255 A | 5/1977 | Ellis et al. | |
| 5,024,998 A | 6/1991 | Bodor | |
| 5,106,837 A | 4/1992 | Carson et al. | |
| 5,324,718 A | 6/1994 | Loftsson | |
| 5,506,214 A | 4/1996 | Beutler | |
| 5,648,368 A | 7/1997 | Egbertson et al. | |
| 5,753,666 A | 5/1998 | Beasley et al. | |
| 5,889,009 A * | 3/1999 | Miyake et al. | 514/253.04 |
| 6,121,287 A | 9/2000 | Bjork et al. | |
| 6,130,231 A * | 10/2000 | Wityak et al. | 514/312 |
| 6,136,823 A * | 10/2000 | Sakae et al. | 514/312 |
| 6,248,739 B1 | 6/2001 | Turner et al. | |
| 6,358,976 B1 * | 3/2002 | Wityak et al. | 514/312 |
| 6,458,788 B1 | 10/2002 | Vaillancourt et al. | |
| 6,875,869 B2 | 4/2005 | Jansson | |
| 2002/0025961 A1 | 2/2002 | Scarborough et al. | |
| 2002/0077486 A1 | 6/2002 | Scarborough et al. | |
| 2002/0132806 A1 | 9/2002 | Ruggeri et al. | |
| 2003/0060474 A1 | 3/2003 | Bryant et al. | |
| 2003/0144305 A1 | 7/2003 | Hardern et al. | |
| 2003/0153556 A1 | 8/2003 | Levy et al. | |
| 2003/0162774 A1 | 8/2003 | Scarborough et al. | |
| 2004/0147576 A1 | 7/2004 | Scarborough et al. | |
| 2004/0186131 A1 | 9/2004 | Wathen et al. | |

FOREIGN PATENT DOCUMENTS

| | | |
|---|---|---|
| EP | 0 945 435 A1 | 9/1999 |
| EP | 945435 A1 * | 9/1999 |
| GB | 1433774 A | 4/1976 |
| GB | 2 372 986 A | 9/2002 |
| JP | 50-29574 A | 3/1975 |
| JP | 50-35191 A | 4/1975 |
| JP | 2001-139555 A | 5/2001 |
| JP | 2002-531567 A | 9/2002 |
| WO | WO 97/04779 A1 | 2/1997 |
| WO | WO 98/23592 A1 | 6/1998 |
| WO | WO 99/32450 A1 | 7/1999 |
| WO | WO 00/34283 A1 | 6/2000 |
| WO | WO 00/40561 A1 | 7/2000 |
| WO | WO 00/40563 A1 | 7/2000 |
| WO | WO 01/25239 A2 | 4/2001 |
| WO | WO 01/57037 A1 | 8/2001 |
| WO | WO 02/06513 A2 | 1/2002 |
| WO | WO 02/070487 A1 | 9/2002 |
| WO | WO 02/092571 A1 | 11/2002 |
| WO | WO 02/098856 A2 | 12/2002 |
| WO | WO 03/022214 A2 | 3/2003 |
| WO | WO 2004/019932 A1 | 3/2004 |

OTHER PUBLICATIONS

Losasso et al., J. Chemother. Oct. 1995, 7(5), 420-423.*
Database Chemcats on STN—Accession No. 2003:2205826, Registry No. 375351-23-8 (2003), pp. 1.
Database Chemcats on STN—Accession No. 2002: 163154, Registry No. 375351-23-8 (2002), pp. 1.
International Search Report dated Oct. 26, 2004.
Nancee L. Oien, et al., "Broad-Spectrum Antiherpes Activities of 4-Hydroxyquinoline Carboxamides, a Novel Class of Herpesvirus Polymerase Inhibitors", Antimicrobial Agents and Chemotherapy, 2002, 46(3):724-730.
Indian Office Action issued Feb. 13, 2008 in Patent Application No. 144/DELNP/2006.

* cited by examiner

*Primary Examiner*—Bernard Dentz
*Assistant Examiner*—David E Gallis
(74) *Attorney, Agent, or Firm*—Sughrue Mion, PLLC

(57) ABSTRACT

A platelet aggregation inhibitor comprising a quinolone derivative or a pharmaceutically acceptable salt thereof as an active ingredient, and a novel quinolone derivative or a pharmaceutically acceptable salt thereof useful as a platelet aggregation inhibitor.

14 Claims, No Drawings

QUINOLONE DERIVATIVE OR SALT THEREOF

TECHNICAL FIELD

The present invention relates to a platelet aggregation inhibitor and a P2Y12 inhibitor comprising a quinolone derivative or a pharmaceutically acceptable salt thereof as an active component, and a novel quinolone derivative or a pharmaceutically acceptable salt thereof useful as a pharmaceutical agent, particularly a platelet aggregation inhibitor and a P2Y12 inhibitor.

BACKGROUND OF THE INVENTION

Since platelet was discovered in 1842 by Donne, platelet has been considered as one blood component required for hemostasis for a long time. Presently, it is demonstrated that platelet not only just plays a principle role in the hemostatic mechanism but also exerts multi-functionality for example in the establishment of arteriosclerosis having been drawing clinical attention and the involvement in circulatory diseases including thrombotic diseases, cancer metastasis, inflammations, and post-graft rejections, and additionally in immune reactions.

Generally, therapies for blood reperfusion with pharmaceutical agents or physical methods have been done for thrombotic diseases and ischemic diseases. However, it has been found in recent years that phenomena such as the elevation of platelet activation, adhesion and aggregation occur after blood reperfusion, for example via the rupture of vascular tissues including endothelial cells or the deterioration of the balance between fibrinogenolysis and coagulation with pharmaceutical agents themselves. Clinically, such phenomena have drawn attention. It has also been revealed that after reperfusion is established with thrombolysis using for example t-PA, fibrinolysis potency and coagulation potency are activated, leading to the deterioration of the balance between systemic coagulation and fibrinolysis. Clinically, such phenomena induce re-occlusion and cause serious clinical problems (non-patent reference 1).

Meanwhile, PTCA and stenting have spread rapidly for the therapeutic treatment of diseases based on the constrictions of coronary artery and aorta, including for example angina and myocardial infarction, to give certain fruitful results. However, these therapies disadvantageously damage vascular tissues including endothelial cells, so that acute coronary occlusion and restenosis emerging at chronic stage draw serious concerns. Platelet plays an important role in various thrombotic disorders (re-occlusion and the like) after blood reperfusion therapy. Therefore, anti-platelet agents efficacious in these cases are now desired. However, anti-platelet agents in the related art have not yet been verified to be sufficiently effective.

As the prophylactic or therapeutic agents of these circulatory diseases, platelet aggregation inhibitors such as aspirin, indometacin, cilostazol, prostaglandin $I_2$, prostaglandin $E_1$, ticlopidine, and dipyridamole have been used. Recently, GPIIb/IIIa antagonists inhibiting the final stage of platelet aggregation and having a potent platelet aggregation-inhibiting activity has additionally been developed. The application thereof is however limited to intravenous infusion at the acute stage of thrombosis (non-patent reference 2).

It has been elucidated in recent years concerning ticlopidine for use as an anti-platelet agent that an active metabolite thereof can exert its platelet aggregation-inhibiting action by inhibiting P2Y12 as an ADP receptor. Reports have subsequently been issued, telling triazolo[4,5-D]pyrimidine derivative (patent reference 1) and piperidine and/or homopiperazine (patent reference 2 and patent reference 3) as compounds with the P2Y12-inhibiting action.

Anti-microbial compounds represented by the formula (A) have been known as quinolone derivatives (patent reference 4). However, it has never been known that these derivatives have a platelet aggregation-inhibiting action.

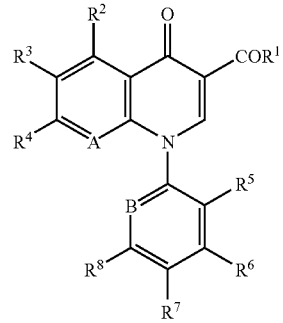

(A)

(See the official gazette of the patent reference 4 about the symbols in the formula.)

[Non-patent reference 1] Journal of the American College of Cardiology, 1988, Vol. 12, p. 616-623

[Non-patent reference 2] General Clinical Practice ("Sogo Rinsho" in Japanese), 2003, Vol. 52, p. 1516-1521

[Patent reference 1] The pamphlet of International Publication WO 00/34283

[Patent reference 2] The pamphlet of International Publication WO 02/098856

[Patent reference 3] The pamphlet of International Publication WO 03/022214

[Patent reference 4] The pamphlet of International Publication WO 98/23592

DISCLOSURE OF THE INVENTION

In such circumstances, it is strongly desired to develop an anti-platelet agent with a high safety profile with a smaller adverse bleeding effect and with distinct pharmaceutical efficacies. Thus, it is an object of the invention to provide a platelet aggregation inhibitor and a P2Y12 inhibitor having a high pharmacological effect and a good balance between the pharmacological effect and the safety profile, and a novel compound useful as a platelet aggregation inhibitor and a P2Y12 inhibitor having a high pharmacological effect and a good balance between the pharmacological effect and the safety profile.

Thus, the invention has been achieved.

The present inventors made investigations so as to overcome the problems. The inventors found that a quinolone derivative represented by the following formula (I) or a pharmaceutically acceptable salt thereof is a compound with a novel skeleton and with an excellent platelet aggregation-inhibiting action and a P2Y12-inhibiting action.

Specifically, the invention relates to a platelet aggregation inhibitor comprising a quinolone derivative represented by the formula (I) or a pharmaceutically acceptable salt thereof as the active ingredient:

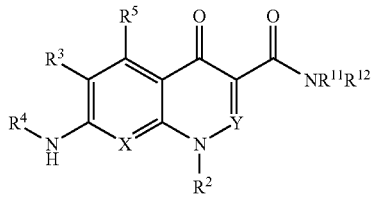

(I)

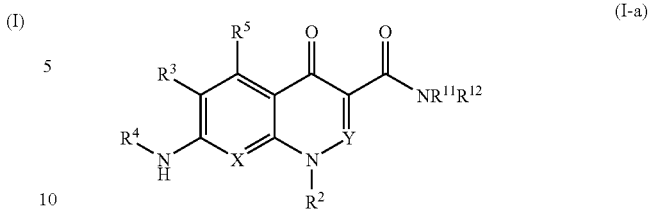

(I-a)

[the symbols in the formula have the following meanings:
X: C—R$^7$ or N;
Y: C—R$^6$ or N;
R$^{11}$: —H, a lower alkyl which may be substituted, or an amino which may be substituted with a lower alkyl which may be substituted;
R$^{12}$: —H, or a lower alkyl or an aryl, which respectively may be substituted, provided that R$^{11}$ and R$^{12}$ together with the adjacent nitrogen may form a cyclic amino which may be substituted;
R$^2$: a lower alkyl, a cycloalkyl, an aryl or hetero-ring, which respectively may be substituted;
R$^3$: a halogen, a lower alkyl or —O-lower alkyl;
R$^4$: a cycloalkyl or a non-aromatic hetero ring, which respectively may be substituted, or a lower alkyl substituted with a cycloalkyl; provided that in case that R$^4$ represents a non-aromatic hetero ring which may be substituted, a carbon atom composing the ring binds to the adjacent NH;
R$^5$: —H, a halogen, cyano, nitro, a lower alkyl, a halogeno-lower alkyl, a cycloalkyl, an aryl, a hetero ring, —O-lower alkyl, —OH, —NHCO-lower alkyl, —N(a lower alkyl)CO-lower alkyl, an amino which may be substituted with a lower alkyl, or a cyclic amino which may be substituted;
R$^6$: —H, a halogen, a lower alkyl or a halogeno-lower alkyl;
R$^7$: —H, a halogen, a lower alkyl or a halogeno-(lower alkyl);
provided that when Y represents C—R$^6$, R$^2$ and R$^6$ together may form a lower alkylene or a lower alkenylene.

In accordance with the invention, the following inventions described in (2) through (21) are provided.

(2) A P2Y12 inhibitor comprising the quinolone derivative of the formula (I) or a pharmaceutically acceptable salt thereof as an active ingredient.

(3) Use of the quinolone derivative of the formula (I) or a pharmaceutically acceptable salt thereof as a platelet aggregation inhibitor.

(4) Use of the quinolone derivative of the formula (I) or a pharmaceutically acceptable salt thereof as a P2Y12 inhibitor.

(5) Use of the quinolone derivative of the formula (I) or a pharmaceutically acceptable salt thereof so as to produce a platelet aggregation inhibitor.

(6) Use of the quinolone derivative of the formula (I) or a pharmaceutically acceptable salt thereof so as to produce a P2Y12 inhibitor.

(7) A novel quinolone derivative represented by the formula (I-a) or a pharmaceutically acceptable salt thereof:

[the symbols in the formula have the following meanings:
X: C—R$^7$ or N;
Y: C—R$^6$ or N;
R$^{11}$: —H, a lower alkyl which may be substituted, or an amino which may be substituted with a lower alkyl which may be substituted;
R$^{12}$: —H, or a lower alkyl or an aryl, which independently may be substituted, provided that R$^{11}$ and R$^{12}$ together with the adjacent nitrogen may form a cyclic amino which may be substituted;
R$^2$: a lower alkyl, a cycloalkyl, an aryl or hetero-ring, which respectively may be substituted;
R$^3$: a halogen, a lower alkyl or —O-lower alkyl;
R$^4$: a cycloalkyl or a non-aromatic hetero ring, which respectively may be substituted, or a lower alkyl substituted with a cycloalkyl; provided that in case that R$^4$ represents a non-aromatic hetero ring which may be substituted, a carbon atom composing the ring binds to the adjacent NH;
R$^5$: —H, a halogen, cyano, nitro, a lower alkyl, a halogeno-lower alkyl, a cycloalkyl, an aryl, a hetero ring, —O-lower alkyl, —OH, —NHCO-lower alkyl, —N-a lower alkyl)CO-lower alkyl, an amino which may be substituted with a lower alkyl, or a cyclic amino which may be substituted;
R$^6$: —H, a halogen, a lower alkyl or a halogeno-lower alkyl;
R$^7$: —H, a halogen, a lower alkyl or a halogeno-(lower alkyl);
provided that when Y represents C—R$^6$, R$^2$ and R$^6$ together may form a lower alkylene or a lower alkenylene and provided that 4-(cyclohexylamino)-1-ethyl-6-fluoro-4-oxo-1,4-dihydroquinoline-3-carbohydrazide is excluded.

(8) The compound described above in (7), where X is CH.
(9) The compound described above in (8), where R$^3$ is a halogen.
(10) The compound described above in (9), where R$^4$ is a cycloalkyl.
(11) The compound described above in (10), where R$^5$ is —H, —OH or a halogen.
(12) The compound described in (11), where R$^{12}$ is a lower alkyl respectively substituted with one or more groups selected from the Group Q (provided that at least one is substituted with a group of the Group P):
Group P: —CO$_2$H, —SO$_3$H, —P(O)(OH)$_2$, and —OP(O)(OH)$_2$; and
Group Q: —F, —OH, —CO$_2$H, —SO$_3$H, —P(O)(OH)$_2$, and —OP(O)(OH)2
(13) The compound described in (11), wherein NR$^{11}$R$^{12}$ together is a cyclic amino group substituted with one or more groups selected from the Group Q (provided that at least one is substituted with a group of the Group P).
(14) The compound described above in (7), which is [2-({[7-(cyclohexylamino)-1-cyclopentyl-6-fluoro-4-oxo-1,4-dihydroquinolin-3-yl]carbonyl}amino)ethyl]phosphonic acid,
(2S)-2-({[7-(cyclohexylamino)-1-cyclopentyl-6-fluoro-4-oxo-1,4-dihydroquinolin-3-yl]carbonyl}amino)butanedioic acid, 2-({[7-(cyclohexylamino)-1-cyclopentyl-6-fluoro-4-oxo-1, 4-dihydroquinolin-3-yl]carbonyl}amino)ethyl dihydrogen phosphate, (2S)-2-({[7-(cyclohexylamino)-1-cyclopentyl-6-fluoro-4-oxo-1,4-dihydroquinolin-3-yl]carbonyl}amino)pentanedioic acid, {2-[({[7-(cyclohexylamino)-6-fluoro-4-oxo-1-[(3S)-tetrahydrofuran-3-yl]-1,4-dihydroquinolin-3-yl}carbonyl)amino]ethyl}phosphonic acid, {2-[({7-(cyclohexylamino)-6-fluoro-4-oxo-1-[(3R)-tetrahydrofuran-3-yl]-1,4-dihydroquinolin-3-yl}carbonyl)amino]ethyl}phosphonic acid,

[2-({[7-(cyclohexylamino)-1-(1-ethylpropyl)-6-fluoro-4-oxo-1,4-dihydroquinolin-3-yl]carbonyl}amino)-1,1-difluoroethyl]phosphonic acid, {2-[({7-(cyclohexylamino)-6-fluoro-1-[2-hydroxy-1-(hydroxymethyl)ethyl]-4-oxo-1,4-dihydroquinolin-3-yl}carbonyl)amino)ethyl}phosphonic acid,

[2-({[7-(cyclohexylamino)-1-ethyl-6-fluoro-4-oxo-1,4-dihydrocinnolin-3-yl]carbonyl}amino)ethyl]phosphonic acid,

[2-({[7-(cyclohexylamino)-1-(1-ethylpropyl)-6-fluoro-4-oxo-1,4-dihydrocinnolin-3-yl]carbonyl}amino)ethyl]phosphonic acid,

[2-({[7-(cyclohexylamino)-1-(1-ethylpropyl)-6-fluoro-4-oxo-1,4-dihydroquinolin-3-yl]carbonyl}amino)ethyl]phosphonic acid, (2S)-2-({[7-(cyclohexylamino)-1-(1-ethylpropyl)-6-fluoro-4-oxo-1,4-dihydroquinolin-3-yl]carbonyl}amino)pentanedioic acid, (2S)-2-({[7-(cyclohexylamino)-1-(1-ethylpropyl)-6-fluoro-4-oxo-1,4-dihydrocinnolin-3-yl]carbonyl}amino)pentanedioic acid or

[2-({[7-(cyclohexylamino)-1-(2,2-dimethyl-1,3-dioxan-5-yl)-6-fluoro-4-oxo-1,4-dihydroquinolin-3-yl]carbonyl}amino)ethyl]phosphonic acid, or a pharmaceutically acceptable salt thereof.

(16) The pharmaceutical composition described above in (15), which is a platelet aggregation inhibitor.

(17) The pharmaceutical composition described above in (15), which is a P2Y12 inhibitor.

(18) Use of the compound described above in any of (7) through (14) as a platelet aggregation inhibitor.

(19) Use of the compound described above in any of (7) through (14) as a P2Y12 inhibitor.

(20) Use of the compound described above in any of (7) through (14) for producing a platelet aggregation inhibitor.

(21) Use of the compound described above in any of (7) through (14) for producing a P2Y12 inhibitor.

Furthermore, the invention relates to a method for therapeutically treating circulatory diseases in close relation with thrombosis via platelet aggregation, including administering an effective amount of the quinolone derivative represented by the formula (I) or a pharmaceutically acceptable salt thereof to a patient.

An active ingredient or compound in accordance with the invention has a quinolone skeleton where the ring atom at position 2 and/or 8 may be substituted with nitrogen atom and may be condensed together between the bonds at positions 1 and 2, and has a characteristic chemical structure in that the quinolone skeleton has an aminocarbonyl substituent at position 3 and an amino group substituent at position 7. Additionally, the compound of the invention has a pharmacologically characteristic feature of platelet aggregation-inhibiting action.

The invention is now described in more detail hereinbelow.

In the present specification, the term "lower" means a linear or branched carbon chain with one to 6 carbon atoms, unless otherwise stated.

Therefore, the term "lower alkyl" means $C_{1-6}$ alkyl and specifically includes for example methyl, ethyl, propyl, butyl, pentyl or hexyl, or structural isomers thereof such as isopropyl or tert-butyl. Preferably, the lower alkyl is $C_{1-5}$ alkyl such as methyl, ethyl, propyl, isopropyl, butyl, isobutyl and 3-pentyl.

The term "lower alkenyl" means $C_{2-6}$ alkyl with one or more double bonds at an appropriate position and specifically includes for example ethenyl, propenyl, butenyl, pentenyl, hexenyl and butadienyl. Preferably, the lower alkenyl is $C_{2-3}$ alkenyl, such as ethenyl, 1-propenyl, 2-propenyl and 3-propenyl.

The term "lower alkynyl" means $C_{2-6}$ alkyl with one or more triple bonds at an appropriate position.

The term "lower alkylene" means a divalent group prepared by eliminating one hydrogen atom at an appropriate position in "lower alkyl" and specifically includes for example methylene, methylmethylene, ethylene, trimethylene, propylene and butylene. Preferably, the lower alkylene is methylene, ethylene and trimethylene.

The term "lower alkenylene" means a divalent group prepared by eliminating one hydrogen atom at an appropriate position in "lower alkenyl" and specifically includes for example vinylene, 1-propenylene, 2-propenylene, 1-butenylene, 2-butenylene, and 3-butenylene. Preferably, the lower alkenylene is vinylene, 1-propenylene and 2-propenylene.

The term "lower alkylidene" means a group with a free atomic valence composing a part of the double bond, as prepared after one hydrogen elimination from a carbon atom with a binding ability in the "lower alkyl".

The term "cycloalkyl" means a monovalent group of non-aromatic $C_{3-8}$ hydrocarbon ring and may form a crosslinked ring or spiro ring or may partially form an unsaturated bond. Specifically, the cycloalkyl includes for example cyclopropyl, cyclobutyl, cyclopentyl, cyclohexyl, cyclooctyl, cyclohexenyl, cyclooctandienyl, adamantyl and norbornyl and preferably includes cyclopentyl or cyclohexyl.

The term "aryl" means a monovalent group of monocyclic to tricyclic aromatic $C_{6-14}$ hydrocarbon ring and specifically includes for example phenyl and naphthyl. Preferably, the aryl is phenyl.

The term "non-aromatic hetero ring" means a monovalent group of a three- to ten-membered ring, preferably a five- to seven-membered ring with hetero atoms such as nitrogen, oxygen and sulfur, which may partially have an unsaturated bond and may be condensed with an aryl or aromatic hetero ring and specifically includes for example pyrrolidinyl, piperidinyl, piperazinyl, azepinyl, morphonyl, thiomorphonyl, pyrazolidinyl, dihydropyrrolyl, tetrahydropyranyl, tetrahydrofuryl, dioxanyl, tetrahydrothiopyranyl, and tetrahydrothienyl. Preferably, the non-aromatic hetero ring is pyrrolidinyl, piperidinyl, piperazinyl, azepinyl, morphonyl, thiomorphonyl, tetrahydropyranyl, dioxanyl and tetrahydrothiopyranyl.

The term "hetero ring" is the generic name of the term "non-aromatic hetero ring" including the term "aromatic hetero ring". The term "aromatic hetero ring" means a monovalent group of an aromatic hetero ring containing one to four aromatic hetero atoms which may be the same or different and is selected from the group of nitrogen, oxygen and sulfur and being satisfactorily condensed with benzene ring and specifically includes for example pyrrolyl, furyl, thienyl, imidazolyl, pyrazolyl, triazolyl, oxazolyl, thiazolyl, furazanyl, pyridyl, pyranyl, thiopyranyl, pyridazinyl, pyrimidinyl, pyrazyl, indolyl, isoindolyl, indolidinyl, benzofuryl, benzothienyl, benzoimidazolyl, indazolyl, benzotriazolyl, benzoxazolyl, benzothiazolyl, benzoxadiazonyl, quinolyl, isoquinolyl, chromenyl, benzothiopyranyl, phthalazinyl, naphthlidinyl, quinoxalinyl, quinazolinyl, cinnolinyl, benzodioxolyl, benzodioxynyl, benzodioxepinyl, and carbazolyl. Nitrogen atom and/or sulfur atom composing these rings may be oxidized. Further, these rings may be partially saturated. Preferably, the monovalent group is pyridyl, furyl, thienyl, indolyl, indazolyl or benzotriazolyl.

The term "halogen" means a monovalent halogen atom group, and specifically includes for example fluoro, chloro, bromo and iodo and preferably includes fluoro and chloro.

The term "halogeno-lower alkyl group" means a group where one or more appropriate hydrogen atoms in the "lower alkyl group" are substituted with one or more of the "halogen" described above and specifically includes for example trifluoromethyl, and trifluoroethyl. Preferably, the halogeno-lower alkyl group is trifluoromethyl.

The term "cyclic amino" is a monovalent group of a hetero ring with a binding hand to nitrogen atom and may satisfactorily contain oxygen and sulfur as hetero atoms. Specifically, the cyclic amino includes pyrrolidino, piperidino, piperazino, homopiperazino, morpholino, thiomorpholino and 3,4-dihydroisoquinolin-2(1H)-yl. Preferably, the cyclic amino is pyrrolidino, piperidino, piperazino, and 3,4-dihydrosioquinolin-2(1H)-yl.

In the specification, the substituents acceptable as those for the phrase "which may be substituted" satisfactorily include those for routine use in the art as substituents for the individual groups. Additionally, one or more substituents which may be the same or different may exist on the individual groups.

The substituents acceptable for the "aryl which may be substituted" in $R^{12}$, the "cyclic amino which may be substituted" as represented by $R^{11}$ and $R^{12}$ together with adjacent nitrogen; the "cycloalkyl which may be substituted", the "aryl which may be substituted", the "non-aromatic hetero ring which may be substituted" and the "aromatic hetero ring which may be substituted" in $R^2$; the "cycloalkyl which may be substituted" and the "non-aromatic hetero ring which may be substituted" in $R^4$; and "the cyclic amino which may be substituted" in $R^5$ include substituents shown below in (a) through (h). Additionally, the substituents acceptable for the "lower alkyl which may be substituted" in $R^{11}$; the "lower alkyl which may be substituted" in $R^{12}$; and the "lower alkyl which may be substituted" and the "lower alkenyl which may be substituted" in $R^2$ include groups shown below in a) through (g). Additionally, $R^z$ represents a lower alkyl which may be substituted with one or more groups selected from the group consisting of —OH, —O-lower alkyls, aminos which may be substituted with one or two lower alkyls, —CO$_2$H, —CO$_2$R$^z$, carbamoyl which may be substituted with one or two lower alkyls, aryls (the aryls may be substituted with halogens), aromatic hetero rings and halogens.

(a) Halogens.
(b) —OH, —O—R$^z$, —O-aryl, —OCO—R$^z$, oxo (=O), —OSO$_3$H, —OP(O)(O—R$^z$)$_2$, —P(O)(O—R$^z$)$_2$, —OP(O)(OH)(O—R$^z$), —P(O)(OH)(O—R$^z$), —OP(O)(OH)$_2$, —P(O)(OH)$_2$.
(c) —SH, —S—R$^z$, —S-aryl, —SO—R$^z$, —SO-aryl, —SO$_2$—R$^z$, —SO$_3$H, —SO$_2$-aryl, sulfamoyl which may be substituted with one or two R$^z$ groups.
(d) Amino which may be substituted with one or two R$^z$ groups, —NHCO—R$^z$, —NHCO-aryl, —NHSO$_2$—R$^z$, —NHSO$_2$-aryl, nitro and imino (=N—R$^z$).
(e) —CHO, —CO—R$^z$, —CO$_2$H, —CO$_2$—R$^z$, carbamoyl which may be substituted with one or two R$^z$ groups or aryls, —CO-non-aromatic hetero ring (the non-aromatic hetero ring may be substituted with —CO$_2$H or —CO$_2$—R$^z$), and cyano.
(f) Aryl or cycloalkyl, provided that the aryl or cycloalkyl may be substituted individually with one or more groups selected from the group consisting of —OH, —O-lower alkyls, aminos which may be substituted with one or two lower alkyls, —CO$_2$H, —CO$_2$R$^z$, carbamoyl which may be substituted with one or two lower alkyls, aryls, aromatic hetero rings, halogens and R$^z$.
(g) Aromatic hetero ring or non-aromatic hetero ring, provided that these groups may be substituted individually with one or more groups selected from the group consisting of —OH, —O-lower alkyls, oxo (=O), aminos which may be substituted with one or two lower alkyls, —CO$_2$H, —CO$_2$R$^z$, carbamoyl which may be substituted with one or two lower alkyls, aryls, aromatic hetero rings, halogens and R$^z$.
(h) Lower alkyl which may be substituted with one or more groups selected from the substituents described above in (a) through (g).

Particularly, individual substituents for the "lower alkyl which may be substituted" and the "aryl which may be substituted" in $R^{12}$, or substituents for —NR$^{11}$R$^{12}$ integrally composing a cyclic amino group are preferably one or more substituents selected from the following Group Q.

Group Q: —F, —OH, —CO$_2$H, —SO$_3$H, —P(O)(OH)$_2$, and —OP(O)(OH)$_2$.

The phrase "amino group which may be substituted with a lower alkyl group which may be substituted" means an amino group substituted with only one "lower alkyl group which may be substituted" or two such "lower alkyl groups". The lower alkyl groups for the di-substitution may be the same or different.

In the compound, X is preferably CH.

Further, Y is preferably CH or N, more preferably CH.

Additionally, $R^{11}$ is preferably —H.

$R^{12}$ is preferably a lower alkyl group or aryl substituted individually with one or more groups selected from the Group Q (provided that at least one is substituted with a group of the Group P); more preferably methyl, ethyl, propyl or butyl substituted individually with one or more groups selected from the Group Q (provided that at least one is substituted with a group of the Group P)

Herein, the Groups P and Q represent the following groups.

Group P: —CO$_2$H, —SO$_3$H, —P(O)(OH)$_2$, and —OP(O)(OH)$_2$; and

Group Q: —F, —OH, —CO$_2$H, —SO$_3$H, —P(O)(OH)$_2$, and —OP(O)(OH)$_2$.

When —NR$^{11}$R$^{12}$ integrally represents a cyclic amino group, it is preferably a cyclic amino group substituted with one or more groups selected from the Group Q (provided that at least one is substituted with a group of the Group P).

Additionally, $R^2$ is preferably a lower alkyl, cycloalkyl or non-aromatic hetero ring, which may be individually substituted.

Further, $R^3$ is preferably a halogen, more preferably fluoro.

Still further, $R^4$ is preferably a cycloalkyl, more preferably cyclohexyl.

Furthermore, $R^5$ is preferably —H, —OH or a halogen, more preferably H, —OH or fluoro, and still more preferably —H or —OH.

And further, $R^6$ is preferably —H.

Still further, $R^7$ is preferably —H.

The quinolone derivative represented by the formula (I) or (I-a) may sometimes form a salt. Such salt is encompassed within an active ingredient of the invention or the compound of the invention, as long as the salt is a pharmaceutically acceptable salt. Specifically, the salt includes salts thereof with inorganic acids such as hydrochloric acid, hydrobromic acid, hydroiodic acid, sulfuric acid, nitric acid, and phosphoric acid; acid addition salts thereof with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, and glutamic acid; addition salts thereof with inorganic bases such as sodium, potassium, calcium and magnesium and organic bases such as methylamine, ethylamine, ethanolamine, lysine and ornithine, and ammonium salts.

An active ingredient or compound of the invention may sometimes include asymmetric carbon atoms, depending on the substituent type. Therefore, optical isomers based on such carbon atom may exist. These optical isomers in mixture or in isolation are all encompassed within the scope of the invention. Additionally, an active ingredient or compound of the invention may sometimes exist in the forms of tautomeric isomers. These isomers in separation or in mixture are also encompassed within the scope of the invention. Additionally, an active ingredient or compound of the invention after labeling, namely an active ingredient or the compound with one or more atoms therein being substituted with a radioisotope or a non-radioactive isotope is also encompassed within the scope of the invention.

Furthermore, various hydrates of an active ingredient or compound of the invention, various solvates thereof and polymorphic substances thereof are also encompassed within the scope of the invention. It is needless to say that an active ingredient or compound of the invention is not limited to the compounds described below in the Examples but includes all derivatives represented by the formula (I) or (I-a) and all pharmaceutically acceptable salts thereof.

Furthermore, the compound of the invention encompasses compounds to be metabolized into an active ingredient or compound of the invention within a living body, namely so-called prodrugs in their entirety. The groups forming the prodrugs of the compound of the invention include the groups described in Prog. Med. 5: 2157-2161 (1985) and the groups described in "The Development of Pharmaceutical Products ("Iyakuhin-no Kaihatsu" in Japanese)", Vol. 7, Molecular Design, pp. 163-198, 1990, Hirokawa Shoten.

(Production Processes)

An active ingredient or compound of the invention can be produced through application of various known synthesis processes by utilizing the characteristic based on the basic skeleton thereof or kinds of the substituents. Representative production processes will be enumerated below. Incidentally, in some case, it is effective on the production technology that depending on the kind of a functional group, the functional group is replaced by a protective group, i.e., a group that can be readily converted into the functional group in a state of the starting material or intermediates. Thereafter, if desired, the protective group is removed, thereby enabling to obtain the desired compound. Examples of such a functional group include a hydroxyl group, a carboxyl group and an amino group. Examples of the protective group thereof include the protective groups as described in Greene and Wuts, Protective Groups in Organic Synthesis (third edition), and these may be properly used depending on the reaction condition.

(First process)

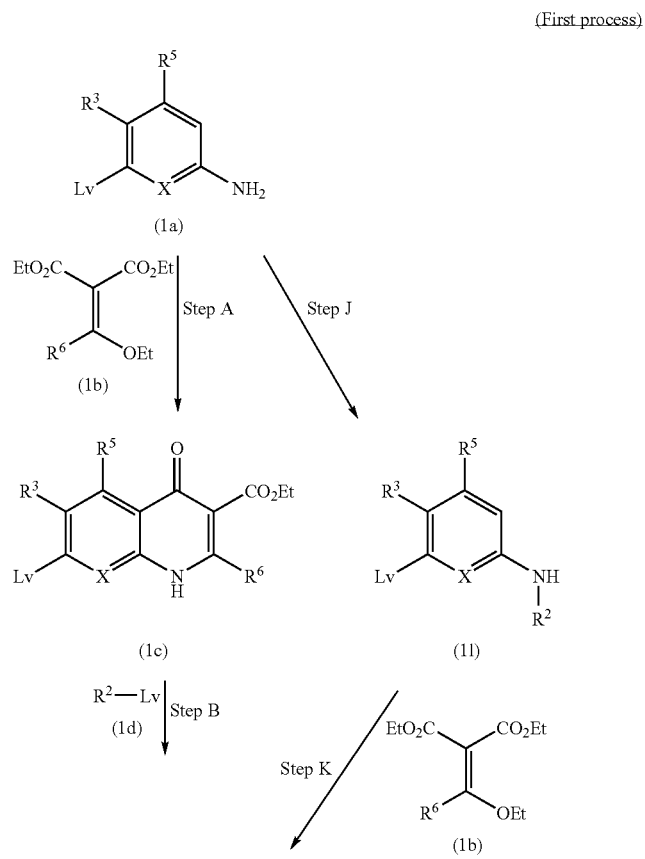

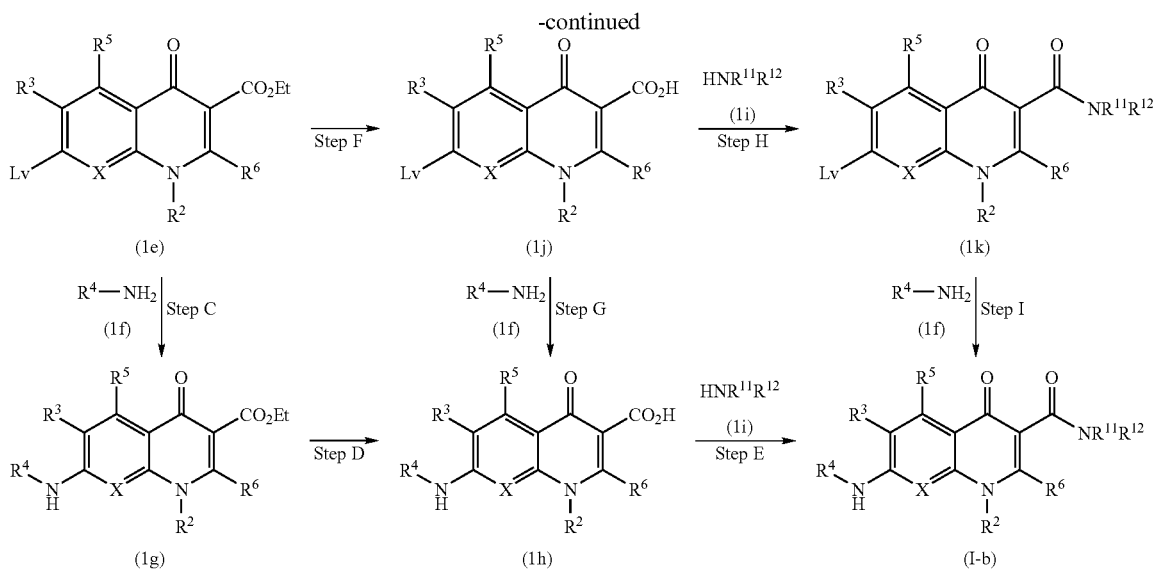

(In the formula, $R^{11}$, $R^{12}$, $R^2$, $R^3$, $R^4$, $R^5$, $R^6$ and X independently represent the aforementioned groups while Lv represents a leaving group, depending on the reaction; the same is true hereinbelow.)

(Step A)

This step is a step of producing a compound (1c) via the condensation and cyclization of the compound (1a) with the compound (1b).

The condensation and cyclization at the step can be carried out in the absence of any solvent or in the presence of a solvent with a high boiling point (for example diphenyl ether is preferably used) under heating and under reflux under heating.

(Step B)

This step is a step of producing a compound (1e) via the alkylation of the compound (1c) with the compound (1d).

The leaving group Lv in the compound (1d) at the step may satisfactorily be any leaving group for routine use in alkylation. As such, halogens such as bromo, iodo and chloro; and sulfonyloxy groups such as methanesulfonyloxy, p-toluenesulfonyloxy, and trifluoromethanesulfonyloxy are preferably used. The method described in J. Med. Chem., 23, 1358-1363, 1980 or a method according to the method can be employed.

(Step C)

The step is a step of producing a compound (1g) by substituting the elimination group in the compound (1e) with the amino group in the compound (1f).

The leaving group Lv in the compound (1e) at the step may be any elimination for routine use in aromatic nucleophilic substitution reaction. As such, preferably, use is made of halogens such as fluoro, chloro and bromo; sulfonyloxy groups such as methanesulfonyloxy, p-toluenesulfonyloxy, and trifluoromethanesulfonyloxy; sulfonyl groups such as lower alkylsulfonyl and arylsulfonyl. In case that sulfonyl is defined as the leaving group Lv at the step C, the compound (1a) with sulfonyl as Lv can be used as the starting material. Otherwise, the compound (1a) with the corresponding sulfanyl as Lv can be used as the starting material. After an appropriate step for example Step B, then, Lv is modified into sulfonyl via an oxidation reaction using for example m-chloroperbenzoic acid, for use in the substitution reaction at the Step C.

The substitution reaction at the step can be carried out in the absence of any solvent or in the presence of solvents inert to the reaction, for example aromatic hydrocarbons such as benzene, toluene and xylene; ethers such as diethyl ether, tetrahydrofuran (THF), and dioxane; halogenated hydrocarbons such as dichloromethane, 1,2-dichloroethane and chloroform; N,N-dimethylformamide (DMF); dimethylsulfoxide (DMSO); esters such as ethyl acetate (EtOAc); acetonitrile; and alcohols such as methanol (MeOH), ethanol (EtOH) and 2-propanol, at ambient temperature and under reflux under heating, using an equimolar amount of the compound (1e) and the compound (1f) or an excess of either one of the compounds. Depending on the compound, the substitution reaction may sometimes be carried out advantageously in the presence of organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used).

(Step D)

The step is a step of producing the compound (1h) by subjecting the compound (1g) to a hydrolysis reaction.

The hydrolysis reaction of the compound (1g) at the step can be carried out in the presence of acids such as inorganic acids for example mineral acids including for example sulfuric acid, hydrochloric acid and hydrobromic acid and organic acids such as formic acid and acetic acid or in the presence of bases such as lithium hydroxide, sodium hydroxide, potassium hydroxide, potassium carbonate, sodium carbonate, cesium carbonate or ammonia, under cooling and under reflux under heating in solvents inert to the reaction, such as aromatic hydrocarbons, ethers, halogenated hydrocarbons, alcohols, DMF, N,N-dimethylacetamide (DMA), N-methylpyrrolidone, DMSO, pyridine and water. The reaction temperature can be selected, appropriately, depending on the compounds and the reaction reagents.

(Step E)

The step is a step of producing the compound (I-b) of the invention via the amidation of the compound (1h) or a reactive derivative thereof with the compound (1i).

For the amidation at this step, amidation for routine use by a person skilled in the art can be employed. Preference is given to a process using condensing agents such as carbonyldiimidazole (CDI), 1-ethyl-3-(3-dimethylaminopropyl) carbodiimide hydrochloride salt (WSC.HCl), dicyclohexylcarbodiimide, diphenylphosphorylazide, and diethylphosphorylcyanide and a process through a mixed acid anhydride, using isobutyl chloroformate and ethyl chloroformate.

Generally, the step is carried out under cooling, under cooling or at ambient temperature, or at ambient temperature and under reflux under heating in solvents inert to the reaction, such as halogenated hydrocarbons, aromatic hydrocarbons, ethers, DMF and DMSO, although the details vary depending on the reactive derivative and the condensing agent to be used.

(Step F)

The step is a step of producing the compound (1j) by subjecting the compound (1e) to a hydrolysis reaction according to the Step D.

(Step G)

The step is a step of producing the compound (1h) by substituting the elimination group in the compound (1j) with the amino group in the compound (1f) according to the Step C.

(Step I)

The step is a step of producing the compound (I-b) of the invention by substituting the elimination group in the compound (1k) with the amino group in the compound (1f) according to the Step C.

(Step J)

The step is a step of producing the compound (1l) via the alkylation of the compound (1a). The alkylation at the step can be carried out by a process according to the Step B or by reductive alkylation. For the reductive alkylation, reductive alkylation processes for routine use by a person skilled in the art can be employed. For example, the method described in "Experimental Lecture Series of Chemistry ("Jikken Kagaku Koza" in Japanese) (the 4th edition)", Japan Chemical Association, Vol. 20, 1992 (Maruzen) is listed. Generally, the step is preferably carried out using reducing agents such as sodium borohydride and sodium triacetoxyborohydride under cooling, at ambient temperature and under reflux under heating in solvents inert to the reaction, such as halogenated hydrocarbons, aromatic hydrocarbons, ethers, alcohols, and acetic acid. Depending on the compound, advantageously, the reaction is carried out in the presence of acids such as mineral acids including for example sulfuric acid, hydrochloric acid and hydrobromic acid and organic acids such as formic acid and acetic acid.

(Step K)

The step is a step of producing the compound (1e) via the condensation and cyclization of the compound (1b) and the compound (1l) according to the Step A.

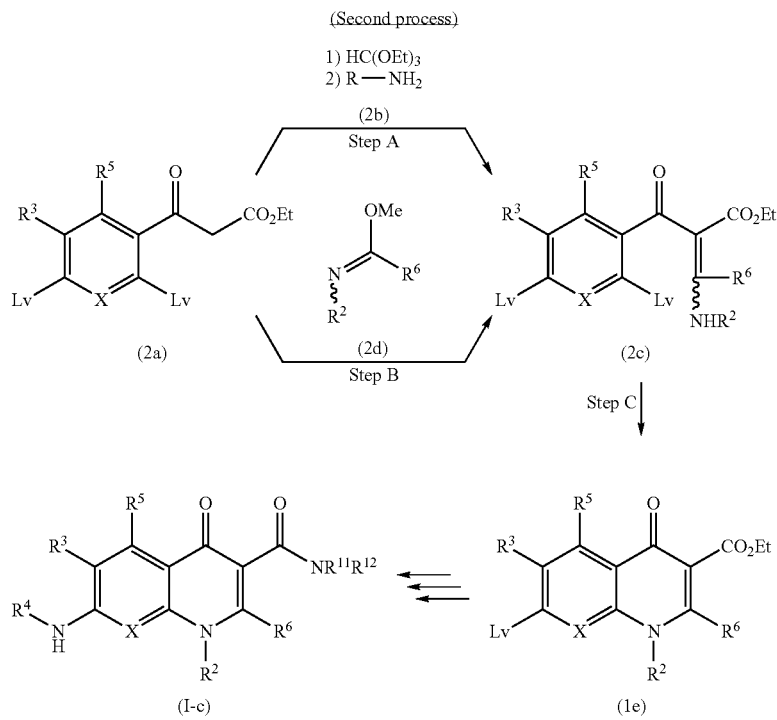

(Step H)

The step is a step of producing the compound (1k) via the amidation of the compound (1j) or a reactive derivative thereof with the compound (1i) according to the Step E.

The present process through the Step A is a production process employable in case that the introduction of $R^2$ involves difficulty in the Step B of the first process, depending on the bulkiness of tert-butyl group, adamantyl group and the like. Additionally, the process through the Step B is a production process employable in case that $R^2$ and $R^6$ together form a ring.

(Step A)

The step is a step of producing the compound (2c) via the condensation of the compound (2a) with orthoformate ester and subsequent addition and elimination with the compound (2b).

The condensation with orthoformate ester at the step can be carried out in a solvent capturing alcohols generated from orthoformate ester such as acetic anhydride, or via the reaction with a reagent capturing alcohols generated from orthoformate ester in a solvent inert to the reaction, such as halogenated hydrocarbons, ethers, aromatic hydrocarbons, DMF, DMSO, esters such as ethyl acetate (EtOAc), and acetonitrile, at ambient temperature and under reflux under heating.

The addition and elimination reaction subsequent to the condensation can be carried out under cooling, at ambient temperature and under reflux under heating in solvents inert to the reaction, such as alcohols, halogenated hydrocarbons, ethers, aromatic hydrocarbons, DMF and DMSO. An excess of the compound (2c) may be used for the reaction. Depending on the compound, advantageously, the step may be carried out in the presence of organic bases (for example triethylamine, diisopropylethylamine, N-methylmorpholine, pyridine, 4-(N,N-dimethylamino)pyridine are preferably used) or bases in the form of metal salts (for example potassium carbonate, cesium carbonate, sodium hydroxide, potassium hydroxide, sodium hydride, and potassium tert-butoxide are preferably used).

(Step B)

The step is a step of producing the compound (2c) via the addition and elimination reaction of the compound (2a) with the compound (2d).

The addition and elimination reaction at the step can be carried out in solvents inert to the reaction, for example halogenated hydrocarbons, ethers, aromatic hydrocarbons, DMF and DMSO, using an equimolar amount of the compound (2a) and the compound (2d) or an excess of either one of the compounds, under cooling, at ambient temperature and under reflux under heating. Depending on the compound, the addition and elimination reaction may sometimes be carried out advantageously in the presence of organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used).

(Step C)

The step is a step of producing the compound (1e) via the intramolecular cyclization of the amino group in the compound (2c).

The addition and elimination reaction of the compound (2c) at this step can be carried out under cooling, at ambient temperature and under reflux under heating in solvents inert to the reaction, such as halogenated hydrocarbons, ethers, aromatic hydrocarbons, DMF, and DMSO. Depending on the compound, the addition and elimination reaction may sometimes be carried out advantageously in the presence of organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used).

The compound (1e) produced at the step is subjected to the process similar to the first process, to produce the inventive compound (I-c).

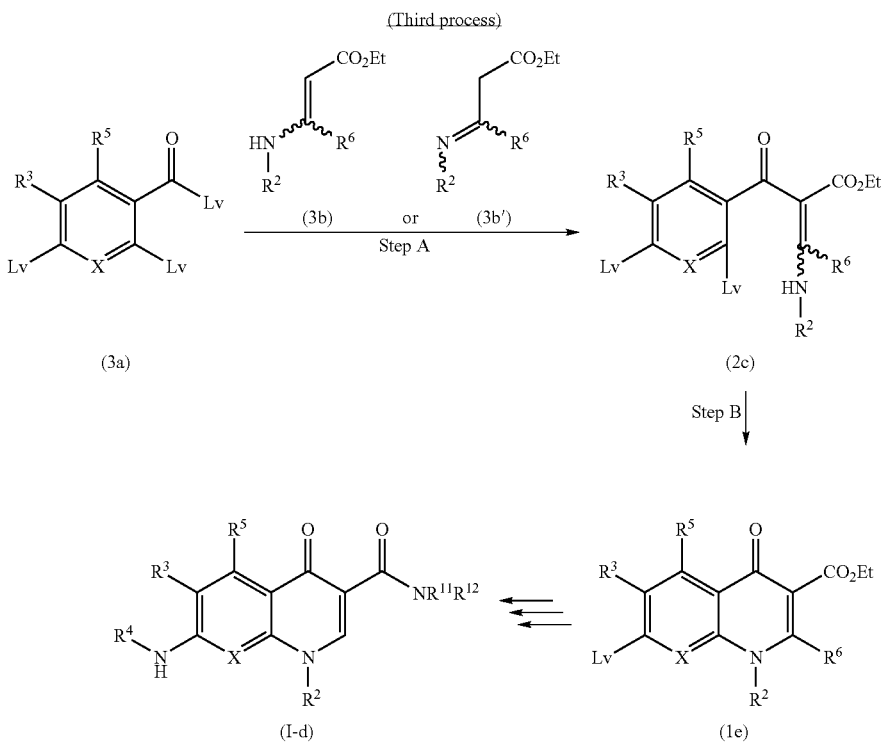

The process is a production process employable in case that $R^2$ and $R^6$ together form a ring.

(Step A)

The step is a step of producing the compound (2c) via the condensation of the compound (3a) with the compound (3b).

As the leaving group Lv in the compound (3a) at the step, halogens such as chloro and bromo, alkoxy, acyloxy and sulfonyloxy such as p-toluenesulfonyl are preferably used. Additionally, the compound (3b') instead of the compound (3b) at the step can be used, where the position of the double bond is isomerized.

The condensation reaction at the step can be carried out in solvents inert to the reaction, for example halogenated hydrocarbons, ethers, aromatic hydrocarbons, DMF and DMSO at ambient temperature and under reflux under heating, using an equimolar amount of the compound (3a) and the compound (3b) or an excess of either one of the compounds. Depending on the compound, the condensation reaction may sometimes be carried out advantageously in the presence of organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used).

(Step B)

The step is a step of producing the compound (1e) via the cyclization reaction of the compound (2c).

The intramolecular cyclization reaction at this step can be carried out according to the step C of the second process. So as to promote the reaction smoothly at this step, the step is advantageously carried out in the presence of bases in the form of metal salts, such as sodium hydride.

Depending on the conditions for the step A, the compound (1e) may instantly be obtained from the compound (3a) without the isolation of the compound (2c).

The compound (1e) produced at the step is subjected to the same process as in the first process, to produce the inventive compound (I-d).

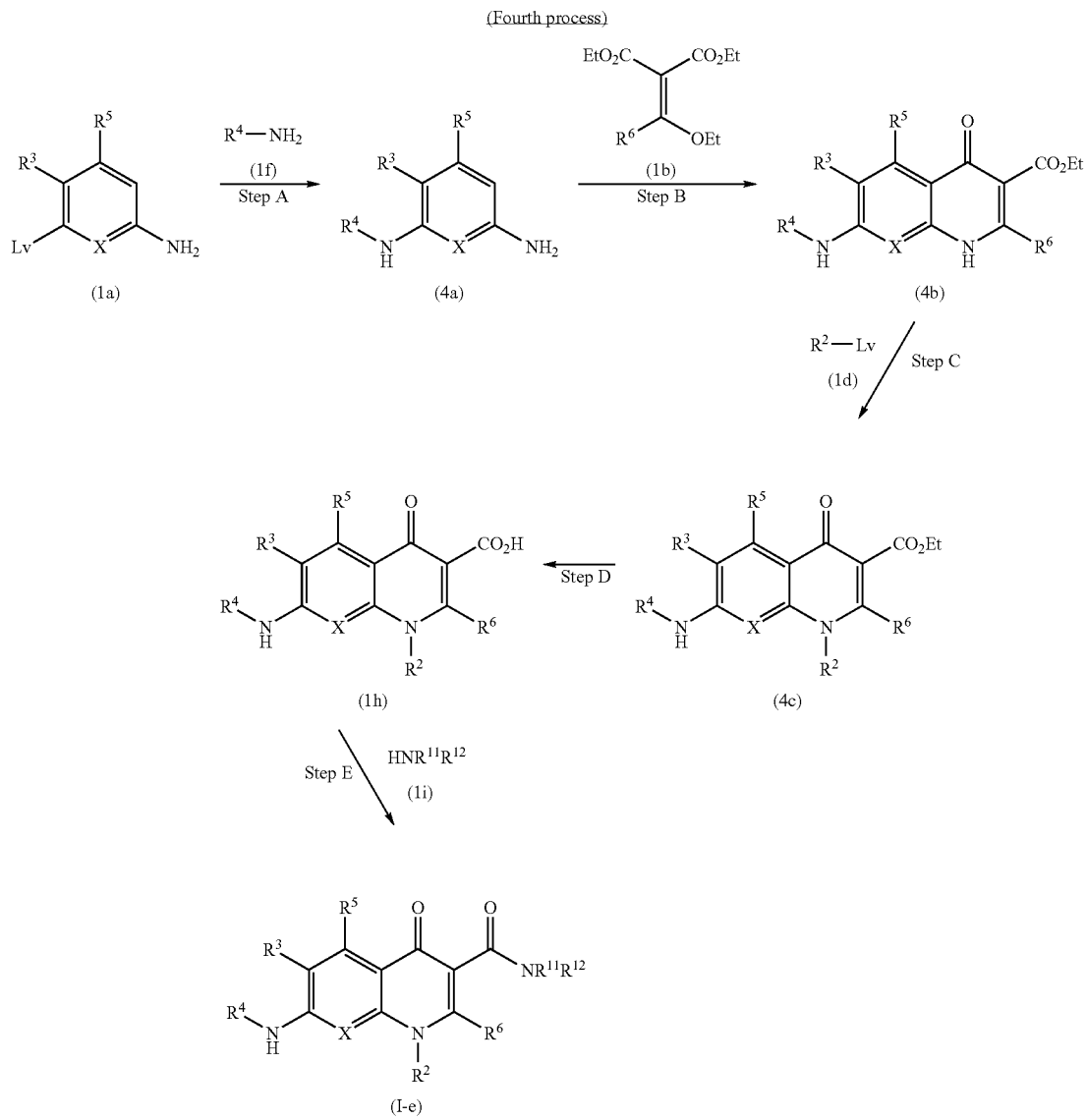

The process is a production process of constructing a fused ring after the preliminary introduction of $R^4NH-$.

(Step A)

The step is a step of producing the compound (4a) by substituting the leaving group in the compound (1a) with the amino group in the compound (1f) according to the step C of the first process.

(Step E)

The step is a step of producing the inventive compound (I-e) via the amidation of the compound (1h) or a reactive derivative thereof with the compound (1i) according to the step E of the first process.

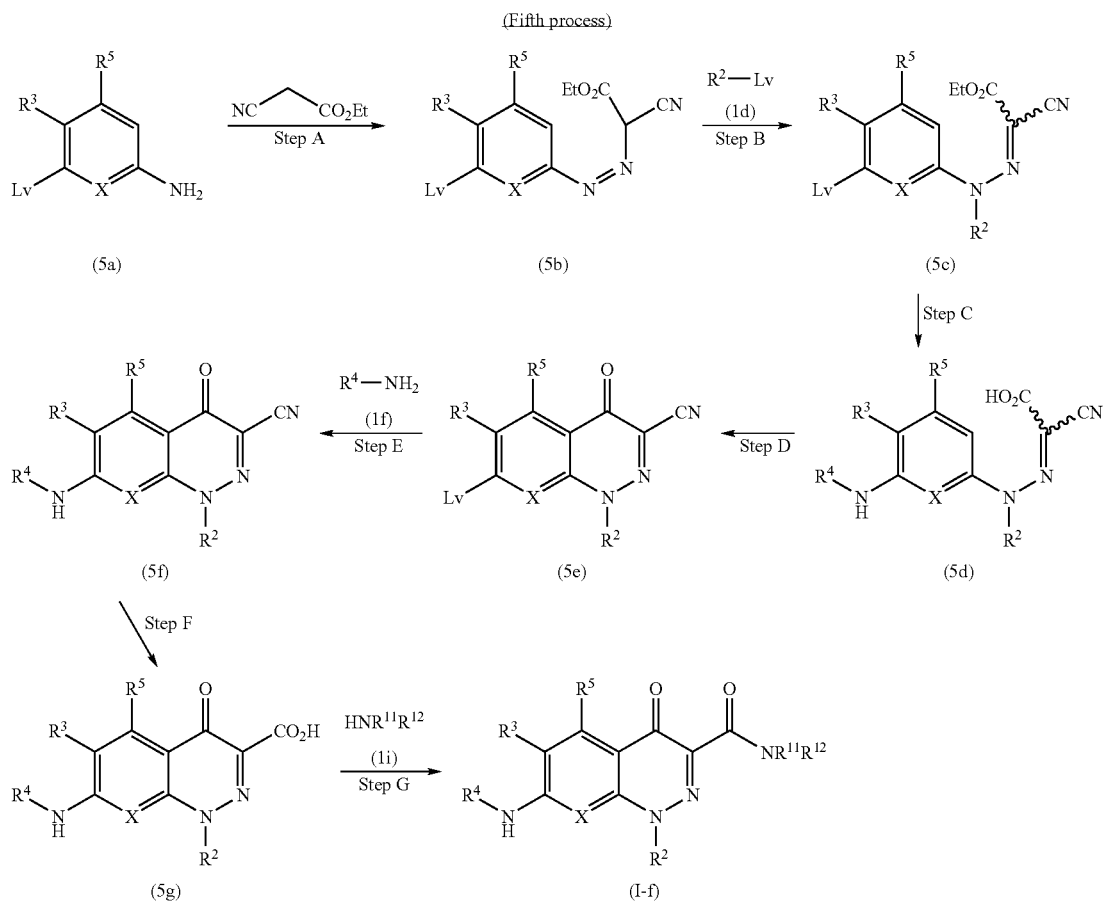

(Fifth process)

Additionally, the step may be carried out via a substitution reaction using a palladium catalyst (in this case, halogens such as bromo and iodo and trifluoromethanesulfonyloxy are preferably used as the Lv in the compound (1a)), according to the method described in Tetrahedron Lett., 38, 6359-6362, 1997 or a process according to the method.

(Step B)

The step is a step of producing the compound (4b) via the condensation and cyclization reaction of the compound (4a) with the compound (1b) according to the step A of the first process.

(Step C)

The step is a step of producing the compound (4c) via the alkylation reaction of the compound (4b) and the compound (1d) according to the step B of the first process.

(Step D)

The step is a step of producing the compound (1h) by subjecting the compound (4c) to a hydrolysis reaction according to the step D of the first process.

The process is a process of producing a compound of the formula (I) or (I-a) where Y is N.

(Step A)

The step is a step of producing the compound (5b) by preparing the compound (5a) into a diazo compound and subsequently adding ethyl cyanoacetate to the resulting diazo compound.

The diazo preparation as the first stage of the step can be carried out in the presence of acids such as hydrochloric acid, sulfuric acid and acetic acid, in solvents inert to the reaction, such as water and alcohol, using an equimolar amount of a reagent for preparing diazo compounds such as sodium nitrite and amyl nitrite and the compound (5a) or an excess of either one of the compounds, under cooling. The addition reaction at the second stage can be carried out in the presence of a base, using an equimolar amount of the diazo compound produced at the first stage and ethyl cyanoacetate or an excess of either one of them under cooling, at ambient temperature and under reflux under heating. As the base, organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used) can be used.

(Step B)

The step is a step of producing the compound (5c) via the alkylation reaction of the compound (5b) and the compound (1d) according to the step B of the first process.

(Step C)

The step is a step of producing the compound (5d) by subjecting the compound (5c) to a hydrolysis reaction according to the step D of the first process.

(Step D)

The step is a step of producing the compound (5e) by subjecting the compound (5d) to acid halogenation and cyclization.

The acid halogenation as the first stage of the step can be carried out in the absence of any solvent or in solvents inert to the reaction, such as aromatic hydrocarbons, ethers, halogenated hydrocarbons, esters such as ethyl acetate, and acetonitrile, using an equimolar amount or an excess of a halogenation agent such as thionyl chloride and oxalyl chloride and the compound (5d) under cooling, at ambient temperature and under reflux under cooling. Depending on the compound, the reaction may sometimes be carried out advantageously by adding a catalytic amount of DMF and the like. The cyclization reaction as the second stage can be carried out by using the acid halide obtained at the first stage and an equimolar amount or an excess of an Lewis acid in the presence of Lewis acids such as aluminum chloride, in the absence of any solvent or in solvents inert to the reaction such as aromatic hydrocarbons, halogenated hydrocarbons, and esters such as ethyl acetate under cooling, at ambient temperature and under reflux under heating.

(Step E)

The step is a step of producing the compound (5f) by substituting the leaving group in the compound (5e) with the amino group in the compound (1f) according to the step C of the first process.

(Step F)

The step is a step of producing the compound (5d) by subjecting the compound (5f) to a hydrolysis reaction according to the step D of the first process.

(Step G)

The step is a step of producing the inventive compound (I-f) via the amidation of the compound (5g) or a reactive derivative thereof and the compound (1i) according to the step E of the first process.

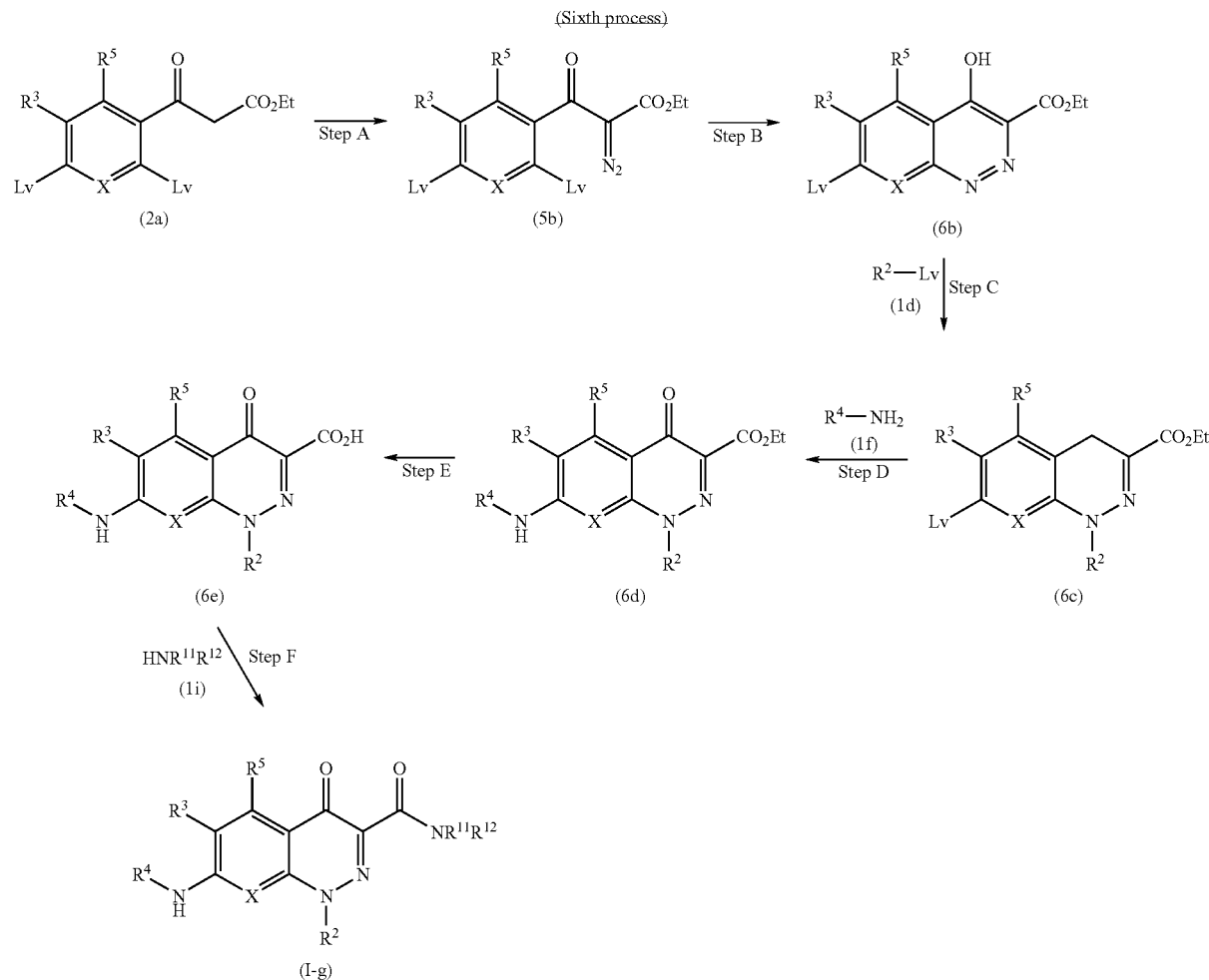

The process is a process of producing the compound of the formula (I) or (I-a) where Y is N.

(Step A)

The step is a step of producing the compound (6a) via the preparation of the compound (2a) into a diazo compound.

The diazo-preparing reaction at this step can be done using an equimolar amount of a diazo-preparing reagent such as sodium azide and p-toluenesulfonyl azide and the compound (2a) or an excess of either one of the compounds in solvents inert to the reaction, for example hydrocarbons such as pentene and hexane, aromatic hydrocarbons, ethers, halogenated hydrocarbons, alcohols, acetonitrile and water, at ambient temperature and under reflux under heating. Depending on the compound, the reaction may sometimes be carried out advantageously in the presence of organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used).

(Step B)

The step is a step of producing the compound (6b) via the reductive intramolecular cyclization reaction of the compound (6a).

At this step, trialkylphosphine or triarylphosphine can be used as the reducing agent. As the leaving group Lv in the compound (6a), for example, halogens such as fluoro, chloro and bromo, sulfonyloxy such as p-toluenesulfonyl and nitro are used. The use of fluoro is particularly preferable. For this step, the method described in Chem. Pharm. Bull., 36, 1321-1327, 1988 or a method according to the method can be employed.

(Step C)

The step is a step of producing the compound (6c) via the alkylation reaction of the compound (6b) and the compound (1d) according to the step B of the first process.

(Step D)

The step is a step of producing the compound (6d) by substituting the leaving group in the compound (6c) with the amino group in the compound (1f) according to the step C of the first process.

(Step E)

The step is a step of producing the compound (6e) by subjecting the compound (6d) to a hydrolysis reaction according to the step D of the first process.

(Step F)

The step is a step of producing the inventive compound (I-g) via the amidation of the compound (6e) or a reactive derivative thereof and the compound (1i) according to the step E of the first process.

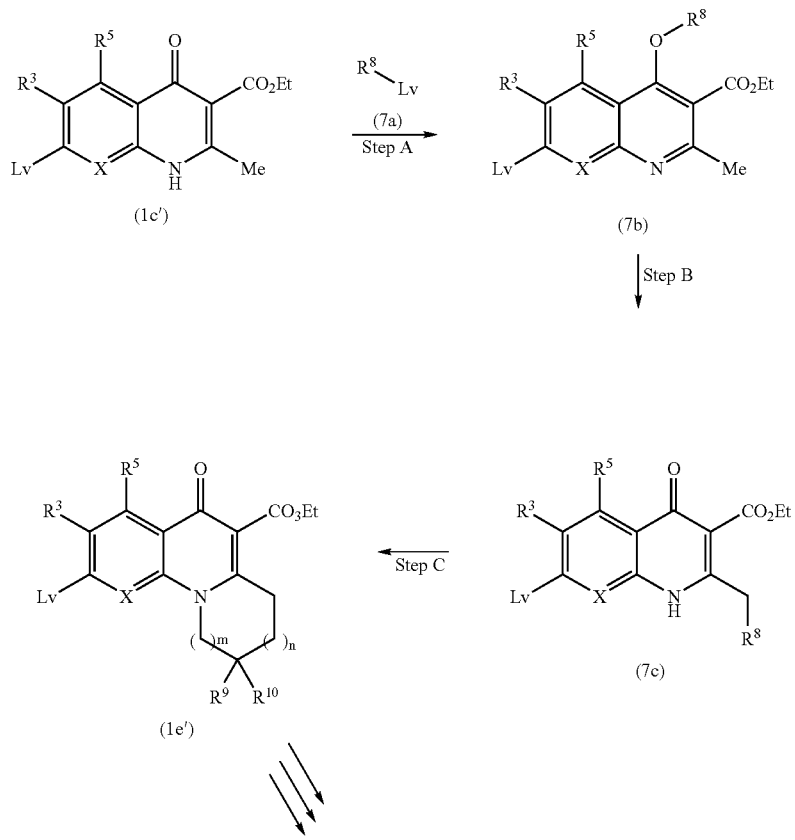

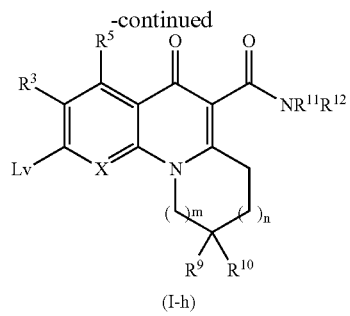

(I-h)

(In the formula, $R^8$ represents a lower alkenyl or a lower alkynyl with an unsaturated bond at position β, such as allyl and propargyl, which may be substituted; $R^9$ and $R^{10}$ represents H or a lower alkyl group; otherwise, $R^9$ and $R^{10}$ together may represent a lower alkylidene; and m and n represent 0 to 3.)

The process is a process of producing the compound of the formula (I) or (I-a), where $R^2$ and $R^6$ together form a ring.

(Step A)

The step is a step of producing the compound (7b) via the alkylation reaction of the compound (1c') and the compound (7a).

The alkylation reaction at this step can be done, using an equimolar amount of the compound (1c') and the compound (7a) or an excess of either one of the compounds in the absence of any solvent or in solvents inert to the reaction, for example aromatic hydrocarbons, ethers, halogenated hydrocarbons, DMF, DMSO, esters such as ethyl acetate, and acetonitrile or in solvents such as alcohol, at ambient temperature and under reflux under heating. Depending on the compound, the substitution reaction may sometimes be carried out advantageously in the presence of organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used).

(Step B)

The step is a step of producing the compound (7c) via the intramolecular rearrangement reaction of the compound (7b).

The cyclization reaction at this step can be done in the absence of any solvent or in the presence of a solvent with a high boiling point (for example 1,2-dichlorobenzene is preferably used) under heating and under reflux under heating.

(Step C)

The step is a step of producing the inventive compound (1e') via the intramolecular cyclization reaction of the compound (7c) in case that $R^8$ has an leaving group such as halogens (chloro and bromo are preferably used) and sulfonyloxy (methanesulfonyloxy and p-toluenesulfonyloxy are preferably used) or a triple bond.

The intramolecular cyclization reaction of the compound (7c) at this step can be done in the absence of any solvent or in solvents inert to the reaction, such as halogenated hydrocarbons, ethers, aromatic hydrocarbons, DMF and DMSO, under cooling, at ambient temperature and under reflux under heating. Depending on the compound, the reaction may sometimes be carried out advantageously in the presence of organic bases (for example triethylamine, diisopropylethylamine, N-methylmorpholine, pyridine, 4-(N,N-dimethylamino)pyridine are preferably used), or bases in the form of metal salts (potassium carbonate, cesium carbonate, sodium hydroxide, potassium hydroxide, sodium hydride, potassium tert-butoxide are preferably used).

Depending on the conditions for the step B, further, the compound (1e') may sometimes be obtained instantly from the compound (7b) without isolation of the compound (7c).

The compound (1e') produced at the step is subjected to the same process as the first process, to produce the inventive compound (I-h).

Additionally, some compounds represented by the formula (I) or (I-a) may also be produced from the inventive compounds thus obtained by an appropriate combination of known steps for routine use by a person skilled in the art, such as alkylation, acylation, substitution, oxidation, reduction and hydrolysis.

The inventive compounds thus produced are isolated and purified as they are free or are isolated and purified as salts prepared by general methods. The isolation and purification are done by general chemical procedures such as extraction, concentration, distillation, crystallization, filtration, recrystallization, and various chromatographic means.

Various isomers can be isolated by general methods, utilizing the difference in physico-chemical properties between the isomers. For example, a racemic mixture can be prepared into an optically pure isomer by a general racemic resolution method including for example preparing a diastereomer salt with a general optically active acid such as tartaric acid and subsequent optical resolution. Additionally, a diastereomer mixture can be separated for example by fractional crystallization or various chromatographic means. Still further, optically active compounds can be produced by using appropriate optically active starting materials.

INDUSTRIAL APPLICABILITY

An active ingredient or compound of the invention has an excellent platelet aggregation-inhibiting action and an excellent P2Y12-inhibiting action. Therefore, an active ingredient or compound of the invention is useful as a pharmaceutical agent, particularly a platelet aggregation inhibitor and a P2Y12 inhibitor. Accordingly, an active ingredient or compound of the invention is useful as a prophylactic and/or therapeutic agent of circulatory diseases in close relation with thrombosis via platelet aggregation, including ischemic disorders for example unstable angina, acute myocardial infarction and secondary onsets thereof, re-occlusion and re-stenosis post-liver artery bypass surgery, post-PTCA or post-stenting, thrombolytic promotion of liver artery and prophylaxis of re-occlusion; cerebral vascular disorders such as transient cerebral ischemia attack (TIA), cerebral stenosis, and subarachnoid hemorrhage (vascular constriction): and peripheral artery diseases such as chronic artery occlusion; as well as an aiding agent during heart surgery or vascular surgery.

The excellent platelet aggregation-inhibiting action of the inventive compound was verified by the following test methods.

(1) Test for Assaying Human Platelet Aggregation-inhibiting Activity

Blood was withdrawn from healthy human volunteers (adult males), in the presence of a ¹/₁₀th volume of sodium citrate, and centrifuged-to obtain supernatant platelet-enriched plasma (PRP). The platelet count in PRP was determined with an automatic blood cell counter (MEK-6258; manufactured by NIHON KOHDEN CORPORATION). Then, the platelet count in PRP was adjusted to $3 \times 10^8$/ml with platelet-poor plasma. ADP as a platelet aggregation-inducing agent was a product of MCMEDICAL, Inc. Platelet aggregation was measured using an aggregometer (MCM Hematracer 212; MCMEDICAL, Inc.). Specifically, 80 µl of PRP and 10 µl of a solution of an active ingredient or compound of the invention or a solvent (10% DMSO) were incubated together at 37° C. for one minute, to which 10 µl of ADP (50 µM) was added to induce platelet aggregation. Then, the change of the transmitting light was recorded over 5 minutes. Using the area-under-the curve of platelet aggregation as an indicator, the inhibition ratio was calculated. The results from an active ingredient or compound of the invention at 10 µM (as final concentration) are shown in Table 1.

TABLE 1

Human platelet aggregation-inhibiting action

| Test compound | % inhibition |
| --- | --- |
| Example 18 | 92 |
| Example 419 | 88 |
| Example 429 | 88 |
| Example 522 | 86 |
| Example 557 | 81 |
| Example 583 | 92 |
| Example 603 | 81 |
| Example 619 | 91 |

(2) Substitution Test of the Binding Between Human P2Y12 and 2-methylthio-ADP (2-MeS-ADP)

After C6-15 cells were inoculated on a DMEM culture medium to $1 \times 10^6$ cells in a 10-cm petri dish for culturing for one day, where 8 µg of a plasmid pEF-BOS-dhfr-human P2Y12 and 0.8 µg of pEF-BOS-neo (Nucleic Acid Res., 18,5322, 1990) were genetically introduced with a transfection reagent (LipofectAMINE 2000; manufactured by GIBCO BRL).

24 hours after the gene introduction procedure described above, the cells with the gene introduced therein were recovered and suspended in a DMEM culture medium containing 0.6 mg/ml G418 (manufactured by GIBCO BRL), to prepare serial dilutions, which were inoculated on a 10-cm petri dish. Colonies appearing 2 weeks later were individually obtained and defined as C6-15 cell expressing the protein P2Y12, for use in the following experiment (WO 02/36631, Mol. Pharmacol., 60, 432,2001).

The C6-15 cell expressing the protein P2Y12 was cultured and recovered. After the cell was rinsed with PBS, the cell was suspended in 20 mM Tris-HCl, pH 7.4 containing 5 mmol/l EDTA and a protease inhibitor cocktail set Complete™ (manufactured by Boehringer Mannheim GmbH) and then homogenized with Polytron. After ultra-centrifugation, the resulting precipitate was suspended in 50 mM Tris-HCl, pH 7.4 containing 1 mM EDTA, 100 mM NaCl and Complete™. The resulting suspension was defined as a membrane fraction.

1.5 µl of an active ingredient or compound of the invention and 50 µl of 0.75 nM [$^3$H]-2-MeS-ADP (80 Ci/mmol; manufactured by Amersham Pharmacia Biotech) were added to 100 µl of the P2Y12 protein-expressing C6-15 cell membrane fraction (100 µg/ml) thus prepared, for incubation in 50 mM Tris-HCl, pH 7.4 containing 100 mM NaCl and 50 mM $MgCl_2$, at ambient temperature for one hour. Subsequently, the incubation mixture was recovered onto a glass filter with a cell harvester. Adding a microscintillator onto the glass filter, the radioactivity was assayed with a liquid scintillation counter. At the test, additionally, the radioactivity levels of such cell cultures with no addition of the compound and with addition of 1.5 µl of 100 µM 2-MeS-ADP were assayed as total binding and non-specific binding, respectively. Defining the total binding and the non-specific binding at inhibition ratios of 0% and 100%, respectively, the inhibition ratio (%) of an active ingredient or compound in accordance with the invention was calculated. The results from an active ingredient or the compound of the invention at 30 nM (final concentration) are shown in Table 2.

TABLE 2

Inhibition activity of the binding between P2Y12 and 2-MeS-ADP

| Test compounds | % inhibition |
| --- | --- |
| Example 18 | 96 |
| Example 22 | 75 |
| Example 28 | 63 |
| Example 178 | 30 |
| Example 259 | 52 |
| Example 265 | 40 |
| Example 279 | 31 |
| Example 290 | 74 |
| Example 336 | 46 |
| Example 406 | 80 |
| Example 425 | 93 |
| Example 429 | 98 |
| Example 463 | 62 |
| Example 501 | 95 |
| Example 522 | 80 |
| Example 532 | 36 |
| Example 583 | 80 |
| Example 619 | 73 |

A pharmaceutical composition comprising an active ingredient of the invention is prepared into tablets, powders, fine granules, granules, capsules, pills, liquids, injections, suppositories, ointments and paps, using carriers and excipients and other additives for general use, for oral or parenteral administration.

The clinical dose of an active ingredient of the invention is appropriately determined, taking account of for example the symptoms, body weight, age and sex of a patient to be administered. Generally, the daily oral dose is generally about 0.0001 to 50 mg/kg, preferably about 0.001 to 10 mg/kg, more preferably about 0.01 to 1 mg/kg, in one portion or in divided portions of 2 to 4. For intravenous administration, appropriately, the daily dose is appropriately about 0.0001 to 1 mg/kg, preferably about 0.0001 to 0.1 mg/kg per body weight, in one portion per day or in divided plural portions per day. The dose varies depending on the variable conditions. Therefore, a sufficient effect may sometimes be obtained at an amount smaller than the ranges of the doses.

As a solid composition for oral administration in accordance with the invention, for example, tablets, powders and granules are used. In such solid composition, one or more active substances are mixed with at least one inactive diluent type, including for example lactose, mannitol, glucose, hydroxypropyl cellulose, microcrystalline cellulose, starch, polyvinylpyrrolidone, and magnesium metasilicate aluminate. The composition may satisfactorily contain additives other than the inactive diluents, for example lubricants such as magnesium stearate, disintegrators such as fibrin calcium glycolate, stabilizers and auxiliary agents for dissolution. If necessary, the tablets and pills may be coated with sugar coatings of sucrose, gelatin, hydroxypropyl cellulose, and hydroxypropylmethyl cellulose phthalate or with films dissolvable in stomach or intestine.

The liquid composition for oral administration contains for example pharmaceutically acceptable emulsifiers, fluids, suspending agents, syrups and elixirs and also contain inactive diluents for general use, including for example distilled water, and ethanol (EtOH). The composition may satisfactorily contain auxiliary agents such as emollients and suspending agents, sweeteners, flavors, aromatic agents and preservatives other than the inactive diluents.

The injections for parenteral administration contain sterile, aqueous or non-aqueous fluids, suspending agents and emulsifiers. The aqueous fluids and the suspending agents include for example distilled water for injections and physiological saline. The non-aqueous fluids and suspending agents include for example propylene glycol, polyethylene glycol, vegetable oils such as olive oil, alcohols such as EtOH, polysorbate 80. Such composition further may contain preservatives, emollients, emulsifiers, dispersants, stabilizers and auxiliary agents for dissolution. These are sterilized by for example filtration through bacteria-deposit filters, blending of sterilizing agents or irradiation. These may also be used in a form of a sterile solid composition, which is preliminarily dissolved in sterile water or sterile solvents for injections.

BEST MODE FOR CARRYING OUT THE INVENTION

The invention is now specifically described in the following Examples but is never limited to these Examples. Herein, the starting material compounds for use in the Examples include novel substances. The processes from such starting material compounds are described in Reference Examples.

The symbols in the Tables represent the following meanings (the same is true hereinbelow).
Rf: Number of Reference Example
Ex: Number of Example (In case that only the number of Example is described in the column Ex, the compound is in the free form; in case that a diagonal line (/) and HCl are added after the number of Example, the compound is in the form of hydrochloride salt.)
Data: Physical data [Sal: Salt (no description of Sal indicates free form; in case that for example HCl is added, the compound is in the form of hydrochloride salt.)]
R, $R^1$, $R^2$, $R^3$, $R^4$, A: substituent groups in general formulas
(Me: methyl; Et: ethyl; nPr: n-propyl; iPr: isopropyl; iBu: isobutyl; sBu: sec-butyl; tBu: tert-butyl; nPen: n-pentyl; cPr: cyclopropyl; cBu: cyclobutyl; cPen: cyclopentyl; cHex: cyclohexyl; cHep: cycloheptyl; cOct: cyclooctyl; Ph: phenyl; Py: pyridyl; fur: furyl; the: thienyl; Bn: benzyl; btria: benzotriazolyl; bimid: benzoimidazolyl; pyrr: pyrrolidinyl; pipe: piperidinyl; pipa: piperazinyl; mor: morpholinyl; THF: tetrahydrofuranyl; THP: tetrahydropyranyl; THSP: tetrahydrothiopyranyl; 2-thiq: 3,4-dihydroisoquinolin-2(1H)-yl; Boc: tert-butyloxycarbonyl; Ac: acetyl; Bz: benzoyl; tri: tri; di: di. The number before a substituent group expresses the position substituted. Accordingly, for example, 4-EtO$_2$C-1-pipe represents 4-ethoxycarbonylpiperidin-1-yl and 2-the-(CH$_2$)$_2$—NH— represents 2-(thiophen-2-yl)ethylamino.)
Syn: production process (a numerical figure indicates the use of a corresponding starting material for production, like a compound of Example with the numerical figure; when two or more numbers are written, the production is done, using numbered production processes sequentially from the preceding numbers.)

REFERENCE EXAMPLE 1

3-Bromo-4-fluorobenzoic acid was dissolved in toluene, to which tert-butanol, triethylamine and diphenylphosphorylazide were sequentially added to stir at 100° C. for 20 hours, to obtain tert-butyl (3-bromo-4-fluorophenyl)carbamate.

FAB-MS(Neg): 288, 290 (M$^+$–1)

REFERENCE EXAMPLE 2

The compound of Reference Example 1 was dissolved in toluene, to which aniline, cesium carbonate, 2,2'-bis(diphenylphosphino)-1,1'-binaphthyl, and tris(dibenzylideneacetone)dipalladium were sequentially added for stirring at 110° C. for 2 days, to obtain tert-butyl (3-anilino-4-fluorophenyl)carbamate. The resulting compound was dissolved in EtOAc, to which 4M HCl-EtOAc solution was added for stirring at ambient temperature for one day, to obtain 4-fluoro-N$^3$-phenylbenzene-1,3-diamine.

FAB-MS(Pos): 203 (M$^+$+1)

REFERENCE EXAMPLE 3

Diethyl ethoxymethylenemalonate was added to 3,4-difluoroaniline at ambient temperature and the mixture was stirred at 130° C. for 17 hours. After diphenyl ether was additionally added to the reaction mixture, stirring was done at 260° C. for one hour. A solid obtained by leaving the reaction mixture to stand for cooling to ambient temperature was filtered, to obtain ethyl 6,7-difluoro-4-oxo-1,4-dihydroquinoline-3-carboxylate.

In the same manner as in the process of Reference Example 3, Reference Examples 4 through 10 in Table 3 were produced using the respective corresponding starting materials.

TABLE 3

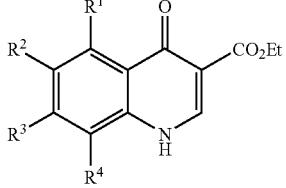

| Rf | $R^1$ | $R^2$ | $R^3$ | $R^4$ | Data |
|----|----|----|----|----|------|
| 3 | H | F | F | H | FAB-MS(Pos); 254(M$^+$ + 1) |
| 4 | H | Br | F | H | FAB-MS(Pos); 314, 316(M$^+$ + 1) |
| 5 | H | F | Ph-NH— | H | FAB-MS(Pos); 327(M$^+$ + 1) |
| 6 | H | H | F | H | FAB-MS(Pos); 236(M$^+$ + 1) |
| 7 | H | F | F | F | FAB-MS(Pos); 272(M$^+$ + 1) |
| 8 | H | Cl | F | H | FAB-MS(Pos); 270(M$^+$ + 1) |
| 9 | H | Me | F | H | FAB-MS(Pos); 250(M$^+$ + 1) |
| 10 | F | F | F | H | FAB-MS(Pos); 272(M$^+$ + 1) |

REFERENCE EXAMPLE 11

Ethyl 3-(2-chloro-4,5-difluorophenyl)-3-oxopropanoate produced according to Organic Preparations and Procedures International, 29, 231-234, 1997 was dissolved in acetic anhydride, to which ethyl orthoformate was added at ambient temperature, for stirring at 150° C. for one hour. The resulting mixture was concentrated under reduced pressure. The resulting residue was dissolved in EtOH, to which cyclopentylamine was added under ice cooling, for stirring at ambient temperature for one hour. The resulting mixture was concentrated under reduced pressure. The resulting residue was dissolved in 1,4-dioxane, to which 60% sodium hydride was added at ambient temperature, for stirring at 80° C. for 4 hours and subsequent concentration under reduced pressure. Then, aqueous hydrochloric acid solution was added to the resulting concentrate for chloroform extraction. The resulting organic layer was dried over anhydrous sodium sulfate and concentrated. The obtained residue was dissolved in acetic acid, to which aqueous 6 M HCl was added at ambient temperature for stirring at 120° C. for 5.5 hours, to obtain 1-cyclopentyl-6,7-difluoro-4-oxo-1,4-dihydroquinoline-3-carboxylic acid.

In the same manner as in the process of Reference Example 11, Reference Examples 12 through 28 as shown in Table 4 were produced using the respective corresponding starting materials.

TABLE 4

| Rf | R | Data |
|---|---|---|
| 11 | cPen | FAB-MS(Pos); 294(M+ + 1) |
| 12 | iPr | FAB-MS(Pos); 268(M+ + 1) |
| 13 | Ph | FAB-MS(Pos); 302(M+ + 1) |
| 14 | cHex | FAB-MS(Pos); 308(M+ + 1) |
| 15 | cBu | FAB-MS(Pos); 280(M+ + 1) |
| 16 | sBu | FAB-MS(Pos); 282(M+ + 1) |
| 17 | 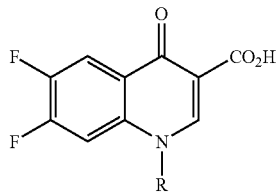 (1RS,2RS,4SR) | FAB-MS(Pos); 320(M+ + 1) |
| 18 | (Et)$_2$CH— | FAB-MS(Pos); 296(M+ + 1) |
| 19 | iPr-CH(Me)- | FAB-MS(Pos); 296(M+ + 1) |
| 20 | nPr-CH(Me)- | FAB-MS(Pos); 296(M+ + 1) |
| 21 | CF$_3$CH$_2$— | FAB-MS(Pos); 308(M+ + 1) |
| 22 | t-Bu-CH(Me)- | FAB-MS(Pos); 310(M+ + 1) |
| 23 | nPr-CH(Et)- | FAB-MS(Pos); 310(M+ + 1) |
| 24 | iBu | FAB-MS(Pos); 282(M+ + 1) |
| 25 | cPr | FAB-MS(Pos); 266(M+ + 1) |
| 26 | iBu-CH(Me)- | FAB-MS(Pos); 310(M+ + 1) |
| 27 | (nPr)$_2$CH— | FAB-MS(Pos); 324(M+ + 1) |
| 28 | 4,4-diMe-cHex | FAB-MS(Pos); 336(M+ + 1) |

REFERENCE EXAMPLE 29

The compound of Reference Example 5 was suspended in DMF, to which potassium carbonate and ethyl iodide were sequentially added under ice cooling, for stirring at ambient temperature for 4 days, to obtain ethyl 7-anilino-1-ethyl-6-fluoro-4-oxo-1,4-dihydroquinoline-3-carboxylate. The compound was suspended in aqueous 1M NaOH, for stirring at 100° C. for one hour, to obtain 7-anilino-1-ethyl-6-fluoro-4-oxo-1,4-dihydroquinoline-3-carboxylic acid.

FAB-MS(Pos): 327 (M++1)

REFERENCE EXAMPLE 30

The compound of Reference Example 3 was suspended in DMF, to which potassium carbonate and ethyl iodide were sequentially added under ice cooling, for stirring at ambient temperature for 24 hours and subsequent chloroform extraction. The resulting extract was concentrated under reduced pressure. The resulting residue was suspended in acetic acid, to which aqueous 6M HCl was added at ambient temperature for stirring at 120° C. for 4 hours, to obtain 6,7-difluoro-1-ethyl4-oxo-1,4-dihydroquinoline-3-carboxylic acid.

In the same manner as in the process of Reference Example 30, Reference Examples 31 through 39 as shown in Table 5 were produced using the respective corresponding starting materials.

TABLE 5

| Rf | R$^1$ | R$^2$ | R | Data |
|---|---|---|---|---|
| 30 | F | H | Et | FAB-MS(Pos); 254(M+ + 1) |
| 31 | F | H | Me | FAB-MS(Pos); 240(M+ + 1) |
| 32 | F | H | Rn | FAB-MS(Pos); 316(M+ + 1) |
| 33 | F | H | 4-MeO-Bn | FAB-MS(Pos); 346(M+ + 1) |
| 34 | F | H | allyl | FAB-MS(Pos); 266(M+ + 1) |
| 35 | H | H | Et | FAB-MS(Pos); 236(M+ + 1) |
| 36 | Br | H | Et | FAB-MS(Pos); 314, 316(M+ + 1) |
| 37 | F | F | Et | FAB-MS(Pos); 272(M+ + 1) |
| 38 | Cl | H | Et | FAB-MS(Pos); 270(M+ + 1) |
| 39 | Me | H | Et | FAB-MS(Pos); 250(M+ + 1) |

REFERENCE EXAMPLE 40

The compound of Reference Example 30 was suspended in DMSO, to which cyclohexylamine was added at ambient temperature, for stirring at 80° C. for 2 hours and subsequent recrystallization in aqueous 80% acetic acid solution, to obtain 7-(cyclohexylamino)-1-ethyl-6-fluoro-4-oxo-1,4-dihydroquinoline-3-carboxylic acid.

NMR(DMSO-d$_6$) δ; 1.10-1.25(m,1H), 1.27-1.50(m,7H), 1.60-1.70(m,1H), 1.72-1.82(m,2H), 1.90-2.00(m,2H), 3.55-3.67(m,1H), 4.53(q,J=7.4 Hz,2H), 6.65(dd,J=2.2,8.1 Hz,1H), 6.79(d,J=7.4 Hz,1H), 7.79(d,J=11.3 Hz,1H), 8.83(s, 1H), 15.78(s,1H)

In the same manner as in the process of Reference Example 40, Reference Examples 41 through 87 as shown in Tables 6 and 7 were produced using the respective corresponding starting materials.

TABLE 6

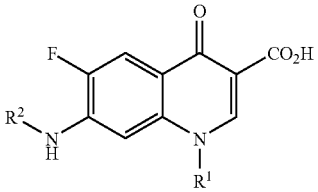

| Rf | R¹ | R² | Data |
|---|---|---|---|
| 40 | Et | cHex | FAB-MS(Pos); 333(M⁺ + 1) |
| 41 | Et | iPr | FAB-MS(Pos); 293(M⁺ + 1) |
| 42 | Et | tBu | FAB-MS(Pos); 307(M⁺ + 1) |
| 43 | Et | 4-THP | FAB-MS(Pos); 335(M⁺ + 1) |
| 44 | Et | cPen | FAB-MS(Pos); 319(M⁺ + 1) |
| 45 | Et | 1-Boc-4-pipe | FAB-MS(Pos); 434(M⁺ + 1) |
| 46 | Et | Ph | FAB-MS(Pos); 327(M⁺ + 1) |
| 47 | Et | cHep | FAB-MS(Pos); 347(M⁺ + 1) |

TABLE 6-continued

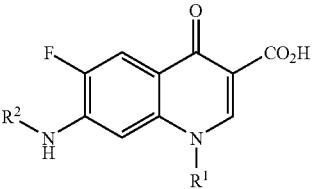

| Rf | R¹ | R² | Data |
|---|---|---|---|
| 48 | Et | cOct | FAB-MS(Pos); 361(M⁺ + 1) |
| 49 | Et | 1-Me-cHex | FAB-MS(Pos); 347(M⁺ + 1) |
| 50 | Et | 4-THSP | FAB-MS(Pos); 351(M⁺ + 1) |
| 51 | Et | 4-Me-cHex | FAB-MS(Pos); 347(M⁺ + 1) |
| 52 | Et | 4,4-diF-cHex | FAB-MS(Pos); 369(M⁺ + 1) |
| 53 | cPen | 4-THSP | FAB-MS(Pos); 391(M⁺ + 1) |
| 54 | cPen | 4,4-diF-cHex | FAB-MS(Pos); 409(M⁺ + 1) |
| 55 | cPen | 3-THP | FAB-MS(Pos); 375(M⁺ + 1) |

TABLE 7

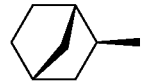

| Rf | R¹ | R² | R³ | R | Data |
|---|---|---|---|---|---|
| 56 | H | F | H | Me | FAB-MS(Pos); 319(M⁺ + 1) |
| 57 | H | F | H | iPr | FAB-MS(Pos); 347(M⁺ + 1) |
| 58 | H | F | H | Bn | FAB-MS(Pos); 395(M⁺ + 1) |
| 59 | H | F | H | cPen | FAB-MS(Pos); 373(M⁺ + 1) |
| 60 | H | F | H | 4-MeO-Bn | FAB-MS(Pos); 425(M⁺ + 1) |
| 61 | H | F | H | Ph | FAB-MS(Pos); 381(M⁺ + 1) |
| 62 | H | F | H | cHex | FAB-MS(Pos); 387(M⁺ + 1) |
| 63 | H | F | H | allyl | FAB-MS(Pos); 345(M⁺ + 1) |
| 64 | H | H | H | Et | FAB-MS(Pos); 315(M⁺ + 1) |
| 65 | H | Br | H | Et | FAB-MS(Pos); 393, 395(M⁺ + 1) |
| 66 | H | F | F | Et | FAB-MS(Pos); 351(M⁺ + 1) |
| 67 | H | Cl | H | Et | FAB-MS(Pos); 349(M⁺ + 1) |
| 68 | H | Me | H | Et | FAB-MS(Pos); 329(M⁺ + 1) |
| 69 | H | F | H | cBu | FAB-MS(Pos); 359(M⁺ + 1) |
| 70 | H | F | H | sBu | FAB-MS(Pos); 361(M⁺ + 1) |
| 71 | H | F | H | (1RS,2RS,4SR) norbornyl | FAB-MS(Pos); 399(M⁺ + 1) |
| 72 | H | F | H | (Et)₂CH— | FAB-MS(Pos); 375(M⁺ + 1) |
| 73 | H | F | H | iPr-CH(Me)- | FAB-MS(Pos); 375(M⁺ + 1) |
| 74 | H | F | H | nPr-CH(Me)- | FAB-MS(Pos); 375(M⁺ + 1) |
| 75 | H | F | H | CF₃CH₂— | FAB-MS(Pos); 387(M⁺ + 1) |
| 76 | H | F | H | t-Bu-CH(Me)- | FAB-MS(Pos); 389(M⁺ + 1) |
| 77 | H | F | H | nPr-CH(Et)- | FAB-MS(Pos); 389(M⁺ + 1) |
| 78 | H | F | H | iBu | FAB-MS(Pos); 361(M⁺ + 1) |
| 79 | H | F | H | cPr | FAB-MS(Pos); 345(M⁺ + 1) |
| 80 | H | F | H | iBu-CH(Et)- | FAB-MS(Pos); 389(M⁺ + 1) |
| 81 | H | F | H | (nPr)₂CH— | FAB-MS(Pos); 403(M⁺ + 1) |
| 82 | H | F | H | 4,4-diMe-cHex | FAB-MS(Pos); 415(M⁺ + 1) |
| 83 | H | F | H | (FCH₂)₂CH— | FAB-MS(Pos); 383(M⁺ + 1) |
| 84 | H | F | H | H₂C=C(CH₂F)— | FAB-MS(Pos); 363(M⁺ + 1) |
| 85 | NHMe | F | H | Et | ESI-MS(Pos); 362(M⁺ + 1) |
| 86 | NH(cHex) | F | H | Et | FAB-MS(Pos); 430(M⁺ + 1) |
| 87 | NH2 | F | H | Et | FAB-MS(Pos); 348(M⁺ + 1) |

REFERENCE EXAMPLE 88

The compound of Reference Example 10 was dissolved in DMF, to which potassium carbonate and ethyl iodide were sequentially added under ice cooling, for stirring at ambient temperature for 2 days, to obtain ethyl 1-ethyl-5,6,7-trifluoro-4-oxo-1,4-dihydroquinoline-3-carboxylate.

In the same manner as in the process of Reference Example 88, Reference Examples 89 through 91 as shown in Table 8 were produced using the respective corresponding starting materials.

TABLE 8

| Rf | R¹ | R | Data |
|---|---|---|---|
| 88 | F | Et | FAB-MS(Pos); 300(M⁺ + 1) |
| 89 | H | (1,3-dioxolan-2-yl)-CH₂— | FAB-MS(Pos); 340(M⁺ + 1) |
| 90 | H | tBuO₂CCH₂— | FAB-MS(Pos); 368(M⁺ + 1) |
| 91 | H | tBuO₂CCH(Me)- | FAB-MS(Pos); 382(M⁺ + 1) |

REFERENCE EXAMPLES 92 AND 93

The compound of Reference Example 88 was dissolved in DMSO, to which cyclohexylamine was added for stirring at 80° C. for one hour, to obtain ethyl 7-(cyclohexylamino)-1-ethyl-5,6-difluoro-4-oxo-1,4-dihydroquinoline-3-carboxylate (Reference Example 92) and ethyl 5-(cyclohexylamino)-1-ethyl-6,7-difluoro-4-oxo-1,4-dihydroquinoline-3-carboxylate (Reference Example 93).

REFERENCE EXAMPLE 93

FAB-MS(Pos): 379 (M⁺+1)

In the same manner as in the process of Reference Example 92, Reference Examples 94 through 103 and Reference Examples 104 through 106 as shown in Tables 9 and 10 were produced using the respective corresponding starting materials.

TABLE 9

| Rf | R¹ | R | A | Data |
|---|---|---|---|---|
| 92 | F | Et | CH | FAB-MS(Pos); 379(M⁺ + 1) |
| 94 | H | (1,3-dioxolan-2-yl)-CH₂— | CH | FAB-MS(Pos); 419(M⁺ + 1) |
| 95 | H | tBuO₂CCH₂— | CH | FAB-MS(Pos); 447(M⁺ + 1) |
| 96 | OMe | Et | CH | ESI-MS(Pos); 392(M⁺ + 1) |
| 97 | H | tBuO₂CCH(Me)- | CH | ESI-MS(Pos); 461(M⁺ + 1) |
| 98 | H | cPen | N | FAB-MS(Pos); 402(M⁺ + 1) |
| 99 | F | (Et)₂CH— | CH | FAB-MS(Pos); 421(M⁺ + 1) |
| 100 | AcN(Me)- | (Et)₂CH— | CH | ESI-MS(Pos); 474(M⁺ + 1) |

TABLE 10

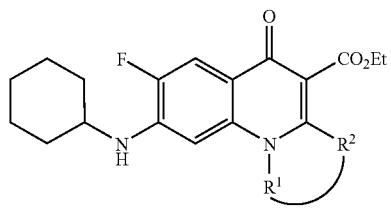

| Rf | —R¹—R²— | Data |
|---|---|---|
| 101 | —(CH₂)₃— | ESI-MS(Pos); 373(M⁺ + 1) |
| 102 | —C(=CH₂)—(CH₂)₂— | ESI-MS(Pos); 385(M⁺ + 1) |
| 103 | —CH₂—C(=CH₂)—(CH₂)₂— | ESI-MS(Pos); 399(M⁺ + 1) |

REFERENCE EXAMPLE 104

Ethyl 7-(cyclohexylamino)-1-cyclopentyl-6-fluoro-2-methyl-4-oxo-1,4-dihydroquinoline-3-carboxylate FAB-MS(Pos): 415 (M⁺+1)

REFERENCE EXAMPLE 105

Ethyl 9-(cyclohexylamino)-8-fluoro-6-oxo-6H-pyrido[1,2-a]quinoline-5-carboxylate FAB-MS(Pos): 383 (M⁺+1)

REFERENCE EXAMPLE 106

Ethyl [7-(cyclohexylamino)-6-fluoro-1-isopropyl-4-oxo-1,4-dihydro-1,8-naphthylidin-3-yl]carboxylate FAB-MS(Pos): 376 (M⁺+1)

REFERENCE EXAMPLE 107

Under ice cooling, triethylamine and 2,4,5-trifluorobenzoyl chloride were added to a solution of ethyl 3-(cyclopentylamino)buta-2-enoate in dioxane, for stirring at ambient temperature for 30 minutes and at 65° C. for one hour, to obtain ethyl 3-(cyclopentylamino)-2-(2,4,5-trifluorobenzoyl)buta-2-enoate.

FAB-MS(Pos): 356 (M⁺+1)

REFERENCE EXAMPLE 108

60% sodium hydride was added to a solution of the compound of Reference Example 107 in dioxane, for stirring at 70° C. for 2 hours, to obtain ethyl 1-cyclopentyl-6,7-difluoro-2-methyl-4-oxo-1,4-dihydroquinoline-3-carboxylate.

FAB-MS(Pos): 336 (M⁺+1)

REFERENCE EXAMPLE 109

Ethyl 3-(2-chloro-4,5-difluorophenyl)-3-oxopropanoate was dissolved in acetic anhydride, to which ethyl orthoformate was added at ambient temperature, for stirring at 140° C. for 12 hours and subsequent concentration under reduced pressure. The resulting residue was dissolved in EtOH, to which triethylamine and EtOH solution of tetrahydrofuran-3-amine hydrochloride was added under ice cooling, for stirring under ice cooling for 30 minutes and at ambient temperature for one hour. Water was then added for ethyl acetate extraction. The resulting extract was dried over anhydrous magnesium sulfate. The solvent was distilled off under reduced pressure. 60% sodium hydride was added to a suspension of the resulting residue in 1,4-dioxane, for stirring at 80° C. for 1.5 hours, to obtain ethyl 6,7-difluoro-4-oxo-1-(tetrahydrofuran-3-yl)-1,4-dihydroquinoline-3-carboxylate. The product was suspended in DMSO, to which cyclohexylamine was added, for stirring at 100° C. for 22 hours, to obtain ethyl 7-(cyclohexylamino)-6-fluoro-4-oxo-1-(tetrahydrofuran-3-yl)-1,4-dihydroquinoline-3-carboxylate.

In the same manner as in the process of Reference Example 109, Reference Examples 110 through 125 as shown in Table 11 were produced using the respective corresponding starting materials (In Reference Examples 123 and 124, the hydroxyl group in the corresponding starting materials was protected with tert-butyldimethylsilyl group).

REFERENCE EXAMPLE 127

The compound of Reference Example 95 was dissolved in methylene chloride, to which trifluoroacetic acid was added, for stirring at ambient temperature for 24 hours, to obtain [7-(cyclohexylamino)-3-(ethoxycarbonyl)-6-fluoro-4-oxoquinolin-1(4H)-yl]acetic acid trifluoroacetate.

FAB-MS(Pos): 391 ($M^+$+1)

In the same manner as in the process of Reference Example 127, Reference Example 128 was produced using the corresponding starting material.

REFERENCE EXAMPLE 128

2-[7-(Cyclohexylamino)-3-(ethoxycarbonyl)-6-fluoro-4-oxoquinolin-1(4H)-yl]propionic acid ESI-MS(Pos): 405 ($M^+$+1)

TABLE 11

| Rf | R | Data |
|---|---|---|
| 109 | 3-THF | FAB-MS(Pos); 403($M^+$ + 1) |
| 110 | 2,2-diMe-1,3-dioxan-5-yl | FAB-MS(Pos); 447($M^+$ + 1) |
| 111 | (3R)-3-THF | FAB-MS(Pos); 403($M^+$ + 1) |
| 112 | (3S)-3-THF | FAB-MS(Pos); 403($M^+$ + 1) |
| 113 | cyclopent-3-en-1-yl | FAB-MS(Pos); 399($M^+$ + 1) |
| 114 | oxetan-3-yl | FAB-MS(Pos); 389($M^+$ + 1) |
| 115 | 4-THP | FAB-MS(Pos); 417($M^+$ + 1) |
| 116 | (1RS,2SR,4SR) bicyclic | FAB-MS(Pos); 427($M^+$ + 1) |
| 117 | 1-Boc-3-pyrr | FAB-MS(Pos); 502($M^+$ + 1) |
| 118 | 1-Boc-4-pipe | FAB-MS(Pos); 516($M^+$ + 1) |
| 119 | 1-Boc-azetidin-3-yl | FAB-MS(Pos); 488($M^+$ + 1) |
| 120 | tBu | FAB-MS(Pos); 389($M^+$ + 1) |
| 121 | MeO(CH$_2$)$_2$— | FAB-MS(Pos); 391($M^+$ + 1) |
| 122 | CF$_3$CH(Me)- | FAB-MS(Pos); 429($M^+$ + 1) |
| 123 | (3aRS,4SR,6RS,6aSR) dioxolane-cyclopentanol | FAB-MS(Pos); 489($M^+$ + 1) |
| 124 | HO(CH$_2$)$_3$— | ESI-MS(Neg); 389($M^+$ − 1) |
| 125 | 3-methylcyclopent-3-en-1yl | FAB-MS(Pos); 413($M^+$ + 1) |

REFERENCE EXAMPLE 126

Palladium-carbon was added to a solution of the compound of Reference Example 105 in trifloroacetic acid, for stirring under hydrogen pressure for 12 hours, to obtain ethyl 9-(cyclohexylamino)-8-fluoro-6-oxo-2,3,4,6-tetrahydro-1H-pyrido[1,2-a]quinoline-5-carboxylate.

FAB-MS(Pos): 387 ($M^+$+1)

REFERENCE EXAMPLE 129

The compound of Reference Example 127 was dissolved in THF, to which 1,1'-carbonyldiimidazole was added under ice cooling, for stirring under ice cooling for one hour. Then water was added to the mixture, to which sodium borohydride was added, for stirring at ambient temperature for 4 hours, to obtain 7-(cyclohexylamino)-6-fluoro-1-(2-hydroxyethyl)-4-oxo-1,4-dihydroquinoline-3-carboxylate.

FAB-MS(Pos): 377 ($M^+$+1)

In the same manner as in the process of Reference Example 129, Reference Example 130 was produced using the corresponding starting material.

REFERENCE EXAMPLE 130

Ethyl 7-(cyclohexylamino)-6-fluoro-1-(2-hydroxy-1-methylethyl)-4-oxo-1,4-dihydroquinoline-3-carboxylate ESI-MS(Pos): 391 (M$^+$+1)

REFERENCE EXAMPLE 131

The compound of Reference Example 129 was dissolved in methylene chloride, to which pyridinium p-toluenesulfonate and dihydropyrane were sequentially added under ice cooling, for stirring at ambient temperature for 3 days, to obtain ethyl 7-(cyclohexylamino)-6-fluoro-4-oxo-1-[2-(tetrahydro-2H-pyran-2-yloxy)ethyl]-1,4-dihydroquinoline-3-carboxylate.

FAB-MS(Pos): 461 (M$^+$+1)

REFERENCE EXAMPLE 132

The compound of Reference Example 127 was dissolved in THF, to which 1,1'-carbonylbis-1H-imidazole was added under ice cooling, for stirring at ambient temperature for 2.5 hours. An aqueous methylamine solution was added to the resulting reaction mixture under ice cooling, for stirring at ambient temperature for one hour, to obtain ethyl 7-(cyclohexylamino)-6-fluoro-1-[2-(methylamino)-2-oxoethyl]-4-oxo-1,4-dihydroquinoline-3-carboxylate.

FAB-MS(Pos): 404 (M$^+$+1)

In the same manner as in the process of Reference Example 132, Reference Examples 133 through 134 were produced using the respective corresponding starting materials.

REFERENCE EXAMPLE 133

Ethyl 7-(cyclohexylamino)-6-fluoro-1-[2-(4-methylpiperazin-1-yl)-2-oxoethyl]-4-oxo-1,4-dihydroquinoline-3-carboxylate FAB-MS(Pos): 473 (M$^+$+1)

REFERENCE EXAMPLE 134

Ethyl 7-(cyclohexylamino)-6-fluoro-1-(2-morpholin-4-yl-2-oxoethyl)-4-oxo-1,4-dihydroquinoline-3-carboxylate FAB-MS(Pos): 460 (M$^+$+1)

REFERENCE EXAMPLE 135

An aqueous 70% acetic acid solution was added to the compound of Reference Example 110, for stirring at 80° C. for 18 hours, to obtain ethyl 7-(cyclohexylamino)-6-fluoro-1-[2-hydroxy-1-(hydroxymethyl)ethyl]-4-oxo-1,4-dihydroquinoline-3-carboxylate.

FAB-MS(Pos): 407 (M$^+$+1)

REFERENCE EXAMPLE 136

The compound of Reference Example 135 was dissolved in DMF, to which methyl iodide and silver oxide were added for stirring at ambient temperature for 51 hours, to obtain ethyl 7-(cyclohexylamino)-6-fluoro-1-[2-methoxy-1-(methoxymethyl)ethyl]-4-oxo-1,4-dihydroquinoline-3-carboxylate.

FAB-MS(Pos): 435 (M$^+$+1)

REFERENCE EXAMPLE 137

The compound of Reference Example 129 was dissolved in methylene chloride, to which triethylamine and methanesulfonyl chloride were added under ice cooling, for stirring at ambient temperature for 2 hours, to obtain a mesyl compound. The mesyl compound was dissolved in DMF, to which sodium azide was added for stirring at ambient temperature for 5 hours, to obtain an azide compound. The azide compound was dissolved in THF, to which triphenylphosphine was added, for stirring at 50° C. for one hour. Water was then added for stirring overnight at 80° C. Pyridine and acetic anhydride were added to the resulting reaction mixture, for stirring at ambient temperature for 3 hours, to obtain ethyl 1-[2-(acetylamino)ethyl]-7-(cyclohexylamino)-6-fluoro-4-oxo-1,4-dihydroquinoline-3-carboxylate.

ESI-MS(Pos): 418 (M$^+$+1)

In the same manner as in the process of Reference Example 137, Reference Examples 138 through 140 were produced using the respective corresponding starting materials.

REFERENCE EXAMPLE 138

Ethyl 1-[2-(acetylamino)propyl]-7-(cyclohexylamino)-6-fluoro-4-oxo-1,4-dihydroquinoline-3-carboxylate ESI-MS(Pos): 432 (M$^+$+1)

REFERENCE EXAMPLE 139

Ethyl 1-{2-(acetylamino)-1-[(acetylamino)methyl]ethyl}-7-(cyclohexylamino)-6-fluoro-4-oxo-1,4-dihydroquinoline-3-carboxylate FAB-MS(Pos): 489 (M$^+$+1)

REFERENCE EXAMPLE 140

Ethyl 1-[2-(acetylamino)-1-methylethyl]-7-(cyclohexylamino)-6-fluoro-4-oxo-1,4-dihydroquinoline-3-carboxylate.

ESI-MS(Pos): 432 (M$^+$+1)

REFERENCE EXAMPLE 141

The compound of Reference Example 117 was suspended in EtOAc, to which 4M HCl-EtOAc solution was added under ice cooling, for stirring as it was for one hour, overnight at ambient temperature and overnight at 50° C. Insoluble materials therein were filtered and dried. The dried materials were suspended in methylene chloride, to which sodium acetate, formaldehyde solution (36%) and sodium triacetoxyborohydride were added under ice cooling, for stirring for 45 minutes as the mixture remained as it was, to obtain ethyl 7-(cyclohexylamino)-6-fluoro-1-(1-methylpyrrolidin-3-yl)-4-oxo-1,4-dihydroquinoline-3-carboxylate.

FAB-MS(Pos): 416 (M$^+$+1)

In the same manner as in the process of Reference Example 141, Reference Examples 142 and 143 were produced using the respective corresponding starting materials.

REFERENCE EXAMPLE 142

Ethyl 7-(cyclohexylamino)-6-fluoro-1-(1-methylpiperidin-4-yl)-4-oxo-1,4-dihydroquinoline-3-carboxylate FAB-MS(Pos): 430 ($M^+$+1)

REFERENCE EXAMPLE 143

Ethyl 7-(cyclohexylamino)-6-fluoro-1-(1-methylazetidin-3-yl)-4-oxo-1,4-dihydroquinoline-3-carboxylate FAB-MS(Pos): 402 ($M^+$+1)

REFERENCE EXAMPLE 144

5-Methoxy-3,4-dihydro-2H-pyrrole and triethylamine were added to ethyl 3-oxo-3-(2,4,5-trifluorophenyl)propanoate, for stirring at 60° C. for 4 days, to obtain ethyl 3-oxo-2-pyrrolidin-2-ylidene-3-(2,4,5-trifluorophenyl)propanoate.
ESI-MS(Pos): 314 ($M^+$+1)

REFERENCE EXAMPLE 145

60% sodium hydride was added to a dioxane solution of the compound of Reference Example 144, for stirring at ambient temperature for one hour, to obtain ethyl 7,8-difluoro-5-oxo-1,2,3,5-tetrahydropyrrolo[1,2-a]quinoline-4-carboxylate.
ESI-MS(Pos): 294 ($M^+$+1)

REFERENCE EXAMPLE 146

Diethylaminosulfur trifluoride was added to a methylene chloride solution of the compound of Reference Example 130 in at −78° C. Then, the mixture was gradually warmed to ambient temperature over 2 hours, to obtain ethyl 7-(cyclohexylamino)-6-fluoro-1-(2-fluoro-1-methylethyl)-4-oxo-1,4-dihydroquinoline-3-carboxylate.
ESI-MS(Pos): 393 ($M^+$+1)

REFERENCE EXAMPLE 147

To a methylene chloride solution of the compound of Reference Example 130 were added triethylamine and methanesulfonyl chloride at 0° C., for stirring as it was for one hour, to obtain a mesyl compound. The mesyl compound was dissolved in THF, to which potassium tert-butoxide was added for stirring at ambient temperature for 3 hours, to obtain ethyl 7-(cyclohexylamino)-6-fluoro-1-isopropenyl-4-oxo-1,4-dihydroquinoline-3-carboxylate.
ESI-MS(Pos): 373 ($M^+$+1)

REFERENCE EXAMPLE 148

Sodium hydride and methyl iodide were added to a DMF solution of the compound of Reference Example 137 at 0° C., for stirring for 5 hours, to obtain ethyl 1-{2-[acetyl(methyl)amino]ethyl}-7-(cyclohexylamino)-6-fluoro-4-oxo-1,4-dihydroquinoline-3-carboxylate.
ESI-MS(Pos): 446 ($M^+$+1)
In the same manner as in the process of Reference Example 148, Reference Examples 149 was produced using the corresponding starting material.

REFERENCE EXAMPLE 149

Ethyl 1-{2-[acetyl(methyl)amino]-1-methylethyl}-7-(cyclohexylamino)-6-fluoro-4-oxo-1,4-dihydroquinoline-3-carboxylate ESI-MS(Pos): 446 ($M^+$+1)

REFERENCE EXAMPLE 150

Palladium-carbon and conc. hydrochloric acid were added to a EtOH solution of the compound of Reference Example 102, for stirring under hydrogen atmosphere for 12 hours, to obtain ethyl 8-(cyclohexylamino)-7-fluoro-1-methyl-5-oxo-1,2,3,5-tetrahydropyrrolo[1,2-a]quinoline-4-carboxylate.
ESI-MS(Pos): 387 ($M^+$+1)
In the same manner as in the process of Reference Example 150, Reference Examples 151 was produced using the corresponding starting material.

REFERENCE EXAMPLE 151

Ethyl 9-(cyclohexylamino)-8-fluoro-2-methyl-6-oxo-2,3,4,6-tetrahydro-1H-pyrido[1,2-a]quinoline-4-carboxylate ESI-MS(Pos): 401 ($M^+$+1)

REFERENCE EXAMPLE 152

Potassium carbonate and iodocyclopentane were added to a DMF solution of ethyl 6,7-difluoro-4-hydroxycinnoline-3-carboxylate, for stirring at 80° C. for 40 minutes, to obtain ethyl 1-cyclopentyl-6,7-difluoro-4-oxo-1,4-dihydrocinnoline-3-carboxylate.
FAB-MS(Pos): 323 ($M^+$+1)
In the same manner as in the process of Reference Example 152, Reference Examples 153 was produced using the corresponding starting material.

REFERENCE EXAMPLE 153

Ethyl 1-(1-ethylpropyl)-6,7-difluoro-4-oxo-1,4-dihydrocinnoline-3-carboxylate

FAB-MS(Pos): 325 ($M^+$+1)

REFERENCE EXAMPLES 154 AND 155

Ethyl 3-oxo-3-(2,4,5-trifluorophenyl)propanoate was dissolved in acetic anhydride, to which ethyl orthoformate was added at ambient temperature, for stirring at 140° C. for 3 hours and subsequent concentration under reduced pressure. The resulting residue was dissolved in EtOH, to which [2-fluoro-1-(fluoromethyl)ethyl]amine hydrochloride and triethylamine were added under ice cooling, for stirring at ambient temperature for 30 minutes and subsequent concentration under reduced pressure.
Water was added to the resulting residue, for ethyl acetate extraction. The resulting organic layer was washed with aqueous saturated sodium chloride, dried over anhydrous sodium sulfate and concentrated. The resulting residue was dissolved in acetonitrile, to which potassium carbonate was added at ambient temperature, for stirring at 50° C. for 15 hours and additional stirring at 80° C. for 7 hours, to obtain ethyl 6,7-difluoro-1-[2-fluoro-1-(fluoromethyl)ethyl]-4-oxo-1,4-dihydroquinoline-3-carboxylate (Reference Example 154) and ethyl 6,7-difluoro-1-[1-(fluoromethyl)vinyl]4-oxo-1,4-dihydroquinoline-3-carboxylate (Reference Example 155).

REFERENCE EXAMPLE 154

FAB-MS(Pos): 332 (M$^+$+1)

REFERENCE EXAMPLE 155

FAB-MS(Pos): 312 (M$^+$+1)

REFERENCE EXAMPLE 156

3-Pentanone, acetic acid and sodium triacetoxyborohydride were added to a 1,2-dichloroethane solution of 3,4,5-trifluoroaniline, for stirring at ambient temperature for 14 hours, to obtain N-(1-ethylpropyl)-3,4,5-trifluoroaniline.
EI-MS(Pos): 217 (M$^+$+1)

REFERENCE EXAMPLE 157

Diethyl (ethoxymethylene)malonate was added to the compound of Reference Example 156, for stirring at 130° C. for 20 hours, to obtain diethyl {[(1-ethylpropyl)(3,4,5-trifluorophenyl)amino]methylene}malonate.
FAB-MS(Pos): 388 (M$^+$+1)

REFERENCE EXAMPLE 158

Polyphosphoric acid was added to the compound of Reference Example 157, for stirring at 130° C. for 30 minutes, to obtain ethyl 1-(1-ethylpropyl)-5,6,7-trifluoro-4-oxo-1,4-dihydroquinoline-3-carboxylate.
FAB-MS(Pos): 342 (M$^+$+1)

REFERENCE EXAMPLE 159

The compound of Reference Example 88 was added to a toluene suspension of lithium methoxide, for stirring at ambient temperature for 3 days, to obtain ethyl 1-ethyl-6,7-difluoro-5-methoxy-4-oxo-1,4-dihydroquinoline-3-carboxylate.
ESI-MS(Pos): 312 (M$^+$+1)
In the same manner as in the process of Reference Example 159, Reference Example 160 was produced using the corresponding starting material.

REFERENCE EXAMPLE 160

5-(Benzyloxy)-7-(cyclohexylamino)-1-(1-ethylpropyl)-6-fluoro-4-oxo-1,4-dihydroquinoline-3-carboxylic acid ESI-MS(Pos): 481 (M$^+$+1)

REFERENCE EXAMPLE 161

An aqueous solution of methylamine was added to a toluene suspension of the compound of Reference Example 88, for stirring at 70° C. for 20 hours, to obtain ethyl 1-ethyl-6,7-difluoro-5-(methylamino)-4-oxo-1,4-dihydroquinoline-3-carboxylate.
ESI-MS(Pos): 311 (M$^+$+1)
In the same manner as in the process of Reference Example 161, Reference Example 162 was produced using the corresponding starting material.

REFERENCE EXAMPLE 162

Ethyl 5-(benzylamino)-1-ethyl-6,7-difluoro-4-oxo-1,4-dihydroquinoline-3-carboxylate FAB-MS(Pos): 387 (M$^+$+1)

REFERENCE EXAMPLE 163

3-Methylcyclopent-3-ene-1-carboxylic acid was dissolved in toluene, to which tert-butanol, triethylamine and diphenylphosphorylazide were sequentially added for stirring at 90° C. for 3 days, to obtain tert-butyl (3-methylcyclopent-3-en-1-yl)carbamate.
NMR(CDCl$_3$) δ; 1.44(s,9H), 1.71(brs,3H), 2.02-2.18(m,2H), 2.58-2.77(m,2H), 4.27(brs,1H), 4.69(brs,1H), 5.25(brs,1H)

REFERENCE EXAMPLE 164

The compound of Reference Example 163 was dissolved in methylene chloride, to which trifluoroacetic acid was added, for stirring at ambient temperature for 4 hours, to obtain 3-methylcyclopent-3-ene-1-amine trifluoroacetate. Ethyl 3-(2-chloro-4,5-difluorophenyl)-3-oxopropanoate was dissolved in acetic anhydride, to which ethyl orthoformate was added, for stirring at 150° C. for 2 hours and subsequent concentration under reduced pressure. The resulting residue was dissolved in EtOH, to which triethylamine and 3-methylcyclopent-3-ene-1-amine trifluoroacetate were sequentially added under ice cooling, for stirring under ice cooling for 18 hours, to obtain ethyl 2-(2-chloro-4,5-difluorobenzoyl)-3-[(3-methylcyclopenta-3-en-1-yl)amino]acrylate.
The resulting compound was dissolved in 1,4-dioxane, to which sodium hydride was added, for stirring at 50° C. for 3 hours, to obtain ethyl 6,7-difluoro-1-(3-methylcyclopenta-3-en-1-yl)-4-oxo-1,4-dihydroquinoline-3-carboxylate.
FAB-MS(Pos): 334 (M$^+$+1)

REFERENCE EXAMPLE 165

The compound of Reference Example 162 was dissolved in EtOH-acetic acid, to which palladium-carbon (10%) was added, for stirring under hydrogen atmosphere for 3 hours, to obtain ethyl 5-amino-1-ethyl-6,7-difluoro-4-oxo-1,4-dihydroquinoline-3-carboxylate.
FAB-MS(Pos): 297 (M$^+$+1)

REFERENCE EXAMPLE 166

3-Pentanone and p-toluenesulfonic acid monohydrate were added to a benzene solution of ethyl 7-(cyclohexylamino)-6-fluoro-1-[2-hydroxy-1-(hydroxymethyl)ethyl]-4-oxo-1,4-dihydroquinoline-3-carboxylate, for stirring under reflux under heating for 34 hours, to obtain ethyl 7-(cyclohexylamino)-1-(2,2-diethyl-1,3-dioxan-5-yl)-6-fluoro-4-oxo-1,4-dihydroquinoline-3-carboxylate.
FAB-MS(Pos): 475 (M$^+$+1)

REFERENCE EXAMPLE 167

The compound of Reference Example 92 was dissolved in EtOH-THF, to which 2M aqueous NaOH was added, for stirring at ambient temperature for 12 hours, to obtain 7-(cyclohexylamino)-1-ethyl-5,6-difluoro-4-oxo-1,4-dihydroquinoline-3-carboxylic acid.

In the same manner as in the process of Reference Example 167, Reference Examples 168 through 214 as shown in Tables 12 through 15 were produced using the respective corresponding starting materials.

TABLE 12

| Rf | R¹ | R | Data |
|---|---|---|---|
| 167 | F | Et | FAB-MS(Pos); 351($M^+ + 1$) |
| 168 | H | (1,3-dioxolan-2-yl)-CH$_2$— | FAB-MS(Pos); 391($M^+ + 1$) |
| 169 | H | 2,2-diMe-1,3-dioxan-5-yl | FAB-MS(Pos); 419($M^+ + 1$) |
| 170 | H | 3-THF | FAB-MS(Pos); 375($M^+ + 1$) |
| 171 | H | (3R)-3-THF | FAB-MS(Pos); 375($M^+ + 1$) |
| 172 | H | (3S)-3-THF | FAB-MS(Pos); 375($M^+ + 1$) |
| 173 | H | cyclopent-3-en-1-yl | FAB-MS(Pos); 371($M^+ + 1$) |
| 174 | H | oxetan-3-yl | FAB-MS(Pos); 361($M^+ + 1$) |
| 175 | H | 4-THP | FAB-MS(Pos); 389($M^+ + 1$) |
| 176 | H | 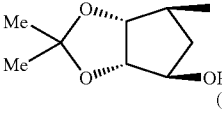 (1RS,2SR,4SR) | FAB-MS(Pos); 399($M^+ + 1$) |
| 177 | H | 1-Boc-3-pyrr | FAB-MS(Pos); 474($M^+ + 1$) |
| 178 | H | 1-Boc-4-pipe | FAB-MS(Pos); 488($M^+ + 1$) |
| 179 | H | tBu | FAB-MS(Pos); 361($M^+ + 1$) |
| 180 | H | MeO(CH$_2$)$_2$— | FAB-MS(Pos); 363($M^+ + 1$) |
| 181 | H | CF$_3$CH(Me)CH— | FAB-MS(Pos); 401($M^+ + 1$) |
| 182 | H | (3aRS,4SR,6RS,6aSR) | FAB-MS(Pos); 461($M^+ + 1$) |
| 183 | H | 2-THP-O—(CH$_2$)$_2$— | FAB-MS(Pos); 433($M^+ + 1$) |
| 184 | H | MeNH(CO)CH$_2$— | ESI-MS(Pos); 376($M^+ + 1$) |
| 185 | H | (4-Me-1-pipe)(CO)CH$_2$— | ESI-MS(Pos); 445($M^+ + 1$) |
| 186 | H | (4-mor)(CO)CH$_2$— | FAB-MS(Pos); 432($M^+ + 1$) |
| 187 | H | (MeO CH$_2$)$_2$CH— | FAB-MS(Pos); 407($M^+ + 1$) |
| 188 | H | AcNH(CH$_2$)$_2$— | FAB-MS(Pos); 390($M^+ + 1$) |
| 189 | H | AcNH(CH$_2$)$_3$— | FAB-MS(Pos); 404($M^+ + 1$) |
| 190 | H | (AcNHCH$_2$)$_2$CH— | FAB-MS(Pos); 461($M^+ + 1$) |
| 191 | H | 1-Me-3-pyrr | FAB-MS(Pos); 388($M^+ + 1$) |
| 192 | H | 1-Me-4-pipe | FAB-MS(Pos); 402($M^+ + 1$) |
| 193 | H | 1-Me-azetidin-3-yl | FAB-MS(Pos); 374($M^+ + 1$) |
| 194 | OMe | Et | ESI-MS(Pos); 363($M^+ + 1$) |
| 195 | H | FCH$_2$CH(Me)- | FAB-MS(Pos); 365($M^+ + 1$) |
| 196 | H | isopropenyl | FAB-MS(Pos); 345($M^+ + 1$) |
| 197 | H | AcNHCH$_2$CH(Me)- | FAB-MS(Pos); 404($M^+ + 1$) |
| 198 | H | AcN(Me)(CH$_2$)$_2$— | FAB-MS(Pos); 418($M^+ + 1$) |
| 199 | H | AcN(Me)CH$_2$CH(Me)- | FAB-MS(Pos); 418($M^+ + 1$) |
| 200 | NH(cHex) | Et | FAB-MS(Pos); 351($M^+ + 1$) |
| 201 | NHMe | Et | ESI-MS(Pos); 283($M^+ + 1$) |
| 202 | H | 3-methylcyclopent-3-en-lyl | FAB-MS(Pos); 385($M^+ + 1$) |
| 203 | H | 2-THP-OCH$_2$CH(Me)- | FAB-MS(Pos); 447($M^+ + 1$) |
| 204 | H | 2,2-diethyl-1,3-dioxan-5-yl | FAB-MS(Pos); 447($M^+ + 1$) |
| 205 | F | (Et)$_2$CH— | FAB-MS(Pos); 393($M^+ + 1$) |
| 206 | AcN(Me)- | (Et)$_2$CH— | ESI-MS(Pos); 446($M^+ + 1$) |

TABLE 13

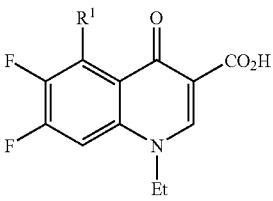

| Rf | R | Data |
|---|---|---|
| 207 | NH2 | FAB-MS(Pos); 269(M+ + 1) |
| 208 | NHMe | ESI-MS(Pos); 283(M+ + 1) |
| 209 | NH(cHex) | FAB-MS(Pos); 351(M+ + 1) |

TABLE 14

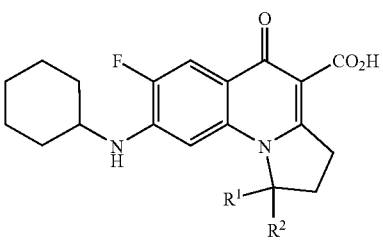

| Rf | R | R | Data |
|---|---|---|---|
| 210 | H | H | FAB-MS(Pos); 345(M+ + 1) |
| 211 | Me | H | FAB-MS(Pos); 359(M+ + 1) |
| 212 | CH2= | | FAB-MS(Pos); 357(M+ + 1) |

TABLE 15

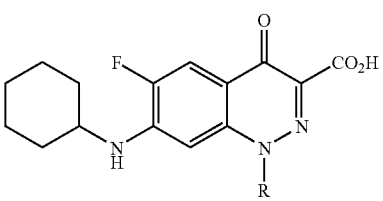

| Rf | R | Data |
|---|---|---|
| 213 | cPen | FAB-MS(Pos); 374(M+ + 1) |
| 214 | (Et)2CH— | FAB-MS(Pos); 376(M+ + 1) |

REFERENCE EXAMPLE 215

Aqueous LiOH was added to a EtOH-THF solution of the compound of Reference Example 104, for stirring at 60° C. for 24 hours and at 80° C. for 24 hours, to obtain 7-(cyclohexylamino)-1-cyclopentyl-6-fluoro-2-methyl-4-oxo-1,4-dihydroquinoline-3-carboxylic acid.

FAB-MS(Pos): 387 (M++1)

In the same manner as in the process of Reference Example 215, Reference Examples 216 through 220 were produced using the respective corresponding starting materials.

REFERENCE EXAMPLE 216

9-(Cyclohexylamino)-8-fluoro-6-oxo-6H-pyrido[1,2-a]quinoline-5-carboxylic acid

FAB-MS(Pos): 355 (M++1)

REFERENCE EXAMPLE 217

Ethyl [7-(cyclohexylamino)-6-fluoro-1-isopropyl4-oxo-1,4-dihydro-1,8-naphthylidin-3-yl]carboxylic acid FAB-MS(Pos): 348 (M++1)

REFERENCE EXAMPLE 218

Ethyl 9-(cyclohexylamino)-8-fluoro-6-oxo-2,3,4,6-tetrahydro-1H-pyrido[1,2-a]quinoline-5-carboxylic acid FAB-MS(Neg): 357 (M+−1)

REFERENCE EXAMPLE 219

9-(Cyclohexylamino)-8-fluoro-2-methylene-6-oxo-2,3,4,6-tetrahydro-1H-pyrido[1,2-a]quinoquinoline-5-carboxylic acid
FAB-MS(Pos): 371 (M++1)

REFERENCE EXAMPLE 220

9-(Cyclohexylamino)-8-fluoro-2-methyl-6-oxo-2,3,4,6-tetrahydro-1H-pyrido[-1,2-a]quinoline-5-carboxylic acid
FAB-MS(Pos): 373 (M++1)

REFERENCE EXAMPLE 221

An aqueous solution of sodium nitrate was added dropwise to an aqueous hydrochloric acid solution of 3,4-difluoroaniline under ice cooling, for stirring at the same temperature for 1.5 hours. The resulting reaction mixture was added dropwise to an aqueous EtOH solution of ethyl cyanoacetate and sodium acetate as prepared in a separate reaction flask, for stirring at ambient temperature for 2 hours, to obtain ethyl cyano[(3,4-difluorophenyl)diazenyl]acetate.
FAB-MS(Pos): 254 (M++1)

REFERENCE EXAMPLE 222

The compound of Reference Example 221 was suspended in acetonitrile, to which ethyl iodide and potassium carbonate were added for stirring at 50° C. for 7 days, to obtain ethyl 2-cyano[(3,4-difluorophenyl)(ethyl)hydrazono]acetate.
FAB-MS(Pos): 282 (M++1)

REFERENCE EXAMPLE 223

The compound of Reference Example 222 was suspended in EtOH, to which aqueous NaOH was added under ice cooling, for stirring at ambient temperature for 2 hours, to obtain 2-cyano[(3,4-difluorophenyl)(ethyl)hydrazono]acetic acid.
FAB-MS(Pos): 254 (M++1)

REFERENCE EXAMPLE 224

The compound of Reference Example 223 was suspended in toluene, to which thionyl chloride was added, for stirring at 90° C. for 1.5 hours and subsequent concentration under reduced pressure. The resulting residue was azeotropically evaporated with toluene. Hexane was added to the residue and the resulting solid was filtered. The solid was dissolved in dichloroethane, to which aluminium chloride was added for stirring at 55° C. for 24 hours and reflux for another 23 hours, to obtain 1-ethyl-6,7-difluoro-4-oxo-1,4-dihydrocinnoline-3-carbonitrile.

FAB-MS(Pos): 236 (M$^+$+1)

REFERENCE EXAMPLE 225

The compound of Reference Example 224 was dissolved in DMSO, to which cyclohexylamine was added, for stirring at 80° C. for 3 hours, to obtain 7-(cyclohexylamino)-1-ethyl-6-fluoro-4-oxo-1,4-dihydrocinnoline-3-carbonitrile.

FAB-MS(Pos): 315 (M$^+$+1)

REFERENCE EXAMPLE 226

The compound of Reference Example 225 was dissolved in acetic acid, to which aqueous HCl was added, for stirring at 120° C. for 2 days, to obtain 7-(cyclohexylamino)-1-ethyl-6-fluoro-4-oxo-1,4-dihydrocinnoline-3-carboxylic acid.

FAB-MS(Pos): 334 (M$^+$+1)

REFERENCE EXAMPLE 227

DMF and N-chlorosuccinimide were added to the compound of Reference Example 40, for stirring at 100° C. for 14 hours, to obtain 8-chloro-7-(cyclohexylamino)-1-ethyl-6-fluoro-4-oxo-1,4-dihydroquinoline-3-carboxylic acid.

FAB-MS(Pos): 367 (M$^+$+1)

REFERENCE EXAMPLE 228

Cyclohexylamine was added to a DMSO solution of the compound of Reference Example 153, for stirring at 80° C. for 14 hours. After the reaction mixture was cooled to ambient temperature, water and saturated aqueous ammonium chloride were added for chloroform extraction. The resulting organic layer was washed with saturated aqueous sodium chloride, dried over anhydrous sodium sulfate and concentrated. The resulting residue was dissolved in ethanol, to which aqueous 1N sodium hydroxide solution was added, for stirring at ambient temperature for 2 hours, to obtain 7-(cyclohexylamino)-1-(1-ethylpropyl)-6-fluoro-4-oxo-1,4-dihydrocinnoline-3-carboxylic acid.

FAB-MS(Pos): 376 (M$^+$+1)

REFERENCE EXAMPLE 229

Water and conc. hydrochloric acid were added to an acetic acid solution of the compound of Reference Example 154, for stirring at 100° C. for 5 hours, to obtain 6,7-difluoro-1-[2-fluoro-1-(fluoromethyl)ethyl]-4-oxo-1,4-fihydroquinoline-3-carboxylic acid.

FAB-MS(Pos): 304 (M$^+$+1)

In the same manner as in the process of Reference Example 229, Reference Example 230 was produced using the corresponding starting material.

REFERENCE EXAMPLE 230

6,7-Difluoro-1-[1-(fluoromethyl)vinyl]-4-oxo-1,4-dihydroquinoline-3-carboxylic acid FAB-MS(Pos): 284 (M$^+$+1)

REFERENCE EXAMPLE 231

The compound of Reference Example 130 was dissolved in methylene chloride, to which pyridinium p-toluenesulfonate and dihydropyrane were sequentially added for overnight stirring at ambient temperature, to obtain ethyl 7-(cyclohexylamino)-6-fluoro-1-[1-methyl-2-(tetrahydro-2H-pyran-2-yloxy)ethyl]-4-oxo-1,4-dihydroquinoline-3-carboxylate.

The resulting compound was suspended in EtOH-THF, to which 1M aqueous NaOH was added for overnight stirring, to obtain 7-(cyclohexylamino)-6-fluoro-1-[1-methyl-2-(tetrahydro-2H-pyran-2-yloxy)ethyl]-4-oxo-1,4-dihydroquinoline-3-carboxylic acid.

FAB-MS(Pos): 447 (M$^+$+1)

REFERENCE EXAMPLE 232

The compound of Reference Example 40 was suspended in DMF, to which 1,1'-carbonylbis-1H-imidazole was added at ambient temperature, for stirring at 100° C. for 24 hours, to obtain 7-(cyclohexylamino)-1-ethyl-6-fluoro-3-(1H-imidazol-1-ylcarbonyl)quinolin-4(1H)-one.

NMR(CDCl$_3$) δ; 1.25-1.53(m,5H), 1.59(t,J=7.6 Hz,3H), 1.65-1.76(m,1H), 1.80-1.90(m,2H), 2.05-2.15(m,2H), 3.34-3.45(m,1H), 4.22(q,J=7.6 Hz,2H), 4.57-4.66(m,1H), 6.44(d, J=6.4 Hz,1H), 7.04-7.05(m,1H), 7.51-7.53(m,1H), 7.99(d, J=12.0 Hz,1H), 8.12(s,1H), 8.15-8.16(m, 1H).

REFERENCE EXAMPLE 233

By the same method described below in Example 16, tert-butyl {[(6,7-difluoro-1-ethyl-4-oxo-1,4-dihydroquinolin-3-yl)carbonyl]amino}acetate was obtained from the compound of Reference Example 30.

FAB-MS(Pos): 367 (M+1)

In the same manner as in Reference Example 233, Reference Example 234 was produced using the corresponding starting material.

REFERENCE EXAMPLE 234

Ethyl {[(5-amino-1-ethyl-6,7-difluoro-4-oxo-1,4-dihydroquinolin-3-yl)carbonyl]amino}acetate FAB-MS(Pos): 354 (M$^+$+1)

REFERENCE EXAMPLE 235

Acetic anhydride was added to the compound of Reference Example 234, for stirring at 120° C. for 4 hours, to obtain ethyl ({[5-(acetylamino)-1-ethyl-6,7-difluoro-4-oxo-1,4-dihydroquinolin-3-yl]carbonyl}amino)acetate.

FAB-MS(Pos): 396 (M$^+$+1)

In the same manner as in Reference Example 235, Reference Example 236 was produced using the corresponding starting material.

REFERENCE EXAMPLE 236

Ethyl [5-(acetylmethylamino)-1-ethyl-6,7-difluoro-4-oxo-1,4-dihydroquinolin-3-yl]carboxylic acid ESI-MS(Pos): 395 (M$^+$+1)

REFERENCE EXAMPLE 237

(2-{[(9H-fluoren-9-ylmethoxy)carbonyl]amino}ethyl) phosphonic acid was suspended in benzene, to which benzyl N,N'-dicyclohexylimide carbamate was added, for stirring under reflux conditions for 4 hours, to obtain dibenzyl (2-{[(9H-fluoren-9-ylmethoxy)carbonyl]amino}ethyl)phosphonate.

FAB-MS(Pos): 528 (M$^+$+1)

REFERENCE EXAMPLE 238

The compound of Reference Example 237 was dissolved in DMF, to which diisopropylethylamine was added, for stirring at ambient temperature for 2 days, to obtain dibenzyl (2-aminoethyl)phosphonate. Further, oxalic acid was added to the resulting phosphonate, to obtain dibenzyl (2-aminoethyl) phosphonate oxalate.

FAB-MS(Pos): 306 (M$^+$+1)

REFERENCE EXAMPLE 239

Hydrazine monohydrate was added to a methylene chloride solution of diethyl [2-(1,3-dioxo-1,3-dihydro-2H-isoindol-2-yl)-1,1-difluoroethyl]phosphonate, for stirring at ambient temperature for one hour, to obtain diethyl (2-amino-1,1-difluoroethyl)phosphonate.

ESI-MS(Pos): 218 (M$^+$+1)

REFERENCE EXAMPLE 240

Diethyl pyridin-3-ylphosphonate was dissolved in EtOH-acetic acid, to which platinum oxide was added, for stirring under 3.4 kgf/cm$^2$ hydrogen for 120 hours, to obtain diethyl piperidin-3-ylphosphonate.

ESI-MS(Pos): 222 (M$^+$+1)

In the same manner as in the process of Reference Example 240, Reference Example 241 was produced using the corresponding starting material.

REFERENCE EXAMPLE 241

Diethyl (piperidin-2-ylmethyl)phosphonate

FAB-MS(Pos): 236 (M$^+$+1)

REFERENCE EXAMPLE 242

Palladium-carbon (10%) was added to a solution of benzyl ((3aRS, 4SR, 6RS, 6aRS)-6-{[tert-butyl(dimethyl)silyl]oxy}-2,2-dimethyltetrahydro-3aH-cyclopenta[d][1,3]dioxol-4-yl)carbamate in EtOH, for stirring overnight under hydrogen atmosphere, to obtain (3aRS, 4SR, 6RS, 6aRS)-6-{[tert-butyl(dimethyl)silyl]oxy}-2,2-dimethyltetrahydro-3aH-cyclopenta[d][1,3]dioxol-4-amine.

FAB-MS(Pos): 288 (M$^+$+1)

REFERENCE EXAMPLE 243

Platinum oxide and conc.HCl were added to a solution of diethyl (1-cyano-2-phenylethyl)phosphonate in EtOH, for overnight stirring under hydrogen atmosphere, to obtain diethyl [2-amino-1-(cyclohexylmethyl)ethyl]phosphonate.

FAB-MS(Pos): 278 (M$^+$+1)

EXAMPLE 1

400 mg of the compound of Reference Example 59 was suspended in 5.0 ml of DMF, to which 350 mg of 1,1'-carbonylbis-1H-imidazole was added at ambient temperature, for stirring at 100° C. for 20 hours. 0.2 ml of triethylamine and 180 mg of glycine ethyl ester hydrochloride were added sequentially to the resulting reaction mixture under ice cooling, for stirring at ambient temperature for another 5 hours. The reaction mixture was concentrated under reduced pressure, to which water was added for chloroform extraction. The resulting organic layer was dried over anhydrous sodium sulfate, filtered, and concentrated under reduced pressure. The resulting solid was recrystallized from EtOH, to obtain 408 mg of ethyl ({[7-(cyclohexylamino)-1-cyclopentyl-6-fluoro-4-oxo-1,4-dihydroquinolin-3-yl]carbonyl}amino)acetate.

EXAMPLE 2

300 mg of the compound of Reference Example 232 was dissolved in 5.0 ml of DMF, to which 0.2 ml of triethylamine and 120 mg of glycine ethyl ester hydrochloride were added sequentially to the resulting reaction mixture under ice cooling, for stirring at ambient temperature for 4.5 hours. The reaction mixture was concentrated under reduced pressure, to which water was added for chloroform extraction. The resulting organic layer was dried over anhydrous sodium sulfate, filtered, and concentrated under reduced pressure. The resulting solid was recrystallized from EtOH, to obtain 219 mg of ethyl ({[7-(cyclohexylamino)-1-ethyl-6-fluoro-4-oxo-1,4-dihydroquinolin-3-yl]carbonyl}amino)acetate.

EXAMPLE 3

The compound of Reference Example 232 was dissolved in 3.0 ml of DMF, to which 150 mg of O-trimesylsilylhydroxylamine was added under ice cooling, for stirring at 50° C. for 5.5 hours. The reaction mixture was concentrated under reduced pressure, to which 5.0 ml of MeOH was added. Subsequently, 4.0 ml of aqueous 1M HCl was added under ice cooling, for stirring at ambient temperature for 2 hours and at 50° C. for 2.5 hours. The resulting mixture was left to stand for cooling to ambient temperature, to obtain the resulting solid, which was then washed with EtOAc and then recrystallized from aqueous 80% acetic acid, to obtain 141 mg of 7-(cyclohexylamino)-1-ethyl-6-fluoro-N-hydroxy-4-oxo-1,4-dihydroquinoline-3-carboxamide.

EXAMPLE 4

300 mg of the compound of Example 56 was suspended in 5.0 ml of EtOH, to which 1.0 ml of aqueous 3M HCl was added under ice cooling, for stirring at 50° C. for 22 hours. The reaction mixture was concentrated under reduced pressure, to which water was added. The resulting mixture was neutralized with aqueous 1M NaOH, for 10% MeOH-chloroform extraction. The resulting organic layer was dried over anhydrous sodium sulfate, filtered and concentrated under reduced pressure. The resulting solid was washed with EtOH, to obtain 230 mg of 7-(cyclohexylamino)-1-ethyl-6-fluoro-4-oxo-N-[(1RS, 2RS, 3RS, 4SR)-2,3,4-trihydroxycyclopentyl]-1,4-dihydroquinoline-3-carboxamide.

EXAMPLE 5

360 mg of the compound of Example 51 was dissolved in 5.0 ml of methylene chloride, to which 2.0 ml of trifluoroacetic acid was added under ice cooling, for stirring at ambient temperature for 15 hours. The reaction mixture was concentrated under reduced pressure, to which water was added for chloroform extraction. The resulting organic layer was dried over anhydrous sodium sulfate, filtered and concentrated under reduced pressure. The resulting solid was washed from diisopropyl ether, to obtain 282 mg of (4S)-4-({[7-(cyclohexylamino)-1-ethyl-6-fluoro-4-oxo-1,4-dihydroquinolin-3-yl]carbonyl}amino)-5-[4-(ethoxycarbonyl)piperazin-1-yl]-5-oxopentanoic acid.

EXAMPLE 6

300 mg of the compound of Example 1 was suspended in 5.0 ml of EtOH, to which 0.8 ml of aqueous 1M NaOH was added under ice cooling, for stirring at ambient temperature for 25 hours. Water was added to the reaction mixture, which was neutralized with aqueous 1M HCl. The resulting solid was filtered and washed with EtOH, to obtain 263 mg of ({[7-(cyclohexylamino)-1-cyclopentyl-6-fluoro-4-oxo-1,4-dihydroquinolin-3-yl]carbonyl}amino)acetic acid.

EXAMPLE 7

2.23 ml of bromotrimethylsilane (TMSBr) was gradually added to a solution of 1.106 g of the compound of Example 44 in 20 ml of chloroform under ice cooling, for stirring under ice cooling for 30 minutes and then at ambient temperature for 6 hours. The reaction mixture was concentrated under reduced pressure, to which 15 ml of MeOH was added. Again, the resulting mixture was concentrated under reduced pressure, to which ether and a small amount of MeOH were added. The generated insoluble materials were filtered and recovered. 10 ml of aqueous 1M NaOH, MeOH and water were added to the insoluble materials, to filter off the insoluble matters. The precipitate resulting from the addition of 1 ml of aqueous 1M HCl to the filtrate was filtered. The precipitate was washed with 80% EtOH, to obtain 841 mg of [2-({[7-(cyclohexylamino)-1-ethyl-6-fluoro-4-oxo-1,4-dihydroquinolin-3-yl]carbonyl}amino)ethyl]phosphonic acid.

EXAMPLE 8

250 mg of the compound of Example 374 was suspended in 2.0 ml of EtOAc, to which 2.0 ml of 4M HCl-EtOAc solution was added under ice cooling, for stirring at ambient temperature for 4 days. The generated solid was filtered and washed with EtOAc, to obtain 210 mg of ({[1-ethyl-6-fluoro-4-oxo-(7-piperidin-4-ylamino)-1,4-dihydroquinolin-3-yl]carbonyl}amino)acetate hydrochloride.

EXAMPLE 9

300 mg of the compound of Example 163 was suspended in 5.0 ml of THF, to which 200 mg of 1,1'-carbonylbis-1H-imidazole was added under ice cooling, for stirring at ambient temperature for 17 hours. 1.0 ml of aqueous 28% ammonia was added to the resulting reaction mixture under ice cooling, for stirring at ambient temperature for another 1.5 hours. The reaction mixture was concentrated under reduced pressure, to which water was added for chloroform extraction. The resulting organic layer was dried over anhydrous sodium sulfate, filtered, concentrated under reduced pressure. The resulting solid was recrystallized from EtOH, to obtain 214 mg of N-(4-amino-4-oxobutyl)-7-(cyclohexylamino)-1-ethyl-6-fluoro-4-oxo-1,4-dihydroquinoline-carboxamide.

EXAMPLE 10

210 mg of the compound of Example 161 was suspended in 5.0 ml of DMF, to which 0.1 ml of ethoxycarbonylpiperazine, 130 mg of WSC.HCl and 100 mg of 1-hydroxybenzotriazole were added sequentially to the resulting reaction mixture under ice cooling, for stirring at ambient temperature for 17 hours. The reaction mixture was concentrated under reduced pressure, to which water was added for chloroform extraction. The resulting organic layer was washed sequentially with aqueous saturated NaHCO$_3$ and aqueous saturated sodium chloride, dried over anhydrous sodium sulfate, filtered, concentrated under reduced pressure. The resulting solid was washed with EtOH, to obtain 228 mg of ethyl 4-[({[7-(cyclohexylamino)-1-ethyl-6-fluoro-4-oxo-1,4-dihydroquinolin-3-yl]carbonyl}amino)acetyl]piperazine-1-carboxylate.

EXAMPLE 11

530 mg of the compound of Example 196 was suspended in a mixed solvent of 10 ml of acetone and 3.0 ml of water, to which 0.30 g of N-methylmorpholine-N-oxide and 2.0 ml of OsO$_4$ (2.5 wt % in BuOH) were sequentially added at ambient temperature, for stirring at ambient temperature for one week. Water was added to the reaction mixture, to which 2.0 g of sodium thiosulfate was added at ambient temperature, for overnight stirring at ambient temperature. Insoluble matters in the reaction mixture were filtered off, while the resulting filtrate was concentrated under reduced pressure. The resulting solid was washed with water, to obtain 190 mg of ethyl ({[7-(cyclohexylamino)-1-(2,3-dihydroxypropyl)-6-fluoro-4-oxo-1,4-dihydroquinolin-3-yl]carbonyl}amino)acetate.

EXAMPLE 12

423 mg of the compound of Example 72 was suspended in 5 ml of chloroform and 5 ml of MeOH, to which 126 mg of LiOH.H$_2$O was added, for stirring at ambient temperature for 30 minutes. 1.17 g of methyl-1-bromo-1-deoxy-2,3,4-tri-o-acetyl-α-D-glucopyranoside uronate was added to the reaction mixture, for stirring at ambient temperature for one hour. Further, 126 mg of LiOH.H$_2$O and 1.17 g of methyl-1-bromo-1-deoxy-2,3,4-tri-o-acetyl-α-D-glucopyranoside uronate were added, for stirring at ambient temperature for 6 hours. 15 ml of water, 5 ml of MeOH and 1.0 g of sodium carbonate were added to the reaction mixture, for stirring at ambient temperature for 1.5 hours. Additionally, 30 ml of water, 220 ml of MeOH and 1.0 g of sodium carbonate were added, for stirring at ambient temperature for 30 minutes. The resulting mixture was neutralized with acetic acid and stirred at ambient temperature for 12 hours. After the resulting insoluble matters were filtered off, water was added to the resulting filtrate, which was then washed with chloroform. The resulting aqueous solution was concentrated under reduced pressure. The residue was purified by ODS column chromatography, to obtain 168 mg of 3-({[7-(cyclohexylamino)-1-ethyl-6-fluoro-4-oxo-1,4-dihydroquinolin-3-yl]carbonyl}amino)phenyl β-D-glucopyranoside uronic acid.

EXAMPLE 13

0.20 g of the compound of Reference Example 233 was dissolved in 5.0 ml of DMSO, to which 2.0 ml of cyclohexylmethylamine was added at ambient temperature, for stirring at 80° C. for 19 hours. Water was added to the resulting reaction mixture, for chloroform extraction. The resulting organic layer was dried over anhydrous sodium sulfate, filtered and concentrated under reduced pressure. The resulting residue was purified by silica gel column chromatography, to obtain 0.23 g of tert-butyl [({7-[(cyclohexylmethyl)amino]-1-ethyl-6-fluoro-4-oxo-1,4-dihydroquinolin-3-yl}carbonyl)amino]acetate.

0.23 g of the tert-butyl ester compound was dissolved in 5.0 ml of methylene chloride, to which 2.0 ml of trifluoroacetic acid was added under ice cooling, for stirring at ambient temperature for 6 hours. The reaction mixture was concentrated under reduced pressure, to which water was added. The generated solid was filtered, to obtain 102 mg of [({7-[(cyclohexylmethyl)amino]-1-ethyl-6-fluoro-4-oxo-1,4-dihydroquinolin-3-yl}carbonyl)amino]acetic acid.

EXAMPLE 14

89 mg of sodium acetate, 55 µl of formaldehyde solution (37%), and 177 mg of sodium triacetoxyborohydride were added to a suspension of 253 mg of the compound of Example 210 in 10 ml of THF, for stirring at ambient temperature for 3 hours. Aqueous saturated $NaHCO_3$ was added for chloroform extraction. The resulting extract was washed with aqueous saturated sodium chloride. The resulting organic layer was dried over anhydrous magnesium sulfate, filtered and concentrated under reduced pressure. The resulting residue was purified by silica gel chromatography, to obtain 146 mg of ethyl ({[7-(cyclohexylamino)-6-fluoro-4-oxo-1-(1-methylpyrrolidin-3-yl)-1,4-dihydroquinolin-3-yl]carbonyl}amino)acetate.

EXAMPLE 15

0.45 g of the compound of Example 412 was dissolved in 10 ml of methylene chloride, to which 1.0 ml of bromotrimethylsilane was added under ice cooling, for stirring at ambient temperature for 3 days. The resulting reaction mixture was concentrated under reduced pressure, to which MeOH was added, for stirring at ambient temperature for 1.5 hours. The reaction mixture was concentrated under reduced pressure, to which EtOH was added, to filter the solid, to obtain 344 mg of [2-({[7-(cyclohexylamino)-1-cyclopentyl-6-fluoro-4-oxo-1,4-dihydroquinolin-3-yl]carbonyl}amino) ethyl]phosphonic acid hydrobromide.

EXAMPLE 16

The compound of Reference Example 75 was suspended in 20 ml, to which 149 µl of triethylamine and 177 µl of isobutyl chloroformate were added under ice cooling. After the mixture was stirred as it was for one hour, 149 µl of triethylamine and 138 mg of glycine ethyl ester hydrochloride were added, for stirring at ambient temperature for 12 hours. Aqueous saturated $NH_4Cl$ was added for chloroform extraction. The organic layer was dried over anhydrous sodium sulfate, filtered and concentrated under reduced pressure. The residue was purified by silica gel chromatography, and washed with EtOAc, to obtain 227 mg of ethyl ({[7-(cyclohexylamino)-6-fluoro-4-oxo-1-(2,2,2-trifluoroethyl)-1,4-dihydroquinolin-3-yl]carbonyl}amino)acetate.

EXAMPLE 17

0.51 g of the compound of Example 200 was dissolved in 5.0 ml of methylene chloride, to which 0.5 ml of triethylamine and 0.2 ml of methanesulfonyl chloride were added sequentially under ice cooling, for stirring under ice cooling for 30 minutes. Water was added to the resulting solution for chloroform extraction. The resulting organic layer was dried over anhydrous sodium sulfate, filtered and concentrated under reduced pressure, to obtain a mesyl compound. The resulting mesyl compound was dissolved in 10 ml of DMF, to which 0.10 g of sodium azide was added under ice cooling, for stirring at ambient temperature for 20 hours. Water was added to the resulting reaction mixture for chloroform extraction. The resulting organic layer was dried over anhydrous sodium sulfate, filtered and concentrated under reduced pressure, to obtain an azide compound. The resulting azide compound was dissolved in 10 ml of THF, to which 0.40 g of triphenylphosphine was added at ambient temperature, for stirring at 50° C. for one hour. 2.0 ml of water was added to the resulting reaction mixture for stirring at 80° C. for 3.5 hours. The reaction mixture was left to stand for cooling, to which 0.30 g of di-tert-butyl dicarbonate was added under ice cooling, for stirring at ambient temperature for 27 hours. Water was added to the reaction mixture, for chloroform extraction. The resulting organic layer was dried over anhydrous sodium sulfate, filtered and concentrated under reduced pressure. The resulting residue was purified by silica gel chromatography, to obtain 494 mg of ethyl {[(1-{2-[(tert-butoxycarbonyl)amino]ethyl}-7-(cyclohexylamino)-6-fluoro-4-oxo-1,4-dihydroquinolin-3-yl)carbonyl]amino}acetate.

EXAMPLE 18

407 mg of the compound of Example 589 was dissolved in 5 ml of MeOH, to which 30 mg of palladium-carbon (10%) was added, for stirring under hydrogen atmosphere for 3 hours. After 1.15 ml of aqueous 1M NaOH was added to the reaction mixture, the resulting insoluble matters were filtered off through Celite. Aqueous 1.15 ml of 1M HCl was added to the filtrate and the resulting precipitate was filtered and washed with water, to obtain 220 mg of [2-({[7-(cyclohexylamino)-1-(2,2-dimethyl-1,3-dioxan-5-yl)-6-fluoro-4-oxo-1,4-dihydroquinolin-3-yl]carbonyl}amino)ethyl]phosphonic acid.

EXAMPLE 19

415 mg of the compound of Example 200 was suspended in 5 ml of methylene chloride, to which 400 µl of triethylamine and 111 µl of methanesulfonyl chloride were added under ice cooling, for stirring at ambient temperature for 10 minutes. Water and aqueous saturated sodium chloride were added to the reaction mixture, for chloroform extraction. The organic layer was dried over anhydrous sodium sulfate, filtered and concentrated under reduced pressure. The resulting residue was dissolved in 5 ml of DMF, to which 948 µl of piperidine was added, for stirring at 70° C. for 23 hours. The reaction mixture was cooled to ambient temperature, to which water was added for chloroform extraction. The resulting organic layer was dried over anhydrous sodium sulfate, filtered and concentrated under reduced pressure. The resulting residue was purified by silica gel chromatography, to obtain 202 mg of ethyl ({[7-(cyclohexylamino)-6-fluoro-4-oxo-1-(2-piperidin-1-ylethyl)-1,4-dihydroquinolin-3-yl]carbonyl}amino) acetate.

EXAMPLE 20

149 mg of the compound of Example 31 was suspended in 5 ml of chloroform, to which 75 µl of triethylamine was added under ice cooling. Then 30 µl of acetyl chloride was added. After overnight stirring at ambient temperature, water was added for chloroform extraction and the resulting extract was washed with aqueous saturated sodium chloride. The resulting organic layer was dried over anhydrous magnesium sulfate, filtered and concentrated under reduced pressure. The resulting residue was purified by silica gel chromatography, to obtain 167 mg of ethyl ({[1-(1-acetylpyrrolidin-3-yl)-7-(cyclohexylamino)-6-fluoro-4-oxo-1,4-dihydroquinolin-3-yl]carbonyl}amino)acetate.

EXAMPLE 21

734 mg of the compound of Example 200 was suspended in 10 ml of methylene chloride, to which 708 μl of triethylamine and 197 μl of methanesulfonyl chloride were added under ice cooling, for stirring at ambient temperature for 15 minutes. Water and aqueous saturated sodium chloride were added to the reaction mixture, for chloroform extraction. The organic layer was dried over anhydrous sodium sulfate, filtered and concentrated under reduced pressure. The resulting residue was dissolved in 10 ml of DMSO, to which 100 mg of sodium cyanide was added, for stirring at 70° C. for 24 hours. Water and saturated aqueous sodium chloride were added to the reaction mixture for chloroform extraction. The resulting organic layer was dried over anhydrous sodium sulfate, filtered and concentrated under reduced pressure. The resulting residue was purified by silica gel chromatography, to obtain 354 mg of ethyl [({7-(cyclohexylamino)-6-fluoro-4-oxo-1,4-dihydroquinolin-3-yl]carbonyl}amino)acetate.

EXAMPLE 22

Aqueous 70% acetic acid was added to 146 mg of the compound of Example 18, for stirring at, 60° C. for 3 hours. The reaction mixture was concentrated under reduced pressure and azeotropically evaporated with EtOH. The resulting residue was crystallized from EtOH-water, to obtain 96 mg of ethyl {2-[({7-(cyclohexylamino)-6-fluoro-4-oxo-1-[2-hydroxy-1-(hydroxymethyl)ethyl]-4-oxo-1,4-dihydroquinolin-3-yl}carbonyl)amino]ethyl}phosphonic acid.

EXAMPLE 23

374 mg of methyl (2R)-2-({[7-(cyclohexylamino)-1-(1-ethylpropyl)-6-fluoro-4-oxo-1,4-dihydroquinolin-3-yl]carbonyl}amino)-3-pyridin-3-ylpropanoate was suspended in 4 ml of EtOAc, to which 2 ml of 0.5M HCl EtOAc solution was added, for stirring for 30 minutes. Subsequently, the resulting precipitate was filtered, to obtain 156 mg of methyl (2R)-2-({[7-(cyclohexylamino)-1-(1-ethylpropyl)-6-fluoro-4-oxo-1,4-dihydroquinolin-3-yl]carbonyl}amino)-3-pyridin-3-ylpropanoate hydrochloride.

EXAMPLE 24

0.5 ml of aqueous 2M NaOH was added to 11 mg of the compound of Example 44, for stirring at 100° C. for 30 minutes. 0.1 ml of 2-propanol was added, for stirring at 100° C. for 12 hours, to which 1.1 ml of aqueous 1M HCl was added. The generated precipitate was filtered and washed with diethyl ether, to obtain 7 mg of ethyl hydrogen [2-({[7-(cyclohexylamino)-1-ethyl-6-fluoro-4-oxo-1,4-dihydroquinolin-3-yl]carbonyl}amino)ethyl]phosphonate.

EXAMPLE 25

148 mg of the compound of Example 31 was suspended in 5 ml of acetonitrile, to which 67 mg of potassium carbonate, 46 μl of benzyl bromide and 5 ml of DMF were added for overnight stirring. Water was added, for chloroform extraction and rinsing with aqueous saturated sodium chloride. The resulting organic layer was dried over anhydrous magnesium sulfate, filtered and concentrated under reduced pressure. The resulting residue was purified by silica gel chromatography, to obtain 174 mg of Ethyl ({[1-(1-benzylpyrrolidin-3-yl)-7-(cyclohexylamino)-6-fluoro-4-oxo-1,4-dihydroquinolin-3-yl]carbonyl}amino)acetate.

EXAMPLE 26

183 mg of the compound of Example 220 was suspended in 20 ml of chloroform, to which 1.35 ml of bromotrimethylsilane was added under ice cooling, for stirring at ambient temperature for 24 hours. 1.35 ml of bromotrimethylsilane was added, for stirring for 3 days, to which EtOH was added. After the solvent was distilled off under reduced pressure, water and aqueous saturated NaHCO$_3$ were added to filter insoluble materials. Aqueous saturated NaHCO$_3$ was added to the insoluble materials, for chloroform extraction. The resulting extract was washed with aqueous 1M HCl, aqueous saturated NaHCO$_3$ and aqueous saturated sodium chloride. The resulting organic layer was dried over anhydrous sodium sulfate, filtered and concentrated under reduced pressure. The resulting residue was purified by silica gel chromatography, to obtain 54 mg of ethyl [({7-(cyclohexylamino)-6-fluoro-4-oxo-1-[(1RS, 2SR, 3RS, 4SR)-2,3,4-trihydroxycyclopentyl dihydroquinolin-3-yl}carbonyl)amino]acetate.

EXAMPLE 27

10 ml of acetonitrile, 720 μl of 1,8-diazabicyclo[5.4.0]-7-undecene and 575 μl of chloromethyl pivalate were added to 743 mg of the compound of Example 15, 226 mg of tetrabutylammonium hydrogensulfate and 102 mg of sodium iodide, for stirring at 75° C. for 65 hours. Water was added, for EtOAc extraction. The resulting extract was washed with water, saturated aqueous NaHCO$_3$, and aqueous saturated sodium chloride. The resulting organic layer was dried over anhydrous sodium sulfate, filtered and concentrated under reduced pressure. The resulting residue was purified by silica gel chromatography and washed with diethyl ether, to obtain 378 mg of bis {[(2,2-dimethylpropanoyl)oxy]methyl}[2-({[7-(cyclohexylamino)-1-cyclopentyl-6-fluoro-4-oxo-1,4-dihydroquinolin-3-yl]carbonyl}amino)ethyl]phosphonate.

EXAMPLE 28

273 mg of the compound of Example 544 was suspended in 10 ml of THF, to which 1.2 ml of aqueous 1M LiOH was added for stirring at ambient temperature for 2 days, at 50° C. for 3 hours and at 60° C. for 20 hours. After the solvent was distilled off under reduced pressure, aqueous 1M HCl was added and the generated precipitate was filtered, to obtain 270 mg of 2-({[7-(cyclohexylamino)-1-(1-ethylpropyl)-6-fluoro-4-oxo-1,4-dihydroquinolin-3-yl]carbonyl}amino)-2-methylpropionic acid.

EXAMPLE 29

148 mg of the compound of Example 31 was suspended in 5 ml of chloroform, to which 75 μl of triethylamine was added. The resulting mixture was cooled to −45° C., to which 32 μl of methanesulfonyl chloride was added. The mixture was gradually warmed and stirred overnight at ambient temperature. Then, water was added to the resulting mixture, for chloroform extraction and washing with aqueous saturated sodium chloride. The resulting organic layer was dried over anhydrous magnesium sulfate, filtered and concentrated under reduced pressure. The resulting residue was purified by silica gel chromatography, to obtain 138 mg of ethyl [({7-

(cyclohexylamino)-6-fluoro-1-[1-(methylsulfonyl)pyrrolidin-3-yl]-4-oxo-1,4-dihydroquinolin-3-yl}carbonyl)amino]acetate.

EXAMPLE 30

0.40 g, of the compound of Example 17 was suspended in 5.0 ml of EtOH, to which 1.1 ml of aqueous 1M NaOH was added under ice cooling, for stirring at ambient temperature for 25 hours.

The resulting reaction mixture was concentrated under reduced pressure. The resulting residue was dissolved in 20 ml of water, to which 3.0 ml of conc. hydrochloric acid was added under ice cooling, for stirring at 50° C. for 6 hours. The mixture was left to stand for cooling to ambient temperature. The generated solid was filtered, to obtain 0.15 g of ({[1-(2-aminoethyl)-7-(cyclohexylamino)-6-fluoro-4-oxo-1,4-dihydroquinolin-3-yl]carbonyl}amino)acetic acid hydrochloride.

EXAMPLE 31

Aqueous saturated $NaHCO_3$, water and EtOH were added to 1 g of the compound of Example 210, for chloroform extraction. The resulting organic layer was dried over anhydrous magnesium sulfate, filtered and concentrated under reduced pressure, to obtain 750 mg of ethyl ({[7-(cyclohexylamino)-6-fluoro-4-oxo-1-(pyrrolidin-3-yl)-1,4-dihydroquinolin-3-yl]carbonyl}amino)acetate.

EXAMPLE 32

2 ml of aqueous 6M HCl was added to 50 mg of the compound of Example 241, for stirring at 80° C. for 1.5 hours. 2 ml of aqueous 6M HCl was added to the resulting mixture, for stirring at 80° C. for one hour. After the solvent was distilled off under reduced pressure, water was added to the resulting residue, to filter insoluble materials. The materials were recrystallization from EtOH, to obtain 18 mg of [({7-(cyclohexylamino)-6-fluoro-1-[2-fluoro-1-(fluoromethyl) ethyl]-4-oxo dihydroquinolin-3-yl}carbonyl)amino]acetic acid was obtained.

EXAMPLE 33

52 mg of the compound of Example 348 was suspended in 1 ml of DMSO, to which 46 µl of triethylamine and 165 µl of a THF solution of 2.0 M dimethylamine were added, for stirring at 100° C. for 24 hours. Water was added and the generated precipitate was filtered. The precipitate was dissolved in ethyl acetate, and washed with water, saturated $NH_4Claq$ and aqueous saturated sodium chloride. The resulting organic layer was dried over anhydrous magnesium sulfate, filtered and concentrated under reduced pressure. The resulting residue was purified by silica gel chromatography, to obtain 43 mg of ethyl ({[7-(cyclohexylamino)-5-(dimethylamino)-1-(1-ethylpropyl)-6-fluoro-4-oxo-1,4-dihydroquinolin-3-yl]carbonyl}amino)acetate.

EXAMPLE 34

53 mg of the compound of Reference Example 235 was dissolved in 1.5 ml of DMSO, to which 31 µl of cyclohexylamine was added at ambient temperature, for stirring at 80° C. for 13 hours and at 100° C. for 10 hours. Water was added to the reaction mixture, and the generated precipitate was filtered and washed with water. The precipitate was purified by silica gel chromatography, to obtain 51 mg of ethyl ({[5-(acetylamino)-7-(cyclohexylamino)-1-ethyl-6-fluoro-4-oxo-1,4-dihydroquinolin-3-yl]carbonyl}amino)acetate.

The structures and physical data of the compounds of the Examples are shown below in Tables 16 through 41.

TABLE 16

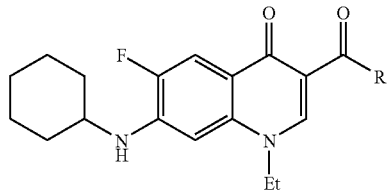

| Ex | Syn | R | Data |
|----|-----|---|------|
| 2 | 2 | $EtO_2CCH_2$—NH— | FAB-MS(Pos); 418($M^+$ + 1) |
| 3 | 3 | HO—NH— | FAB-MS(Pos); 348($M^+$ + 1) |
| 4 | 4 | (1RS,2SR,3RS,4SR)-2,3,4-triHO-cPen-NH— | FAB-MS(Pos); 448($M^+$ + 1) |
| 5 | 5 | (structure with $CO_2H$, $CO_2Et$, piperazine) | FAB-MS(Pos); 602($M^+$ + 1) |
| 7 | 7 | $(HO)_2(O)P$—$(CH_2)_2$—NH— | FAB-MS(Pos); 440($M^+$ + 1) |
| 9 | 9 | $H_2NOC(CH_2)_3$—NH— | FAB-MS(Pos); 417($M^+$ + 1) |
| 10 | 10 | (4-$EtO_2C$-1-pipe)-$COCH_2$—NH— | FAB-MS(Pos); 530($M^+$ + 1) |

TABLE 16-continued

[Structure: 7-(cyclohexylamino)-6-fluoro-1-ethyl-4-oxo-1,4-dihydroquinoline-3-carbonyl-R]

| Ex | Syn | R | Data |
|---|---|---|---|
| 12 | 12 | [3-(methylamino)phenyl β-D-glucuronide structure] | FAB-MS(Pos); 600(M⁺ + 1) |
| 24 | 24 | (HO)(EtO)(O)P—(CH₂)₂NH— | FAB-MS(Pos); 468(M⁺ + 1) |
| 35 | 1 | H₂N— | FAB-MS(Pos); 332(M⁺ + 1) |
| 36 | 1 | MeNH— | FAB-MS(Pos); 346(M⁺ + 1) |
| 37 | 1 | Me₂N— | FAB-MS(Pos); 360(M⁺ + 1) |
| 38 | 1 | BocHNNH— | FAB-MS(Pos); 447(M⁺ + 1) |
| 39 | 1 | Ph-NH— | FAB-MS(Pos); 408(M⁺ + 1) |
| 40 | 1 | H₂NC(=NH)—NH— | FAB-MS(Pos); 374(M⁺ + 1), Sal HCl |
| 41 | 1 | tBuO—NH— | FAB-MS(Pos); 404(M⁺ + 1) |
| 42 | 1 | 2-MeO₂C-1-pyrr | FAB-MS(Pos); 444(M⁺ + 1) |
| 43 | 1 | Me₂NOCCH(tBuO₂C(CH₂)₂)—NH— | FAB-MS(Pos); 545(M⁺ + 1) |
| 44 | 1 | (EtO)₂(O)P(CH₂)₂—NH— | FAB-MS(Pos); 496(M⁺ + 1) |
| 45 | 1 | 1-btria-O(CH₂)₃—NH— | FAB-MS(Pos); 507(M⁺ + 1) |
| 46 | 1 | 1-btria-O(CH₂)₂—NH— | FAB-MS(Pos); 493(M⁺ + 1) |
| 47 | 1 | (S)-H₂NOCCH(MeO₂C(CH₂)₂)—NH— | FAB-MS(Pos); 475(M⁺ + 1) |
| 48 | 1 | (S)-Ph-CH₂CH(CO₂Me)-NH— | FAB-MS(Pos); 494(M⁺ + 1) |
| 49 | 1 | (R)-Ph-CH₂CH(CO₂Me)-NH— | FAB-MS(Pos); 494(M⁺ + 1) |
| 50 | 1 | HOCH₂—CH(CO₂Me)-NH— | FAB-MS(Pos); 434(M⁺ + 1) |
| 51 | 1 | [structure: methylamino-(CO₂tBu-substituted)-CO-piperazine-N-CO₂Et] | FAB-MS(Pos); 658(M⁺ + 1) |
| 52 | 2 | (S)-H₂NOCCH(iBu)-NH— | FAB-MS(Pos); 445(M⁺ + 1) |
| 53 | 2 | HO(CH₂)₂—NH— | FAB-MS(Pos); 376(M⁺ + 1) |

TABLE 17

[Structure: 7-(cyclohexylamino)-6-fluoro-1-ethyl-4-oxo-1,4-dihydroquinoline-3-carbonyl-R]

| Ex | Syn | R | Data |
|---|---|---|---|
| 54 | 2 | EtO₂C(CH₂)₂—NH— | FAB-MS(Pos); 432(M⁺ + 1) |
| 55 | 2 | EtO₂C(CH₂)₃—NH— | FAB-MS(Pos); 446(M⁺ + 1) |

TABLE 17-continued

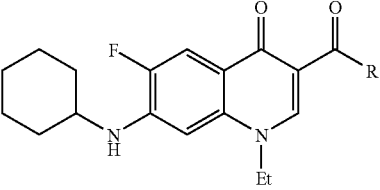

| Ex | Syn | R | Data |
|----|-----|---|------|
| 56 | 2 | 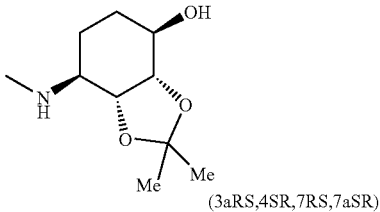 (3aRS,4SR,6RS,6aSR) | FAB-MS(Pos); 488(M$^+$ + 1) |
| 57 | 2 | 1-Me$_2$N-cHex-(CH$_2$)$_2$—NH— | FAB-MS(Pos); 485(M$^+$ + 1) |
| 58 | 2 | 4-EtO$_2$C-Ph-NH— | FAB-MS(Pos); 480(M$^+$ + 1) |
| 59 | 2 | 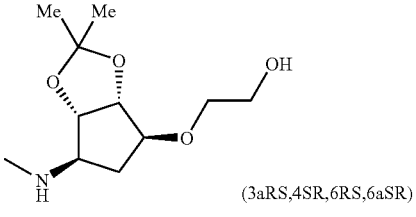 (3aRS,4SR,7RS,7aSR) | FAB-MS(Pos); 502(M$^+$ + 1) |
| 60 | 2 | (1R,2S)-2-Ph-cPr-NH— | FAB-MS(Pos); 448(M$^+$ + 1) |
| 61 | 2 | (3R)-3-(2-bimid)-1-pipe | FAB-MS(Pos); 516(M$^+$ + 1) |
| 62 | 2 | (3S)-3-(2-bimid)-1-pipe | FAB-MS(Pos); 516(M$^+$ + 1) |
| 63 | 2 | (1R,2S)-2-(3,4-diF-Ph)-cPr-NH— | FAB-MS(Pos); 484(M$^+$ + 1) |
| 64 | 2 | H$_2$NOCCH$_2$—NH— | FAB-MS(Pos); 389(M$^+$ + 1) |
| 65 | 2 | H$_2$NOC(CH$_2$)$_2$—NH— | FAB-MS(Pos); 403(M$^+$ + 1) |
| 66 | 2 | 3-EtO$_2$C-Ph-NH— | FAB-MS(Pos); 480(M$^+$ + 1) |
| 67 | 2 | 2-EtO$_2$C-Ph-NH— | FAB-MS(Pos); 480(M$^+$ + 1) |
| 68 | 2 | 3-H$_2$NOC-Ph-NH— | FAB-MS(Pos); 451(M$^+$ + 1) |
| 69 | 2 | (3aRS,4SR,6RS,6aSR) | FAB-MS(Pos); 532(M$^+$ + 1) |
| 70 | 2 | 4-EtO$_2$C-1-pipe | FAB-MS(Pos); 472(M$^+$ + 1) |
| 71 | 2 | 4-HO-Ph-NH— | FAB-MS(Pos); 424(M$^+$ + 1) |
| 72 | 2 | 3-HO-Ph-NH— | FAB-MS(Pos); 424(M$^+$ + 1) |
| 73 | 2 | 2-HO-Ph-NH— | FAB-MS(Pos); 424(M$^+$ + 1) |
| 74 | 2 | 4-H$_2$NOC-1-pipe | FAB-MS(Pos); 443(M$^+$ + 1) |
| 75 | 2 | HO$_3$S(CH$_2$)$_2$—NH— | FAB-MS(Pos); 440(M$^+$ + 1) |
| 76 | 2 | HO$_3$SO(CH$_2$)$_2$—NH— | FAB-MS(Pos); 456(M$^+$ + 1) |
| 77 | 2 | 2-HO-6-O$_2$N-Ph-NH— | FAB-MS(Pos); 469(M$^+$ + 1) |
| 78 | 2 | 2-H$_2$N-6-HO-Ph-NH— | FAB-MS(Pos); 439(M$^+$ + 1) |

TABLE 18

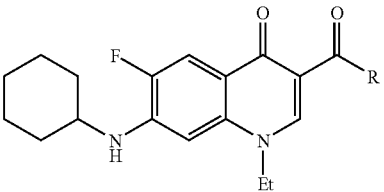

| Ex | Syn | R | Data |
|---|---|---|---|
| 79 | 2 | 6-AcO-2-AcNH-Ph-NH— | FAB-MS(Pos); 523(M⁺ + 1) |
| 80 | 2 | 2-AcNH-3-HO-Ph-NH— | FAB-MS(Pos); 481(M⁺ + 1) |
| 81 | 2 | 2-AcNH-6-HO-Ph-NH— | FAB-MS(Pos); 481(M⁺ + 1) |
| 82 | 2 | 2-BzNH-6-HO-Ph-NH— | FAB-MS(Pos); 543(M⁺ + 1) |
| 83 | 2 | 2-BzNH-3-HO-Ph-NH— | FAB-MS(Pos); 543(M⁺ + 1) |
| 84 | 2 | 6-HO-2-(Ph-HNOC)-Ph-NH— | FAB-MS(Pos); 543(M⁺ + 1) |
| 85 | 2 | 6-HO-2-(Me-HNOC)-Ph-NH— | FAB-MS(Pos); 481(M⁺ + 1) |
| 86 | 2 | 1,3,4-thiadiazol-2-yl-NH— | ESI-MS(Pos); 416(M⁺ + 1) |
| 87 | 2 | 2-MeO-Ph-NH— | ESI-MS(Pos); 438(M⁺ + 1) |
| 88 | 2 | 3,4-diMeO-Ph-NH— | ESI-MS(Pos); 468(M⁺ + 1) |
| 89 | 2 | 3-HO-2-Me-Ph-NH— | ESI-MS(Pos); 438(M⁺ + 1) |
| 90 | 2 | 4-HO-2-Me-Ph-NH— | ESI-MS(Pos); 438(M⁺ + 1) |
| 91 | 2 | 4-HO-3-O₂N-Ph-NH— | ESI-MS(Pos); 469(M⁺ + 1) |
| 92 | 2 | 3-Et₂NCH₂-4-HO-Ph-NH— | ESI-MS(Pos); 509(M⁺ + 1) |
| 93 | 2 | 3-HO-2-Py-NH— | ESI-MS(Pos); 425(M⁺ + 1) |
| 94 | 2 | 2-HOCH₂-Ph-NH— | ESI-MS(Pos); 438(M⁺ + 1) |
| 95 | 2 | 3-HOCH₂-Ph-NH— | ESI-MS(Pos); 438(M⁺ + 1) |
| 96 | 2 | 4-HOCH₂-Ph-NH— | ESI-MS(Pos); 438(M⁺ + 1) |

TABLE 18-continued

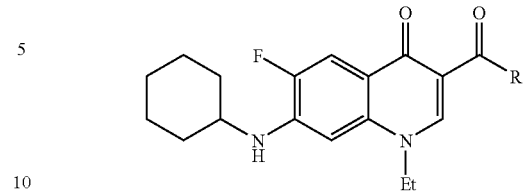

| Ex | Syn | R | Data |
|---|---|---|---|
| 97 | 2 | 2-HO(CH₂)₂Ph-NH— | ESI-MS(Pos); 452(M⁺ + 1) |
| 98 | 2 | indol-5-yl-NH— | ESI-MS(Pos); 447(M⁺ + 1) |
| 99 | 2 | indazol-5-yl-NH— | ESI-MS(Pos); 448(M⁺ + 1) |
| 100 | 2 | 4-AcNH-Ph-NH— | ESI-MS(Pos); 465(M⁺ + 1) |
| 101 | 2 | 4-(4-mor-CO)-Ph-NH— | ESI-MS(Pos); 521(M⁺ + 1) |
| 102 | 2 | 3-Ac-Ph-NH— | ESI-MS(Pos); 450(M⁺ + 1) |
| 103 | 2 | Bn-NH— | ESI-MS(Pos); 422(M⁺ + 1) |
| 104 | 2 | 2-Me-Bn-NH— | ESI-MS(Pos); 436(M⁺ + 1) |
| 105 | 2 | 2-F-Bn-NH— | ESI-MS(Pos); 440(M⁺ + 1) |
| 106 | 2 | 3-F-Bn-NH— | ESI-MS(Pos); 440(M⁺ + 1) |
| 107 | 2 | 4-F-Bn-NH— | ESI-MS(Pos); 440(M⁺ + 1) |
| 108 | 2 | 3-MeO-Bn-NH— | ESI-MS(Pos); 452(M⁺ + 1) |
| 109 | 2 | 4-MeO-Bn-NH— | ESI-MS(Pos); 452(M⁺ + 1) |
| 110 | 2 | 2,4-diMeO-Bn-NH— | ESI-MS(Pos); 482(M⁺ + 1) |
| 111 | 2 | 3,5-diMeO-Bn-NH— | ESI-MS(Pos); 482(M⁺ + 1) |
| 112 | 2 | 3-O₂N-Bn-NH— | ESI-MS(Pos); 467(M⁺ + 1) |
| 113 | 2 | 4-O₂N-Bn-NH— | ESI-MS(Pos); 467(M⁺ + 1) |
| 114 | 2 | Ph₂CH—NH— | ESI-MS(Pos); 498(M⁺ + 1) |

TABLE 19

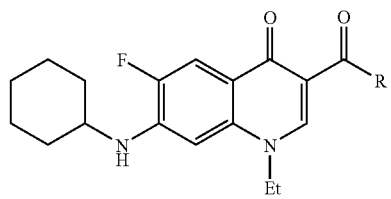

| Ex | Syn | R | Data |
|---|---|---|---|
| 115 | 2 | 2-fur-CH₂—NH— | ESI-MS(Pos); 412 (M⁺ + 1) |
| 116 | 2 | 2-the-CH₂—N— | ESI-MS(Pos); 428 (M⁺ + 1) |
| 117 | 2 | 3-Py-CH₂—N— | ESI-MS(Pos); 423 (M⁺ + 1) |
| 118 | 2 | 4-Py-CH₂—N— | ESI-MS(Pos); 423 (M⁺ + 1) |
| 119 | 2 | 2-F-Ph-(CH₂)₂—NH— | ESI-MS(Pos); 454 (M⁺ + 1) |
| 120 | 2 | 3-F-Ph-(CH₂)₂—NH— | ESI-MS(Pos); 454 (M⁺ + 1) |
| 121 | 2 | 4-F-Ph-(CH₂)₂—NH— | ESI-MS(Pos); 454 (M⁺ + 1) |
| 122 | 2 | 4-Me-Ph-(CH₂)₂—NH— | ESI-MS(Pos); 450 (M⁺ + 1) |
| 123 | 2 | 4-MeO-Ph-(CH₂)₂—NH— | ESI-MS(Pos); 466 (M⁺ + 1) |
| 124 | 2 | 2-Cl-Ph-(CH₂)₂—NH— | ESI-MS(Pos); 470 (M⁺ + 1) |
| 125 | 2 | 4-Cl-Ph-(CH₂)₂—NH— | ESI-MS(Pos); 470 (M⁺ + 1) |
| 126 | 2 | 4-Br-Ph-(CH₂)₂—NH— | ESI-MS(Pos); 514, 516 (M⁺ + 1) |

TABLE 19-continued

[Structure: 7-(cyclohexylamino)-6-fluoro-1-ethyl-4-oxo-1,4-dihydroquinoline-3-carbonyl-R]

| Ex | Syn | R | Data |
|---|---|---|---|
| 127 | 2 | 2-the-(CH$_2$)$_2$—NH— | ESI-MS(Pos); 442 (M$^+$ + 1) |
| 128 | 2 | 2-Py-(CH$_2$)$_2$—NH— | ESI-MS(Pos); 437 (M$^+$ + 1) |
| 129 | 2 | 3-Py-(CH$_2$)$_2$—NH— | ESI-MS(Pos); 437 (M$^+$ + 1) |
| 130 | 2 | 4-Py-(CH$_2$)$_2$—NH— | ESI-MS(Pos); 437 (M$^+$ + 1) |
| 131 | 2 | 2,5-diMeO-Ph-(CH$_2$)$_2$—NH— | ESI-MS(Pos); 496 (M$^+$ + 1) |
| 132 | 2 | 3,4-diMeO-Ph-(CH$_2$)$_2$—NH— | ESI-MS(Pos); 496 (M$^+$ + 1) |
| 133 | 2 | indol-3-yl-(CH$_2$)$_2$—NH— | ESI-MS(Pos); 475 (M$^+$ + 1) |
| 134 | 2 | Me$_2$NCH(Ph)CH$_2$—N— | ESI-MS(Pos); 479 (M$^+$ + 1) |
| 135 | 2 | PhS(═O)$_2$—(CH$_2$)$_2$—NH— | ESI-MS(Pos); 500 (M$^+$ + 1) |
| 136 | 2 | (3-Me-Ph)-N(Et)-(CH$_2$)$_2$—NH— | ESI-MS(Pos); 493 (M$^+$ + 1) |
| 137 | 2 | 4-Ph-1-pipa-CH$_2$CH(Me)-NH— | ESI-MS(Pos); 534 (M$^+$ + 1) |
| 138 | 2 | PhO-CH$_2$CH(4-mor-CH$_2$)—NH— | ESI-MS(Pos); 551 (M$^+$ + 1) |
| 139 | 2 | 4-(4-F-Bn)-2-mor-CH$_2$—N— | ESI-MS(Pos); 539 (M$^+$ + 1) |
| 140 | 2 | Et-NH— | ESI-MS(Pos); 360 (M$^+$ + 1) |
| 141 | 2 | nPen-NH— | ESI-MS(Pos); 402 (M$^+$ + 1) |
| 142 | 2 | HOCH$_2$CH(Me)-NH— | ESI-MS(Pos); 390 (M$^+$ + 1) |
| 143 | 2 | HOCH(Me)CH$_2$—N— | ESI-MS(Pos); 390 (M$^+$ + 1) |
| 144 | 2 | HO(CH$_2$)$_2$O(CH$_2$)$_2$—NH— | ESI-MS(Pos); 420 (M$^+$ + 1) |
| 145 | 2 | (HOCH$_2$)$_2$CH—NH— | ESI-MS(Pos); 406 (M$^+$ + 1) |
| 146 | 2 | HOCH$_2$CH(HO)CH$_2$—N— | ESI-MS(Pos); 406 (M$^+$ + 1) |
| 147 | 2 | HO(CH$_2$)$_5$—NH— | ESI-MS(Pos); 418 (M$^+$ + 1) |
| 148 | 2 | cPen-NH— | ESI-MS(Pos); 400 (M$^+$ + 1) |
| 149 | 2 | (1S,2S)-2-MeS-cPen-NH— | ESI-MS(Pos); 446 (M$^+$ + 1) |

TABLE 20

[Structure: 7-(cyclohexylamino)-6-fluoro-1-ethyl-4-oxo-1,4-dihydroquinoline-3-carbonyl-R]

| Ex | Syn | R | Data |
|---|---|---|---|
| 150 | 2 | (3S,4R)-4-MeS-3-THF-NH— | ESI-MS(Pos); 448(M$^+$ + 1) |
| 151 | 2 | 3-Bn-1-pyrr | ESI-MS(Pos); 476(M$^+$ + 1) |
| 152 | 2 | 3-PhS(═O)2-1-pyrr | ESI-MS(Pos); 526(M$^+$ + 1) |
| 153 | 2 | 4-(2-oxo-1-bimid)-1-pipe | ESI-MS(Pos); 532(M$^+$ + 1) |
| 154 | 2 | 4-(2-Cl-Ph)-1-pipa | ESI-MS(Pos); 511(M$^+$ + 1) |
| 155 | 2 | 4-(3-F$_3$C-Ph)-1-pipa | ESI-MS(Pos); 545(M$^+$ + 1) |
| 156 | 2 | 4-(2-Py)-1-pipa | ESI-MS(Pos); 478(M$^+$ + 1) |
| 157 | 2 | (1R,2R)2-Me$_2$N-cHex-N(allyl)- | ESI-MS(Pos); 497(M$^+$ + 1) |
| 158 | 4 | (1RS,2SR,3RS,4SR)-2,3,4-triHO-cHex-NH— | FAB-MS(Pos); 462(M$^+$ + 1) |
| 159 | 4 | (1RS,2SR,3SR,4SR)-(2,3-diHO-4-HO(CH$_2$)$_2$O)-cPen-NH— | FAB-MS(Pos); 492(M$^+$ + 1) |
| 160 | 5 | HO$_2$C(CH$_2$)$_2$—CH(CONMe$_2$)— | FAB-MS(Pos); 489(M$^+$ + 1) |
| 161 | 6 | HO$_2$CCH$_2$—N— | FAB-MS(Pos); 390(M$^+$ + 1) |
| 162 | 6 | HO$_2$C(CH$_2$)$_2$—NH— | FAB-MS(Pos); 404(M$^+$ + 1) |
| 163 | 6 | HO$_2$C(CH$_2$)$_3$—NH— | FAB-MS(Pos); 418(M$^+$ + 1) |
| 164 | 6 | 4-HO$_2$C-Ph-NH— | FAB-MS(Pos); 452(M$^+$ + 1) |
| 165 | 6 | HO$_2$C(CH$_2$)$_4$—NH— | FAB-MS(Pos); 432(M$^+$ + 1) |
| 166 | 6 | HO$_2$C(CH$_2$)$_3$—N(Me)- | FAB-MS(Pos); 432(M$^+$ + 1) |
| 167 | 6 | 4-HO$_2$C-1-pipe | FAB-MS(Pos); 444(M$^+$ + 1) |
| 168 | 6 | 3-HO$_2$C-Ph-NH— | FAB-MS(Pos); 452(M$^+$ + 1) |
| 169 | 6 | 2-HO$_2$C-Ph-NH— | FAB-MS(Pos); 452(M$^+$ + 1) |
| 170 | 6 | 2-HO$_2$C-1-pyrr | FAB-MS(Pos); 430(M$^+$ + 1) |
| 171 | 6 | (S)-Ph-CH$_2$CH(CO$_2$H)—NH— | FAB-MS(Pos); 480(M$^+$ + 1) |
| 172 | 6 | (R)-Ph-CH$_2$CH(CO$_2$H)—NH— | FAB-MS(Pos); 480(M$^+$ + 1) |
| 173 | 6 | HOCH$_2$—CH(CO$_2$H)—NH— | FAB-MS(Pos); 420(M$^+$ + 1) |
| 174 | 8 | H$_2$NNH— | FAB-MS(Pos); 347(M$^+$ + 1), Sal:HCl |

TABLE 20-continued

Structure: 7-(cyclohexylamino)-6-fluoro-1-ethyl-4-oxo-1,4-dihydroquinoline-3-carbonyl-R

| Ex | Syn | R | Data |
|---|---|---|---|
| 175 | 9 | H₂NOC(CH₂)₄—NH— | FAB-MS(Pos); 431(M⁺ + 1) |
| 176 | 9 | H₂NOC(CH₂)₃—N(Me)- | FAB-MS(Pos); 431(M⁺ + 1) |
| 177 | 9 | 4-H₂NOC-Ph-NH— | FAB-MS(Pos); 451(M⁺ + 1) |

TABLE 21

Structure: 7-(cyclohexylamino)-6-fluoro-1-ethyl-4-oxo-1,4-dihydroquinoline-3-carbonyl-R

| Ex | Syn | R | Data |
|---|---|---|---|
| 178 | 2 | (HO)₂(O)P—O(CH₂)₂NH— | FAB-MS(Neg); 454(M⁺ − 1) |
| 179 | 2 | (3-(MeO₂CCH₂)-Ph)-NH— | FAB-MS(Pos); 480(M⁺ + 1) |
| 180 | 2 | (4-(EtO₂CCH₂)-Ph)-NH— | FAB-MS(Pos); 494(M⁺ + 1) |
| 181 | 6 | (3-(HO₂CCH₂)-Ph)-NH— | FAB-MS(Pos); 466(M⁺ + 1) |
| 182 | 6 | (4-(HO₂CCH₂)-Ph))-NH— | FAB-MS(Pos); 466(M⁺ + 1) |
| 183 | 1 | 3-EtO₂C-2-thiq | FAB-MS(Pos); 520(M⁺ + 1) |
| 184 | 6 | 3-HO₂C-2-thiq | FAB-MS(Pos); 492(M⁺ + 1) |
| 185 | 2 | (HO)₂(O)P—(CH₂)₃NH— | FAB-MS(Pos); 454(M⁺ + 1) |
| 186 | 2 | (S)-tBuO₂C(CH₂)₂CH(CONH₂)NH— | FAB-MS(Pos); 517(M⁺ + 1) |
| 187 | 5 | (S)-HO₂C(CH₂)₂CH(CONH₂)NH— | FAB-MS(Pos); 461(M⁺ + 1) |
| 188 | 2 | (EtO)₂(O)P—CH₂NH— | FAB-MS(Pos); 482(M⁺ + 1) |
| 189 | 7 | (HO)₂(O)P—CH₂NH— | ESI-MS(Pos); 426(M⁺ + 1) |

TABLE 22

Structure: 7-(cyclohexylamino)-6-fluoro-1-R-4-oxo-1,4-dihydroquinoline-3-carboxamide-N-CH₂-CO₂Et

| Ex | Syn | R | Data |
|---|---|---|---|
| 1 | 1 | cPen | FAB-MS(Pos); 458(M⁺ + 1) |
| 11 | 11 | HOCH₂CH(OH)CH₂— | FAB-MS(Pos); 464(M⁺ + 1) |
| 14 | 14 | 1-Me-3-pyrr | FAB-MS(Pos); 473(M⁺ + 1) |
| 16 | 16 | CF₃CH₂— | FAB-MS(Pos); 472(M⁺ + 1) |
| 17 | 17 | Boc-NH(CH₂)₂— | FAB-MS(Pos); 533(M⁺ + 1) |
| 19 | 19 | 1-pipe-(CH₂)₂— | FAB-MS(Pos.); 501(M⁺ + 1) |
| 20 | 20 | 1-Ac-3-pyrr | FAB-MS(Pos); 501(M⁺ + 1) |
| 21 | 21 | H | FAB-MS(Pos.); 390(M⁺ + 1) |
| 25 | 25 | 1-Bn-3-pyrr | FAB-MS(Pos); 549(M⁺ + 1) |
| 26 | 26 | (1RS,2SR,3RS,4SR)-2,3,4-triHO-cPen | FAB-MS(Pos); 506(M⁺ + 1) |
| 29 | 29 | 1-MeSO₂-3-pyrr | FAB-MS(Pos); 537(M⁺ + 1) |
| 31 | 31 | 3-pyrr | FAB-MS(Pos); 459(M⁺ + 1) |
| 190 | 1 | Me | FAB-MS(Pos); 404(M⁺ + 1) |
| 191 | 1 | iPr | FAB-MS(Pos); 432(M⁺ + 1) |
| 192 | 1 | Bn | FAB-MS(Pos); 480(M⁺ + 1) |
| 193 | 1 | 4-OMe-Bn | FAB-MS(Pos); 510(M⁺ + 1) |
| 194 | 1 | Ph | FAB-MS(Pos); 466(M⁺ + 1) |
| 195 | 1 | cHex | FAB-MS(Pos); 472(M⁺ + 1) |
| 196 | 1 | allyl | FAB-MS(Pos); 430(M⁺ + 1) |
| 197 | 1 | (1,3-dioxolan-2-yl)-CH₂— | FAB-MS(Pos); 476(M⁺ + 1) |
| 198 | 1 | 2-THP—O—(CH₂)₂— | FAB-MS(Pos); 518(M⁺ + 1) |
| 199 | 1 | (R)-3-THF | FAB-MS(Pos); 460(M⁺ + 1) |
| 200 | 4 | HO—(CH₂)₂— | FAB-MS(Pos); 434(M⁺ + 1) |
| 201 | 1 | (S)-3-THF | FAB-MS(Pos); 460(M⁺ + 1) |
| 202 | 1 | cPr | FAB-MS(Pos); 430(M⁺ + 1) |
| 203 | 1 | cBu | FAB-MS(Pos); 444(M⁺ + 1) |
| 204 | 1 | tBu | FAB-MS(Pos); 446(M⁺ + 1) |
| 205 | 1 | 3-THF | FAB-MS(Pos); 460(M⁺ + 1) |
| 206 | 1 | MeO—(CH₂)₂— | FAB-MS(Pos); 448(M⁺ + 1) |
| 207 | 1 | 1-Boc-3-pyrr | FAB-MS(Pos); 559(M⁺ + 1) |
| 208 | 1 | sBu | FAB-MS(Pos); 446(M⁺ + 1) |
| 209 | 1 | (Et)₂CH— | FAB-MS(Pos); 460(M⁺ + 1) |
| 210 | 8 | 3-pyrr | FAB-MS(Pos); 459(M⁺ + 1), Sal:HCl |
| 211 | 1 | iPrCH(Me)- | FAB-MS(Pos); 460(M⁺ + 1) |
| 212 | 1 | iBuCH(Me)- | FAB-MS(Pos); 474(M⁺ + 1) |
| 213 | 1 | tBuCH(Me)- | FAB-MS(Pos); 474(M⁺ + 1) |
| 214 | 1 | iBu | FAB-MS(Pos); 446(M⁺ + 1) |
| 215 | 1 | oxetan-3-yl | FAB-MS(Pos); 446(M⁺ + 1) |
| 216 | 1 | 4-THP | FAB-MS(Pos); 474(M⁺ + 1) |
| 217 | 1 | 1-Boc-4-pipe | FAB-MS(Pos); 573(M⁺ + 1) |

TABLE 23

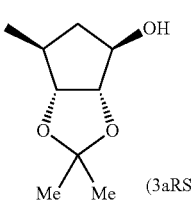

| Ex | Syn | R | Data |
|---|---|---|---|
| 218 | 8 | 4-pipe | FAB-MS(Pos); 473(M$^+$ + 1), Sal: HCl |
| 219 | 14 | 1-Me-4-pipe | FAB-MS(Pos); 487(M$^+$ + 1) |
| 220 | 16 | 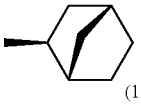 (3aRS,4SR,6RS,6aSR) | FAB-MS(Pos); 546(M$^+$ + 1) |
| 221 | 1 | 1-Me-azetidin-3-yl | FAB-MS(Pos); 459(M$^+$ + 1) Sal: HCl |
| 222 | 16 | (1RS,2RS,4SR) | FAB-MS(Pos); 484(M$^+$ + 1) |
| 223 | 16 | nPrCH(Me)- | FAB-MS(Pos); 460(M$^+$ + 1) |
| 224 | 16 | (nPr)$_2$CH— | FAB-MS(Pos); 488(M$^+$ + 1) |
| 225 | 16 | nPrCH(Et)- | FAB-MS(Pos); 474(M$^+$ + 1) |
| 226 | 16 |  (1RS,2SR,4SR) | FAB-MS(Pos); 484(M$^+$ + 1) |
| 227 | 16 | CF$_3$CH(Me)- | ESI-MS(Pos); 486(M$^+$ + 1) |
| 228 | 16 | cyclopent-3-en-1-yl | FAB-MS(Pos); 456(M$^+$ + 1) |
| 229 | 1 | MeHNOC-CH$_2$— | FAB-MS(Pos.); 461(M$^+$ + 1) |
| 230 | 1 | (4-Me-1-pipa)-CO—CH$_2$— | FAB-MS(Pos.); 530(M$^+$ + 1) |
| 231 | 1 | (4-mor)-CO—CH$_2$— | FAB-MS(Pos.); 517(M$^+$ + 1) |
| 232 | 19 | 1-pyrr-(CH$_2$)$_2$— | FAB-MS(Pos.); 487(M$^+$ + 1) |
| 233 | 14 | Me$_2$N(CH$_2$)$_2$— | FAB-MS(Pos.); 461(M$^+$ + 1) |
| 234 | 20 | AcNH(CH$_2$)$_2$— | FAB-MS(Pos.); 475(M$^+$ + 1) |
| 235 | 29 | MeSO$_2$NH(CH$_2$)$_2$— | FAB-MS(Pos.); 511(M$^+$ + 1) |
| 236 | 1 | 2,2-diMe-1,3-dioxan-5-yl | FAB-MS(Pos.); 504(M$^+$ + 1) |
| 237 | 22 | (HOCH$_2$)$_2$CH— | FAB-MS(Pos.); 464(M$^+$ + 1) |
| 238 | 1 | (MeOCH$_2$)$_2$CH— | FAB-MS(Pos.); 492(M$^+$ + 1) |
| 239 | 1 | (AcNHCH$_2$)$_2$CH— | FAB-MS(Pos.); 546(M$^+$ + 1) |
| 240 | 16 | AcNH(CH$_2$)$_3$— | ESI-MS(Pos); 489(M$^+$ + 1) |
| 241 | 16 | (FCH$_2$)$_2$CH— | FAB-MS(Pos); 468(M$^+$ + 1) |
| 242 | 16 | FCH$_2$CH(Me)- | FAB-MS(Pos); 450(M$^+$ + 1) |
| 243 | 16 | isopropenyl | FAB-MS(Pos); 430(M$^+$ + 1) |
| 244 | 16 | H$_2$C=C(CH$_2$F)— | FAB-MS(Pos); 448(M$^+$ + 1) |
| 245 | 16 | MeOCH$_2$CH(Me)- | FAB-MS(Pos); 462(M$^+$ + 1) |
| 246 | 16 | 4,4-dimethyl-cHex | FAB-MS(Pos); 500(M$^+$ + 1) |
| 247 | 16 | AcNHCH$_2$CH(Me)- | FAB-MS(Pos); 489(M$^+$ + 1) |
| 248 | 16 | AcN(Me)(CH$_2$)$_2$— | FAB-MS(Pos); 489(M$^+$ + 1) |
| 249 | 16 | AcN(Me)CH$_2$CH(Me)- | FAB-MS(Pos); 503(M$^+$ + 1) |
| 250 | 1 | 3-methylcyclopent-3-en-1yl | FAB-MS(Pos); 470(M$^+$ + 1) |
| 251 | 16 | 2-THP-OCH$_2$CH(Me)- | ESI-MS(Pos); 532(M$^+$ + 1) |
| 252 | 4 | HOCH$_2$CH(Me)- | FAB-MS(Pos); 448(M$^+$ + 1) |
| 253 | 16 | 2,2-diethyl-1,3-dioxan-5-yl | FAB-MS(Pos); 532(M$^+$ + 1) |

TABLE 24

| Ex | Syn | R | Data |
|---|---|---|---|
| 6 | 6 | cPen | FAB-MS(Pos); 430(M$^+$ + 1) |
| 30 | 30 | H$_2$N(CH$_2$)$_2$— | FAB-MS(Pos); 405(M$^+$ + 1) |
| 32 | 32 | (FCH$_2$)$_2$CH— | FAB-MS(Pos); 440(M$^+$ + 1) |
| 254 | 6 | Me | FAB-MS(Pos); 376(M$^+$ + 1) |
| 255 | 6 | iPr | FAB-MS(Pos); 404(M$^+$ + 1) |
| 256 | 6 | Bn | FAB-MS(Pos); 452(M$^+$ + 1) |
| 257 | 6 | 4-MeO-Bn | FAB-MS(Pos); 482(M$^+$ + 1) |
| 258 | 6 | Ph | FAB-MS(Pos); 438(M$^+$ + 1) |
| 259 | 6 | cHex | FAB-MS(Pos); 444(M$^+$ + 1) |
| 260 | 6 | Allyl | FAB-MS(Pos); 402(M$^+$ + 1) |
| 261 | 6 | HOCH$_2$CH(OH)CH$_2$— | FAB-MS(Pos); 436(M$^+$ + 1) |
| 262 | 6 | (1,3-dioxolan-2-yl)-CH$_2$— | FAB-MS(Pos); 448(M$^+$ + 1) |
| 263 | 6 | 2-THP-O-(CH$_2$)$_2$— | FAB-MS(Pos); 490(M$^+$ + 1) |
| 264 | 6 | (R)-3-THF | FAB-MS(Pos); 432(M$^+$ + 1) |
| 265 | 6 | HO-(CH$_2$)$_2$— | FAB-MS(Pos); 406(M$^+$ + 1) |
| 266 | 6 | (S)-3-THF | FAB-MS(Pos); 432(M$^+$ + 1) |
| 267 | 6 | cPr | FAB-MS(Pos); 402(M$^+$ + 1) |
| 268 | 6 | cBu | FAB-MS(Pos); 416(M$^+$ + 1) |
| 269 | 6 | tBu | FAB-MS(Pos); 418(M$^+$ + 1) |
| 270 | 6 | 3-THF | FAB-MS(Pos); 432(M$^+$ + 1) |
| 271 | 6 | MeO(CH$_2$)$_2$— | FAB-MS(Pos); 420(M$^+$ + 1) |
| 272 | 6 | 1-Boc-3-pyrr | FAB-MS(Pos); 531(M$^+$ + 1) |
| 273 | 6 | sBu | FAB-MS(Pos); 418(M$^+$ + 1) |
| 274 | 6 | (Et)$_2$CH— | FAB-MS(Pos); 432(M$^+$ + 1) |
| 275 | 8 | 3-pyrr | ESI-MS(Pos); 431(M$^+$ + 1), Sal: HCl |
| 276 | 6 | iPrCH(Me)- | FAB-MS(Pos); 432(M$^+$ + 1) |
| 277 | 6 | iBuCH(Me)- | FAB-MS(Pos); 446(M$^+$ + 1) |
| 278 | 6 | tBuCH(Me)- | FAB-MS(Pos); 446(M$^+$ + 1) |
| 279 | 6 | 1-Me-3-pyrr | ESI-MS(Pos); 445(M$^+$ + 1), Sal: HCl |
| 280 | 6 | iBu | FAB-MS(Pos); 418(M$^+$ + 1) |
| 281 | 6 | oxetan-3-yl | FAB-MS(Pos); 418(M$^+$ + 1) |
| 282 | 6 | 4-THP | FAB-MS(Pos); 446(M$^+$ + 1) |
| 283 | 6 | 1-Ac-3-pyrr | FAB-MS(Pos); 473(M$^+$ + 1) |
| 284 | 6 | 1-MeSO$_2$-3-pyrr | FAB-MS(Pos); 509(M$^+$ + 1) |
| 285 | 6 | 1-Bn-3-pyrr | FAB-MS(Pos); 521(M$^+$ + 1) |
| 286 | 6 | 1-Me-4-pipe | FAB-MS(Pos); 459(M$^+$ + 1) |

TABLE 25

| Ex | Syn | R | Data |
|---|---|---|---|
| 287 | 6 | 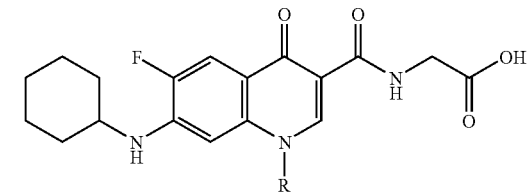 (3aRS,4SR,6RS,6aSR) | FAB-MS(Pos); 518(M$^+$ + 1) |
| 288 | 6 | (1RS,2SR,3RS,4SR)-2,3,4-triHO-cPen | FAB-MS(Pos); 478(M$^+$ + 1) |
| 289 | 6 | 1-Me-azetidin-3-yl | FAB-MS(Pos); 431(M$^+$ + 1) |
| 290 | 6 | (1RS,2RS,4SR) | FAB-MS(Pos); 456(M$^+$ + 1) |
| 291 | 6 | nPrCH(Me)- | FAB-MS(Pos); 432(M$^+$ + 1) |
| 292 | 6 | (nPr)$_2$CH— | FAB-MS(Pos); 460(M$^+$ + 1) |
| 293 | 6 | nPrCH(Et)- | FAB-MS(Pos); 446(M$^+$ + 1) |
| 294 | 6 | CF$_3$CH$_2$— | FAB-MS(Pos); 444(M$^+$ + 1) |
| 295 | 6 | (1RS,2SR,4SR) | FAB-MS(Pos); 456(M$^+$ + 1) |

TABLE 25-continued

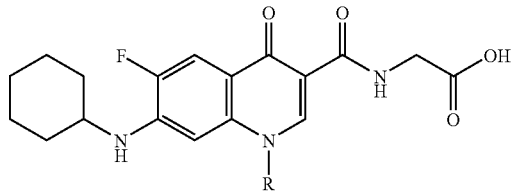

| Ex | Syn | R | Data |
|---|---|---|---|
| 296 | 6 | CF$_3$CH(Me)- | FAB-MS(Pos); 458(M$^+$ + 1) |
| 297 | 6 | cyclopent-3-en-1-yl | FAB-MS(Pos); 428(M$^+$ + 1) |
| 298 | 6 | 1-pipe-(CH$_2$)$_2$— | ESI-MS(Pos.); 473(M$^+$ + 1) |
| 299 | 6 | MeHNOC—CH$_2$— | FAB-MS(Pos.); 433(M$^+$ + 1) |
| 300 | 6 | (4-Me-1-pipa)-CO—CH$_2$— | FAB-MS(Pos.); 502(M$^+$ + 1) |
| 301 | 6 | (4-mor)-(CH$_2$)$_2$— | FAB-MS(Pos.); 475(M$^+$ + 1) |
| 302 | 6 | 1-pyrr-(CH$_2$)$_2$— | ESI-MS(Pos.); 459(M$^+$ + 1) |
| 303 | 6 | Me$_2$N(CH$_2$)$_2$— | FAB-MS(Pos.); 433(M$^+$ + 1) |
| 304 | 6 | AcNH(CH$_2$)$_2$— | FAB-MS(Pos.); 447(M$^+$ + 1) |
| 305 | 6 | MeSO$_2$NH(CH$_2$)$_2$— | FAB-MS(Pos.); 483(M$^+$ + 1) |
| 306 | 6 | 2,2-diMe-1,3-dioxan-5-yl | FAB-MS(Pos.); 476(M$^+$ + 1) |
| 307 | 22 | (HOCH$_2$)$_2$CH— | FAB-MS(Pos.); 436(M$^+$ + 1) |
| 308 | 6 | H | FAB-MS(Pos.); 362(M$^+$ + 1) |
| 309 | 6 | (MeOCH$_2$)$_2$CH— | FAB-MS(Pos.); 464(M$^+$ + 1) |
| 310 | 6 | (AcNHCH$_2$)$_2$CH— | FAB-MS(Pos.); 518(M$^+$ + 1) |
| 311 | 6 | AcNH(CH$_2$)$_3$— | FAB-MS(Pos); 461(M$^+$ + 1) |
| 312 | 6 | FCH$_2$CH(Me)- | FAB-MS(Pos); 422(M$^+$ + 1) |
| 313 | 6 | isopropenyl | FAB-MS(Pos); 402(M$^+$ + 1) |
| 314 | 6 | H$_2$C=C(CH$_2$F)— | FAB-MS(Pos); 420(M$^+$ + 1) |
| 315 | 6 | MeOCH$_2$CH(Me)- | FAB-MS(Pos); 434(M$^+$ + 1) |
| 316 | 6 | 4,4-dimethyl-cHex | FAB-MS(Pos); 472(M$^+$ + 1) |
| 317 | 6 | AcNHCH$_2$CH(Me)- | ESI-MS(Pos); 461(M$^+$ + 1) |
| 318 | 6 | AcN(Me)(CH$_2$)$_2$— | FAB-MS(Pos); 461(M$^+$ + 1) |
| 319 | 6 | AcN(Me)CH$_2$CH(Me)- | FAB-MS(Pos); 475(M$^+$ + 1) |
| 320 | 6 | 3-methylcyclopent-3-en-1yl | FAB-MS(Pos); 442(M$^+$ + 1) |
| 321 | 6 | HOCH$_2$CH(Me)- | FAB-MS(Pos); 420(M$^+$ + 1) |
| 322 | 6 | 2,2-diethyl-1,3-dioxan-5-yl | FAB-MS(Pos); 504(M$^+$ + 1) |

TABLE 26

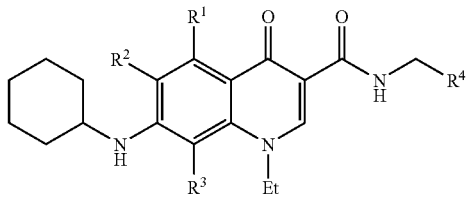

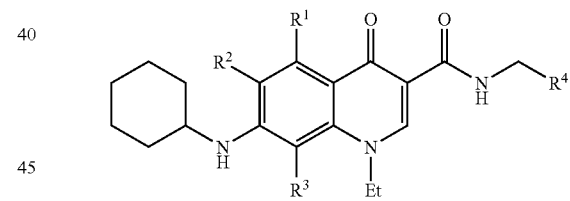

| Ex | Syn | R$^1$ | R$^2$ | R$^3$ | R$^4$ | Data |
|---|---|---|---|---|---|---|
| 34 | 34 | NHAc | F | H | CO$_2$Et | FAB-MS(Pos); 475(M$^+$ + 1) |
| 323 | 1 | H | H | H | CO$_2$Et | FAB-MS(Pos); 400(M$^+$ + 1) |
| 324 | 1 | H | Br | H | CO$_2$Et | FAB-MS(Pos); 478, 480(M$^+$ + 1) |
| 325 | 6 | H | H | H | CO$_2$H | FAB-MS(Pos); 372(M$^+$ + 1) |
| 326 | 6 | H | Br | H | CO$_2$H | FAB-MS(Pos); 450, 452(M$^+$ + 1) |
| 327 | 1 | H | Me | H | CO$_2$Et | FAB-MS(Pos); 414(M$^+$ + 1) |
| 328 | 6 | H | Me | H | CO$_2$H | FAB-MS(Pos); 386(M$^+$ + 1) |
| 329 | 1 | H | F | Cl | CO$_2$Et | FAB-MS(Pos); 452(M$^+$ + 1) |
| 330 | 6 | H | F | Cl | CO$_2$H | FAB-MS(Pos); 424(M$^+$ + 1) |
| 331 | 1 | H | Cl | H | CO$_2$Et | FAB-MS(Pos); 434(M$^+$ + 1) |
| 332 | 6 | H | Cl | H | CO$_2$H | FAB-MS(Pos); 406(M$^+$ + 1) |
| 333 | 1 | H | F | F | CO$_2$Et | FAB-MS(Pos); 436(M$^+$ + 1) |
| 334 | 6 | H | F | F | CO$_2$H | FAB-MS(Pos); 408(M$^+$ + 1) |
| 335 | 16 | F | F | H | CO$_2$Et | FAB-MS(Pos); 436(M$^+$ + 1) |
| 336 | 6 | F | F | H | CO$_2$H | FAB-MS(Pos); 408(M$^+$ + 1) |
| 337 | 16 | OMe | F | H | CO$_2$Et | ESI-MS(Pos); 448(M$^+$ + 1) |
| 338 | 6 | OMe | F | H | CO$_2$H | FAB-MS(Pos); 420(M$^+$ + 1) |
| 339 | 16 | NH$_2$ | F | H | CO$_2$Et | ESI-MS(Pos); 433(M$^+$ + 1) |
| 340 | 6 | NH$_2$ | F | H | CO$_2$H | FAB-MS(Pos); 405(M$^+$ + 1) |
| 341 | 16 | NHMe | F | H | CO$_2$Et | FAB-MS(Pos); 447(M$^+$ + 1) |
| 342 | 6 | NHMe | F | H | CO$_2$H | FAB-MS(Pos); 419(M$^+$ + 1) |

TABLE 26-continued

Structure: quinoline core with R1, R2, R3 substituents, cyclohexyl-NH, N-Et, and carboxamide-CH2-R4

| Ex | Syn | R¹ | R² | R³ | R⁴ | Data |
|---|---|---|---|---|---|---|
| 343 | 16 | NH(cHex) | F | H | CO₂Et | FAB-MS(Pos); 515(M⁺ + 1) |
| 344 | 6 | NH(cHex) | F | H | CO₂H | FAB-MS(Pos); 487(M⁺ + 1) |
| 345 | 6 | NHAc | F | H | CO₂H | FAB-MS(Pos); 447(M⁺ + 1) |
| 346 | 16 | N(Me)Ac | F | H | CO₂Et | FAB-MS(Pos); 531(M⁺ + 1) |
| 347 | 6 | N(Me)Ac | F | H | CO₂H | FAB-MS(Pos); 503(M⁺ + 1) |

TABLE 27

Structure: quinoline core with cyclohexyl-NH, N-CH(Me)(CH2Me) [pentan-3-yl], R1, R2, R3 substituents, and carboxamide-CH2-R4

| Ex | Syn | R¹ | R² | R³ | R⁴ | Data |
|---|---|---|---|---|---|---|
| 33 | 33 | NMe₂ | F | H | CO₂Et | FAB-MS(Pos); 503(M⁺ + 1) |
| 348 | 16 | F | F | H | CO₂Et | FAB-MS(Pos); 478(M⁺ + 1) |
| 349 | 6 | F | F | H | CO₂H | FAB-MS(Pos); 450(M⁺ + 1) |
| 350 | 6 | NMe₂ | F | H | CO₂H | FAB-MS(Pos); 475(M⁺ + 1) |
| 351 | 33 | 1-pyrr | F | H | CO₂Et | FAB-MS(Pos); 529(M⁺ + 1) |
| 352 | 6 | 1-pyrr | F | H | CO₂H | FAB-MS(Pos); 501(M⁺ + 1) |
| 353 | 16 | OBn | F | H | CO₂Et | ESI-MS(Pos); 566(M⁺ + 1) |
| 354 | 18 | OH | F | H | CO₂Et | FAB-MS(Pos); 476(M⁺ + 1) |
| 355 | 6 | OH | F | H | CO₂H | FAB-MS(Pos); 448(M⁺ + 1) |

TABLE 28

Structure: 6-F-7-(R¹NH)-1-Et-4-oxoquinoline-3-carboxamide-CH2-R2

| Ex | Syn | R¹ | R² | Data |
|---|---|---|---|---|
| 8 | 8 | 4-pipe | CO₂H | FAB-MS(Pos); 391(M⁺ + 1), Sal: HCl |
| 13 | 13 | cHexCH₂— | CO₂H | FAB-MS(Pos); 404(M⁺ + 1) |
| 356 | 1 | iPr | CO₂Et | FAB-MS(Pos); 378(M⁺ + 1) |
| 357 | 1 | tBu | CO₂Et | FAB-MS(Pos); 392(M⁺ + 1) |
| 358 | 1 | 4-THP | CO₂Et | FAB-MS(Pos); 420(M⁺ + 1) |
| 359 | 1 | cPen | CO₂Et | FAB-MS(Pos); 404(M⁺ + 1) |
| 360 | 1 | 1-Boc-4-pipe | CO₂Et | FAB-MS(Pos); 519(M⁺ + 1) |
| 361 | 1 | Ph | CO₂Et | FAB-MS(Pos); 412(M⁺ + 1) |
| 362 | 1 | cHep | CO₂Et | FAB-MS(Pos); 432(M⁺ + 1) |

TABLE 28-continued

| Ex | Syn | R¹ | R² | Data |
|---|---|---|---|---|
| 363 | 1 | cOct | CO₂Et | FAB-MS(Pos); 446(M⁺ + 1) |
| 364 | 1 | 1-Me-cHex | CO₂Et | FAB-MS(Pos); 432(M⁺ + 1) |
| 365 | 1 | 4-THSP | CO₂Et | FAB-MS(Pos); 436(M⁺ + 1) |
| 366 | 14 | 1-Me-4-pipe | CO₂Et | FAB-MS(Pos); 433(M⁺ + 1) |
| 367 | 1 | 4-Me-cHex | CO₂Et | FAB-MS(Pos); 432(M⁺ + 1) |
| 368 | 1 | 4-Me-cHex | CO₂Et | FAB-MS(Pos); 432(M⁺ + 1) |
| 369 | 1 | 4,4-diF-cHex | CO₂Et | FAB-MS(Pos); 454(M⁺ + 1) |
| 370 | 6 | iPr | CO₂H | FAB-MS(Pos); 350(M⁺ + 1) |
| 371 | 6 | tBu | CO₂H | FAB-MS(Pos); 364(M⁺ + 1) |
| 372 | 6 | 4-THP | CO₂H | FAB-MS(Pos); 392(M⁺ + 1) |
| 373 | 6 | cPen | CO₂H | FAB-MS(Pos); 376(M⁺ + 1) |
| 374 | 6 | 1-Boc-4-pipe | CO₂H | FAB-MS(Pos); 491(M⁺ + 1) |

TABLE 29

Structure: 6-F-7-(R¹NH)-1-Et-4-oxoquinoline-3-carboxamide-CH2-R2

| Ex | Syn | R¹ | R² | Data |
|---|---|---|---|---|
| 375 | 6 | Ph | CO₂H | FAB-MS(Pos); 384(M⁺ + 1) |
| 376 | 6 | cHep | CO₂H | FAB-MS(Pos); 404(M⁺ + 1) |
| 377 | 6 | cOct | CO₂H | FAB-MS(Pos); 418(M⁺ + 1) |
| 378 | 6 | 1-Me-cHex | CO₂H | FAB-MS(Pos); 404(M⁺ + 1) |
| 379 | 6 | 4-THSP | CO₂H | FAB-MS(Pos); 408(M⁺ + 1) |
| 380 | 6 | 1-Me-4-pipe | CO₂H | FAB-MS(Pos); 405(M⁺ + 1) |
| 381 | 6 | 4-Me-cHex | CO₂H | FAB-MS(Pos); 404(M⁺ + 1) |
| 382 | 6 | 4-Me-cHex | CO₂H | FAB-MS(Pos); 404(M⁺ + 1) |
| 383 | 6 | 4,4-diF-cHex | CO₂H | FAB-MS(Pos); 426(M⁺ + 1) |

TABLE 30

Structure: 6-F-7-(R¹NH)-1-cyclopentyl-4-oxoquinoline-3-carboxamide-CH2-R2

| Ex | Syn | R1 | R2 | Data |
|---|---|---|---|---|
| 384 | 1 | 4-THSP | CO₂Et | FAB-MS(Pos); 476(M⁺ + 1) |
| 385 | 6 | 4-THSP | CO₂H | FAB-MS(Pos); 448(M⁺ + 1) |
| 386 | 1 | 4,4-diF-cHex | CO₂Et | FAB-MS(Pos); 494(M⁺ + 1) |
| 387 | 6 | 4,4-diF-cHex | CO₂H | FAB-MS(Pos); 466(M⁺ + 1) |
| 388 | 1 | 3-THP | CO₂Et | FAB-MS(Pos); 460(M⁺ + 1) |
| 389 | 6 | 3-THP | CO₂H | FAB-MS(Pos); 432(M⁺ + 1) |

TABLE 31

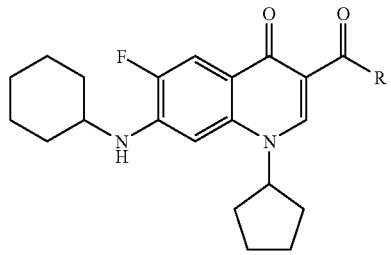

| Ex | Syn | R | Data |
|---|---|---|---|
| 15 | 15 | (HO)$_2$(O)P—(CH$_2$)$_2$NH— | FAB-MS(Pos); 480(M$^+$ + 1), Sal: HBr |
| 27 | 27 | (tBuCO$_2$CH$_2$O)$_2$(O)P—(CH$_2$)$_2$NH— | FAB-MS(Pos); 708(M$^+$ + 1) |
| 390 | 16 | (HO—CH$_2$CH$_2$)$_2$N— | FAB-MS(Pos); 460(M$^+$ + 1) |
| 391 | 16 | 3-HO-1-pipe | FAB-MS(Pos); 456(M$^+$ + 1) |
| 392 | 16 | HO—(CH$_2$)$_3$NH— | FAB-MS(Pos); 430(M$^+$ + 1) |
| 393 | 16 | 3-(HO—CH$_2$)-1-pipe | FAB-MS(Pos); 470(M$^+$ + 1) |
| 394 | 16 | 2-(HOCH$_2$)-1-pipe | FAB-MS(Pos); 470(M$^+$ + 1) |
| 395 | 16 | HO—CH$_2$CHOHCH$_2$NMe- | FAB-MS(Pos); 460(M$^+$ + 1) |
| 396 | 16 | 3-HO-1-pyrr | FAB-MS(Pos); 442(M$^+$ + 1) |
| 397 | 16 | (S)-3-EtO$_2$C-2-thiq | FAB-MS(Pos); 560(M$^+$ + 1) |
| 398 | 16 | (R)-3-EtO$_2$C-2-thiq | FAB-MS(Pos); 560(M$^+$ + 1) |
| 399 | 6 | (S)-3-HO$_2$C-2-thiq | FAB-MS(Pos); 532(M$^+$ + 1) |
| 400 | 6 | (R)-3-HO$_2$C-2-thiq | FAB-MS(Pos); 532(M$^+$ + 1) |
| 401 | 16 | EtO$_2$C-CH$_2$NMe- | FAB-MS(Pos); 472(M$^+$ + 1) |
| 402 | 16 | 2-EtO$_2$C-1-pyrr | FAB-MS(Pos); 498(M$^+$ + 1) |
| 403 | 6 | HO$_2$C-CH$_2$NMe- | FAB-MS(Pos); 444(M$^+$ + 1) |
| 404 | 6 | 2-HO$_2$C-1-pyrr | FAB-MS(Pos); 470(M$^+$ + 1) |
| 405 | 1 | (S)-EtO$_2$C-CHOH(CH$_2$)$_2$NH— | FAB-MS(Pos); 502(M$^+$ + 1) |
| 406 | 6 | (S)-HO$_2$C-CHOH(CH$_2$)$_2$NH— | FAB-MS(Pos); 474(M$^+$ + 1) |
| 407 | 16 | 4-HO-1-pipe | FAB-MS(Pos); 456(M$^+$ + 1) |
| 408 | 16 | HO-(CH$_2$)$_2$NMe- | FAB-MS(Pos); 430(M$^+$ + 1) |
| 409 | 16 | HO-(CH$_2$)$_2$NBn- | FAB-MS(Pos); 506(M$^+$ + 1) |
| 410 | 1 | 2-Py-(CH$_2$)$_2$NH— | FAB-MS(Pos); 477(M$^+$ + 1) |
| 411 | 1 | ![structure] (3aRS,4SR,6RS,6aSR) | FAB-MS(Pos); 528(M$^+$ + 1) |
| 412 | 1 | (EtO)$_2$(O)P—(CH$_2$)$_2$NH— | FAB-MS(Pos); 536(M$^+$ + 1) |
| 413 | 4 | (1RS,2SR,3RS,4SR)-2,3,4-triHO-cPen | FAB-MS(Pos); 488(M$^+$ + 1) |
| 414 | 1 | (S)-tBuO$_2$C-CH$_2$CH(CO$_2$tBu)-NH— | FAB-MS(Pos); 600(M$^+$ + 1) |
| 415 | 1 | 3-EtO$_2$C-2-thiq | FAB-MS(Pos); 560(M$^+$ + 1) |
| 416 | 1 | (HO)$_2$(O)P—O(CH$_2$)$_2$NH— | FAB-MS(Neg); 494(M$^+$ − 1) |
| 417 | 5 | (S)-HO$_2$C-CH$_2$CH(CO$_2$H)—NH— | FAB-MS(Pos); 488(M$^+$ + 1) |

TABLE 32

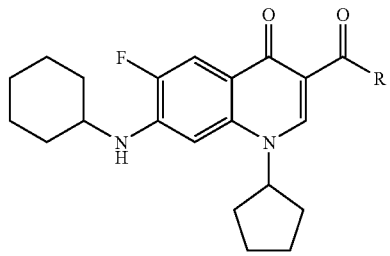

| Ex | Syn | R | Data |
|---|---|---|---|
| 418 | 1 | (3aRS,4SR,6RS,6aSR) structure with NHMe, O-CH2CH2-OH, acetonide Me,Me | FAB-MS(Pos); 572(M+ + 1) |
| 419 | 6 | 3-HO2C-2-thiq | FAB-MS(Pos); 532(M+ + 1) |
| 420 | 4 | (1RS,2SR,3SR,4SR)-2,3-diHO-4-(HO(CH2)2O)-cPen | FAB-MS(Pos); 532(M+ + 1) |
| 421 | 1 | (2-HO-Ph)-NH— | FAB-MS(Pos); 464(M+ + 1) |
| 422 | 1 | (3-HO-Ph)-NH— | FAB-MS(Pos); 464(M+ + 1) |
| 423 | 1 | (4-HO-Ph)-NH— | FAB-MS(Pos); 464(M+ + 1) |
| 424 | 1 | (S)-tBuO2C-(CH2)2CH(CO2tBu)-NH— | FAB-MS(Pos); 614(M+ + 1) |
| 425 | 5 | (S)-HO2C—(CH2)2CH(CO2H)—NH— | FAB-MS(Pos); 502(M+ + 1) |
| 426 | 1 | (EtO)2(O)P—CH(CH2cHex)CH2NH— | FAB-MS(Pos); 632(M+ + 1) |
| 427 | 15 | (HO)2(O)P—CH(CH2cHex)CH2NH— | FAB-MS(Pos); 576(M+ + 1) Sal: HBr |
| 428 | 1 | (EtO)2(O)P—CH(Bn)-CH2NH— | FAB-MS(Pos); 626(M+ + 1) |
| 429 | 7 | (HO)2(O)P-CH(Bn)-CH2NH— | FAB-MS(Pos); 570(M+ + 1) |
| 430 | 16 | EtO2C—CH2NBn- | FAB-MS(Pos); 548(M+ + 1) |
| 431 | 6 | HO2C—CH2NBn- | FAB-MS(Pos); 520(M+ + 1) |
| 432 | 16 | EtO2C—CH(Bn)NMe- | FAB-MS(Pos); 562(M+ + 1) |
| 433 | 6 | HO2C—CH(Bn)NMe- | FAB-MS(Pos); 534(M+ + 1) |
| 434 | 16 | (BnO)2(O)P—(CH2)2NH— | FAB-MS(Pos); 660(M+ + 1) |
| 435 | 24 | (BnO)(HO)(O)P—(CH2)2NH— | FAB-MS(Pos); 570(M+ + 1) |
| 436 | 16 | EtO2C—CH(CH2OH)NH— | FAB-MS(Pos); 488(M+ + 1) |
| 437 | 6 | HO2C—CH(CH2OH)NH— | FAB-MS(Pos); 460(M+ + 1) |
| 438 | 16 | (S)-MeO2C—CH2CH(CO2tBu)-NH— | FAB-MS(Pos); 558(M+ + 1) |
| 439 | 16 | (S)-MeO2C—(CH2)2CH(CO2tBu)-NH— | FAB-MS(Pos); 572(M+ + 1) |
| 440 | 5 | (S)-MeO2C—CH2CH(CO2H)—NH— | FAB-MS(Pos); 502(M+ + 1) |
| 441 | 5 | (S)-MeO2C—(CH2)2CH(CO2H)—NH— | FAB-MS(Pos); 516(M+ + 1) |
| 442 | 18 | (tBuCO2CH2O)(HO)(O)P—(CH2)2NH— | FAB-MS(Pos); 594(M+ + 1) |
| 443 | 27 | (tBuCO2CH2O)(BnO)(O)P—(CH2)2NH— | FAB-MS(Pos); 684(M+ + 1) |
| 444 | 16 | (S)-tBuO2C—(CH2)2CH(CO2Me)-NH— | FAB-MS(Pos); 572(M+ + 1) |
| 445 | 5 | (S)-HO2C—(CH2)2CH(CO2Me)-NH— | FAB-MS(Pos); 516(M+ + 1) |
| 446 | 16 | (S)-tBuO2C—CH2CH(CO2Me)-NH— | FAB-MS(Pos); 558(M+ + 1) |
| 447 | 5 | (S)-HO2C—CH2CH(CO2Me)-NH— | FAB-MS(Pos); 502(M+ + 1) |
| 448 | 1 | 4-EtO2C-1-pipe | FAB-MS(Pos); 512(M+ + 1) |
| 449 | 6 | 4-HO2C-1-pipe | FAB-MS(Pos); 484(M+ + 1) |
| 450 | 1 | 2-thiq | FAB-MS(Pos); 488(M+ + 1) |
| 451 | 1 | HO—(CH2)2NH— | FAB-MS(Pos); 416(M+ + 1) |

TABLE 33

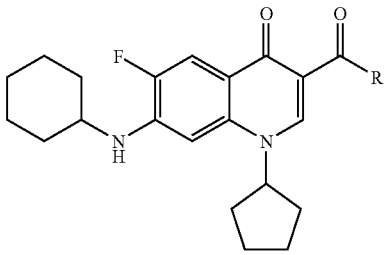

| Ex | Syn | R | Data |
|---|---|---|---|
| 452 | 1 | EtO$_2$C—(CH$_2$)$_2$NH— | FAB-MS(Pos); 472(M$^+$ + 1) |
| 453 | 16 | 3-EtO$_2$C-1-pipe | ESI-MS(Pos); 512(M$^+$ + 1) |
| 454 | 6 | 3-HO$_2$C-1-pipe | FAB-MS(Pos); 484(M$^+$ + 1) |
| 455 | 6 | HO$_2$C—(CH$_2$)$_2$NH— | FAB-MS(Pos); 444(M$^+$ + 1) |
| 456 | 16 | 2-EtO$_2$C-1-pipe | FAB-MS(Pos); 512(M$^+$ + 1) |
| 457 | 16 | BocNHNH— | FAB-MS(Pos); 487(M$^+$ + 1) |
| 458 | 16 | H$_2$N— | ESI-MS(Pos); 372(M$^+$ + 1) |
| 459 | 16 | MeHN— | FAB-MS(Pos); 386(M$^+$ + 1) |
| 460 | 16 | Me$_2$N— | FAB-MS(Pos); 400(M$^+$ + 1) |
| 461 | 16 | 3-H$_2$NOC-2-thiq | FAB-ESI(Pos); 531(M$^+$ + 1) |
| 462 | 8 | H$_2$N—NH— | FAB-MS(Pos); 387(M$^+$ + 1) |
| 463 | 6 | 2-HO$_2$C-1-pipe | FAB-MS(Pos); 484(M$^+$ + 1) |
| 464 | 16 | EtO$_2$C—(CH$_2$)$_3$NH— | FAB-MS(Pos); 486(M$^+$ + 1) |
| 465 | 16 | Boc-NH(CH$_2$)$_2$NH— | ESI-MS(Pos); 515(M$^+$ + 1) |
| 466 | 16 | Me$_2$N—(CH$_2$)$_2$NH— | FAB-MS(Pos); 443(M$^+$ + 1) |
| 467 | 6 | HO$_2$C—(CH$_2$)$_3$NH— | FAB-MS(Pos); 458(M$^+$ + 1) |
| 468 | 16 | (S)-EtO$_2$C—(CH$_2$)$_2$CH(CO$_2$Et)-NH— | FAB-MS(Pos); 558(M$^+$ + 1) |
| 469 | 8 | H$_2$N—(CH$_2$)$_2$NH— | FAB-MS(Pos); 415(M$^+$ + 1), Sal: HCl |
| 470 | 16 | 3-MeO$_2$C-4-mor | FAB-MS(Pos); 500(M$^+$ + 1) |
| 471 | 16 | 3-(HO—CH$_2$)-2-thiq | FAB-MS(Pos); 518(M$^+$ + 1) |
| 472 | 16 | (S)-2-EtO$_2$C-1-pipe | FAB-MS(Pos); 512(M$^+$ + 1) |
| 473 | 6 | 3-HO$_2$C-4-mor | FAB-MS(Pos); 486(M$^+$ + 1) |
| 474 | 6 | (S)-2-HO$_2$C-1-pipe | FAB-MS(Pos); 484(M$^+$ + 1) |
| 475 | 16 | (R)-2-EtO$_2$C-1-pipe | FAB-MS(Pos); 512(M$^+$ + 1) |
| 476 | 6 | (R)-2-HO$_2$C-1-pipe | FAB-MS(Pos); 484(M$^+$ + 1) |
| 477 | 1 | 2-((EtO)$_2$(O)P—CH$_2$)-1-pipe | FAB-MS(Pos); 590(M$^+$ + 1) |
| 478 | 7 | 2-((HO)$_2$(O)P—CH$_2$)-1-pipe | FAB-MS(Pos.); 534(M$^+$ + 1) |

TABLE 34

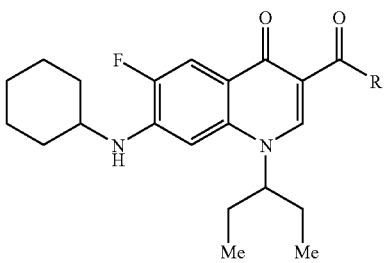

| Ex | Syn | R | Data |
|---|---|---|---|
| 23 | 16, 23 | (R)-MeO$_2$C—CH(CH$_2$-(3-Py))-NH— | FAB-MS(Pos); 537(M$^+$ + 1), Sal: HCl |
| 28 | 28 | HO$_2$C—C(Me)$_2$-NH— | FAB-MS(Pos); 460(M$^+$ + 1) |
| 479 | 16 | 3-EtO$_2$C-2-thiq | FAB-MS(Pos); 562(M$^+$ + 1) |
| 480 | 6 | 3-HO$_2$C-2-thiq | FAB-MS(Pos); 534(M$^+$ + 1) |
| 481 | 16 | (EtO)$_2$(O)P—(CH$_2$)$_2$—NH— | FAB-MS(Pos); 538(M$^+$ + 1) |
| 482 | 7 | (HO)$_2$(O)P—(CH$_2$)$_2$—NH— | FAB-MS(Pos); 482(M$^+$ + 1) |
| 483 | 16 | (S)-EtO$_2$C—(CH$_2$)$_2$CH(CO$_2$Et)-NH— | FAB-MS(Pos); 560(M$^+$ + 1) |
| 484 | 16 | EtO$_2$C—CH(CH$_2$OH)—NH— | FAB-MS(Pos); 490(M$^+$ + 1) |
| 485 | 6 | (S)-HO$_2$C—(CH$_2$)$_2$CH(CO$_2$H)-NH— | FAB-MS(Pos); 504(M$^+$ + 1) |
| 486 | 6 | (R)-HO$_2$C—CH(CH$_2$-(3-Py))-NH— | FAB-MS(Pos); 523(M$^+$ + 1) |
| 487 | 16 | (S)-MeO$_2$C—CH$_2$CH(CO$_2$Me)-NH— | FAB-MS(Pos); 518(M$^+$ + 1) |
| 488 | 16 | (R)-MeO$_2$C—CH(Bn)-NH— | FAB-MS(Pos); 484(M$^+$ + 1) |
| 489 | 16 | (R)-MeO$_2$C—CH(iBu)-NH— | FAB-MS(Pos); 502(M$^+$ + 1) |
| 490 | 16 | (R)-MeO$_2$C—CH(Me)-NH— | FAB-MS(Pos); 460(M$^+$ + 1) |
| 491 | 6 | HO$_2$C—CH(CH$_2$OH)—NH— | FAB-MS(Pos); 462(M$^+$ + 1) |

TABLE 34-continued

[Structure: 7-(cyclohexylamino)-6-fluoro-1-(pentan-3-yl)-4-oxo-1,4-dihydroquinoline-3-carbonyl-R]

| Ex | Syn | R | Data |
| --- | --- | --- | --- |
| 492 | 6 | (S)-HO$_2$C—CH$_2$CH(CO$_2$H)—NH— | FAB-MS(Pos); 490(M$^+$ + 1) |
| 493 | 6 | (R)-HO$_2$C—CH(Bn)-NH— | FAB-MS(Pos); 522(M$^+$ + 1) |
| 494 | 6 | (R)-HO$_2$C—CH$_2$CH(CO$_2$H)—NH— | FAB-MS(Pos); 490(M$^+$ + 1) |
| 495 | 6 | (S)-HO$_2$C—CH(iBu)-NH— | FAB-MS(Pos); 488(M$^+$ + 1) |
| 496 | 16 | (R)-HO$_2$C—CH(iPr)-NH— | FAB-MS(Pos); 488(M$^+$ + 1) |
| 497 | 16 | (S)-MeO$_2$C—CH$_2$CH(CO$_2$tBu)-NH— | FAB-MS(Pos); 560(M$^+$ + 1) |
| 498 | 16 | (R)-MeO$_2$C—(CH$_2$)$_2$CH(CO$_2$Me)-NH— | FAB-MS(Pos); 532(M$^+$ + 1) |
| 499 | 16 | (S)-MeO$_2$C—(CH$_2$)$_2$CH(CO$_2$tBu)-NH— | FAB-MS(Pos); 574(M$^+$ + 1) |
| 500 | 16 | (R)-EtO$_2$C—CH(tBu)-NH— | FAB-MS(Pos); 516(M$^+$ + 1) |
| 501 | 15 | (HO)$_2$(O)P—CF$_2$—CH$_2$NH— | ESI-MS(Pos); 518(M$^+$ + 1) Sal: HBr |
| 502 | 16 | (R)-MeO$_2$C—CH$_2$CH(CO$_2$Me)-NH— | FAB-MS(Pos); 518(M$^+$ + 1) |
| 503 | 5 | (S)-MeO$_2$C—CH$_2$CH(CO$_2$H)—NH— | FAB-MS(Pos); 504(M$^+$ + 1) |
| 504 | 5 | (S)-MeO$_2$C—(CH$_2$)$_2$CH(CO$_2$H)—NH— | FAB-MS(Pos); 518(M$^+$ + 1) |
| 505 | 16 | (S)-MeO$_2$C—CH(iBu)-NH— | FAB-MS(Pos); 502(M$^+$ + 1) |
| 506 | 28 | (R)-HO$_2$C—CH(tBu)-NH— | FAB-MS(Pos); 488(M$^+$ + 1) |
| 507 | 6 | (R)-HO$_2$C—CH(iBu)-NH— | FAB-MS(Pos); 488(M$^+$ + 1) |
| 508 | 16 | (1-MeO$_2$C-cPen)-NH— | FAB-MS(Pos); 500(M$^+$ + 1) |
| 509 | 28 | (1-HO$_2$C-cPen)-NH— | FAB-MS(Pos); 486(M$^+$ + 1) |
| 510 | 6 | (R)-HO$_2$C—CH(Me)-NH— | FAB-MS(Pos); 446(M$^+$ + 1) |
| 511 | 6 | (R)-HO$_2$C-CH(iPr)-NH— | FAB-MS(Pos); 474(M$^+$ + 1) |
| 512 | 16 | (S)-tBuO$_2$C—(CH$_2$)$_2$CH(CO$_2$Me)-NH— | FAB-MS(Pos); 574(M$^+$ + 1) |
| 513 | 5 | (S)-HO$_2$C—(CH$_2$)$_2$CH(CO$_2$Me)-NH— | FAB-MS(Pos); 518(M$^+$ + 1) |
| 514 | 16 | (S)-tBuO$_2$C—CH$_2$CH(CO$_2$Me)-NH— | FAB-MS(Pos); 560(M$^+$ + 1) |

TABLE 35

[Structure: 7-(cyclohexylamino)-6-fluoro-1-(pentan-3-yl)-4-oxo-1,4-dihydroquinoline-3-carbonyl-R]

| Ex | Syn | R | Data |
| --- | --- | --- | --- |
| 515 | 5 | (S)-HO$_2$C—CH$_2$CH(CO$_2$Me)-NH— | FAB-MS(Pos); 504(M$^+$ + 1) |
| 516 | 6 | (R)-HO$_2$C—(CH$_2$)$_2$CH(CO$_2$H)—NH— | FAB-MS(Pos); 504(M$^+$ + 1) |
| 517 | 1 | 2-((EtO)$_2$(O)P—CH$_2$)-1-pipe | FAB-MS(Pos); 592(M$^+$ + 1) |
| 518 | 7 | 2-((HO)$_2$(O)P—CH$_2$)-1-pipe | FAB-MS(Pos.); 536(M$^+$ + 1) |
| 519 | 1 | (EtO)$_2$(O)P—CH$_2$NH— | FAB-MS(Pos.); 524(M$^+$ + 1) |
| 520 | 1 | (EtO)$_2$(O)P—(CH$_2$)$_3$NH— | FAB-MS(Pos); 552(M$^+$ + 1) |
| 521 | 15 | (HO)$_2$(O)P—CH$_2$NH— | ESI-MS(Pos.); 468(M$^+$ + 1) Sal: HBr |
| 522 | 15 | (HO)$_2$(O)P—(CH$_2$)$_3$NH— | ESI-MS(Pos.); 496(M$^+$ + 1) Sal: HBr |
| 523 | 16 | (EtO)$_2$(O)P—CF$_2$—CH$_2$NH— | FAB-MS(Pos); 574(M$^+$ + 1) |
| 524 | 16 | EtO$_2$C—(CH$_2$)$_2$NH— | FAB-MS(Pos); 474(M$^+$ + 1) |
| 525 | 6 | HO$_2$C—(CH$_2$)$_2$NH— | FAB-MS(Pos); 446(M$^+$ + 1) |
| 526 | 6 | HO$_2$C—(CH$_2$)$_3$NH— | FAB-MS(Pos); 460(M$^+$ + 1) |
| 527 | 7 | (HO)$_2$(O)P—C(Me)$_2$-CH$_2$NH— | FAB-MS(Pos); 510(M$^+$ + 1) |
| 528 | 16 | (EtO)$_2$(O)P—C(Me)$_2$—CH$_2$NH— | FAB-MS(Pos); 566(M$^+$ + 1) |
| 529 | 16 | (S)-EtO$_2$C—(CH$_2$)$_3$CH(CO$_2$Et)-NH— | FAB-MS(Pos); 574(M$^+$ + 1) |
| 530 | 6 | (S)-HO$_2$C—(CH$_2$)$_3$CH(CO$_2$H)—NH— | FAB-MS(Pos); 518(M$^+$ + 1) |
| 531 | 16 | (EtO$_2$C—CH$_2$)$_2$N— | FAB-MS(Pos); 546(M$^+$ + 1) |

TABLE 35-continued

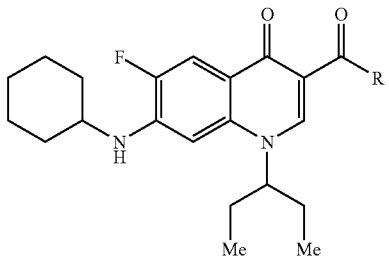

| Ex | Syn | R | Data |
|---|---|---|---|
| 532 | 6 | (HO₂C—CH₂)₂N— | FAB-MS(Pos); 476(M⁺ + 1) |
| 533 | 16 | (2-oxo-3-THF)—NH— | FAB-MS(Pos); 458(M⁺ + 1) |
| 534 | 6 | HO—(CH₂)₂CH(CO₂H)—NH— | FAB-MS(Pos); 476(M⁺ + 1) |
| 535 | 16 | (2,2-diMe-1,3-dioxolan-4-yl)—CH₂NH— | FAB-MS(Pos); 488(M⁺ + 1) |
| 536 | 4 | HO—CH₂CH(OH)CH₂—NH— | FAB-MS(Pos); 448(M⁺ + 1) |
| 537 | 16 | 3-EtO₂C-cHex-NH— | FAB-MS(Pos); 528(M⁺ + 1) |
| 538 | 6 | 3-HO₂C-cHex-NH— | FAB-MS(Pos); 500(M⁺ + 1) |
| 539 | 16 | (EtO₂CCH₂)₂CHNH— | FAB-MS(Pos); 560(M⁺ + 1) |
| 540 | 6 | (HO₂CCH₂)₂CHNH— | FAB-MS(Pos); 504(M⁺ + 1) |
| 541 | 16 | HO₂C—(CH₂)₄—NH— | FAB-MS(Pos); 474(M⁺ + 1) |
| 542 | 16 | (S)—HO₂CCHOH(CH₂)₂NH— | FAB-MS(Pos); 476(M⁺ + 1) |
| 543 | 16 | EtO₂C—(CH₂)₃NH— | FAB-MS(Pos); 488(M⁺ + 1) |
| 544 | 16 | MeO₂C—C(Me)₂—NH— | FAB-MS(Pos); 474(M⁺ + 1) |
| 545 | 16 | (EtO)₂(O)P-3-pipe- | FAB-MS(Pos); 578(M⁺ + 1) |
| 546 | 7 | (HO)₂(O)P-3-pipe- | FAB-MS(Pos); 522(M⁺ + 1) |

TABLE 36

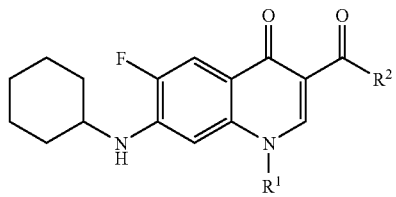

| Ex | Syn | R¹ | R² | Data |
|---|---|---|---|---|
| 18 | 18 | 2,2-diMe-1,3-dioxan-5-yl | (HO)₂(O)P—(CH₂)₂NH— | FAB-MS(Pos.); 526(M⁺ + 1) |
| 22 | 22 | (HO—CH₂)₂CH— | (HO)₂(O)P—(CH₂)₂NH— | FAB-MS(Pos.); 486(M⁺ + 1) |
| 547 | 16 | (S)-3-THF | HO—(CH₂)₃NH— | FAB-MS(Pos); 432(M⁺ + 1) |
| 548 | 16 | (R)-3-THF | HO—(CH₂)₃NH— | FAB-MS(Pos); 432(M⁺ + 1) |
| 549 | 16 | 1-Me-4-pipe | HO—(CH₂)₃NH— | FAB-MS(Pos); 459(M⁺ + 1) Sal: HCl |
| 550 | 1 | 1-Me-3-pyrr | HO—(CH₂)₃NH— | FAB-MS(Pos); 445(M⁺ + 1), Sal: HCl |
| 551 | 1 | iPr | (EtO)₂(O)P—(CH₂)₂NH— | FAB-MS(Pos); 510(M⁺ + 1) |
| 552 | 1 | (S)-3-THF | Me₂N— | FAB-MS(Pos); 402(M⁺ + 1) |
| 553 | 15 | iPr | (HO)₂(O)P—(CH₂)₂NH— | FAB-MS(Pos); 454(M⁺ + 1), Sal: HBr |
| 554 | 1 | 1-Me-3-pyrr | (EtO)₂(O)P—(CH₂)₂NH— | FAB-MS(Pos); 511(M⁺ + 1) |
| 555 | 1 | (S)-3-THF | (BnO)₂(O)P—(CH₂)₂NH— | ESI-MS(Pos); 662(M⁺ + 1) |
| 556 | 18 | (S)-3-THF | (HO)₂(O)P—(CH₂)₂NH— | FAB-MS(Pos); 482(M⁺ + 1) |
| 557 | 15 | 1-Me-3-pyrr | (HO)₂(O)P—(CH₂)₂NH— | FAB-MS(Pos); 495(M⁺ + 1), Sal: HBr |
| 558 | 1 | (R)-3-THF | (BnO)₂(O)P—(CH₂)₂NH— | FAB-MS(Pos); 662(M⁺ + 1) |
| 559 | 18 | (R)-3-THF | (HO)₂(O)P—(CH₂)₂NH— | FAB-MS(Pos); 482(M⁺ + 1) |
| 560 | 1, 23 | 1-Me-4-pipe | 3-EtO₂C-2-thiq | FAB-MS(Pos); 589(M⁺ + 1), Sal: HCl |
| 561 | 1, 23 | 1-Me-4-pipe | 2-EtO₂C-1-pipe | FAB-MS(Pos); 541(M⁺ + 1), Sal: HCl |
| 562 | 6 | 1-Me-4-pipe | 3-HO₂C-2-thiq | FAB-MS(Pos); 561(M⁺ + 1), Sal: HCl |
| 563 | 6 | 1-Me-4-pipe | 2-HO₂C-1-pipe | FAB-MS(Pos); 513(M⁺ + 1), Sal: HCl |
| 564 | 1.23 | (S)-1-Me-3-pyrr | (S)-3-EtO₂C-2-thiq | FAB-MS(Pos); 575(M⁺ + 1), Sal: HCl |

TABLE 36-continued

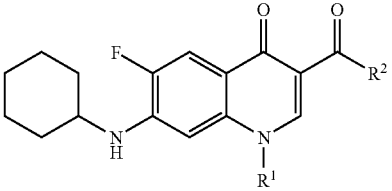

| Ex | Syn | R¹ | R² | Data |
|---|---|---|---|---|
| 565 | 1, 23 | (S)-1-Me-3-pyrr | (R)-3-EtO$_2$C-2-thiq | FAB-MS(Pos); 575(M$^+$ + 1), Sal: HCl |
| 566 | 6 | (S)-1-Me-3-pyrr | (S)-3-HO$_2$C-2-thiq | FAB-MS(Pos); 547(M$^+$ + 1), Sal: HCl |
| 567 | 1, 23 | (R)-1-Me-3-pyrr | (S)-3-EtO$_2$C-2-thiq | FAB-MS(Pos); 575(M$^+$ + 1), Sal: HCl |

TABLE 37

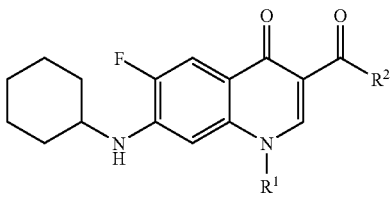

| Ex | Syn | R¹ | R² | Data |
|---|---|---|---|---|
| 568 | 1, 23 | (R)-1-Me-3-pyrr | (R)-3-EtO$_2$C-2-thiq | FAB-MS(Pos); 575(M$^+$ + 1), Sal: HCl |
| 569 | 6 | (S)-1-Me-3-pyrr | (R)-3-HO$_2$C-2-thiq | FAB-MS(Pos); 547(M$^+$ + 1), Sal: HCl |
| 570 | 6 | (R)-1-Me-3-pyrr | (S)-3-HO$_2$C-2-thiq | FAB-MS(Pos); 547(M$^+$ + 1), Sal: HCl |
| 571 | 6 | (R)-1-Me-3-pyrr | (R)-3-HO$_2$C-2-thiq | FAB-MS(Pos); 547(M$^+$ + 1), Sal: HCl |
| 572 | 1 | (S)-3-THF | (S)-3-EtO$_2$C-2-thiq | FAB-MS(Pos); 562(M$^+$ + 1) |
| 573 | 1 | (S)-3-THF | (R)-3-EtO$_2$C-2-thiq | FAB-MS(Pos); 562(M$^+$ + 1) |
| 574 | 1 | (R)-3-THF | (S)-3-EtO$_2$C-2-thiq | FAB-MS(Pos); 562(M$^+$ + 1) |
| 575 | 1 | (R)-3-THF | (R)-3-EtO$_2$C-2-thiq | FAB-MS(Pos); 562(M$^+$ + 1) |
| 576 | 6 | (R)-3-THF | (S)-3-HO$_2$C-2-thiq | FAB-MS(Pos); 534(M$^+$ + 1) |
| 577 | 6 | (S)-3-THF | (S)-3-HO$_2$C-2-thiq | FAB-MS(Pos); 534(M$^+$ + 1) |
| 578 | 6 | (R)-3-THF | (R)-3-HO$_2$C-2-thiq | FAB-MS(Pos); 534(M$^+$ + 1) |
| 579 | 1 | 3-THF | H$_2$N— | FAB-MS(Pos); 374(M$^+$ + 1) |
| 580 | 6 | (S)-3-THF | (R)-3-HO$_2$C-2-thiq | FAB-MS(Pos); 534(M$^+$ + 1) |
| 581 | 1 | sBu | 3-EtO$_2$C-2-thiq | FAB-MS(Pos); 548(M$^+$ + 1) |
| 582 | 1 | sBu | (EtO)$_2$(O)P—(CH$_2$)$_2$NH— | FAB-MS(Pos); 524(M$^+$ + 1) |
| 583 | 7 | sBu | (HO)$_2$(O)P—(CH$_2$)$_2$NH— | FAB-MS(Pos); 468(M$^+$ + 1) |
| 584 | 4 | sBu | (1RS,2SR,3SR,4SR)-2,3-diHO-4-HO(CH$_2$)$_2$O-cPen | FAB-MS(Pos); 520(M$^+$ + 1) |
| 585 | 6 | sBu | 3-HO$_2$C-2-thiq | FAB-MS(Pos); 520(M$^+$ + 1) |
| 586 | 16 | iPr | 3-EtO$_2$C-2-thiq | FAB-MS(Pos); 534(M$^+$ + 1) |
| 587 | 6 | iPr | 3-HO$_2$C-2-thiq | FAB-MS(Pos); 506(M$^+$ + 1) |
| 588 | 1 | sBu | 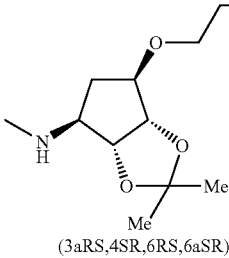 (3aRS,4SR,6RS,6aSR) | FAB-MS(Pos); 560(M$^+$ + 1) |
| 589 | 1 | 2,2-diMe-1,3-dioxan-5-yl | (BnO)$_2$(O)P—(CH$_2$)$_2$NH— | FAB-MS(Pos); 706(M$^+$ + 1) |
| 590 | 1 | 2,2-diMe-1,3-dioxan-5-yl | HO—(CH$_2$)$_3$NH— | FAB-MS(Pos.); 476(M$^+$ + 1) |

TABLE 37-continued
| Ex | Syn | R¹ | R² | Data |
|---|---|---|---|---|
| 591 | 22 | (HO—CH₂)₂CH— | HO—(CH₂)₃NH— | FAB-MS(Pos.); 436(M⁺ + 1) |
| 592 | 1 | 1-Me-4-pipe | (2-HO-Ph)-NH— | FAB-MS(Pos); 493(M⁺ + 1) |
TABLE 38
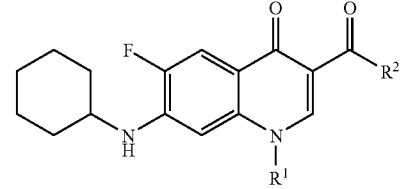
| Ex | Syn | R¹ | R² | Data |
|---|---|---|---|---|
| 593 | 16 | AcNH(CH₂)₂— | 3-EtO₂C-2-thiq | FAB-MS(Pos); 577(M⁺ + 1) |
| 594 | 6 | AcNH(CH₂)₂— | 3-HO₂C-2-thiq | FAB-MS(Pos); 549(M⁺ + 1) |
| 595 | 11 | 1-Me-3-pyrr | (2-HO-Ph)-N— | FAB-MS(Pos); 479(M⁺ + 1), Sal: HCl |
| 596 | 16 |  (1RS,2RS,4SR) | (S)-EtO₂C-(CH₂)₂—CH(CO₂Et)-NH— | FAB-MS(Pos); 584(M⁺ + 1) |
| 597 | 6 |  (1RS,2RS,4SR) | (S)-HO₂C-(CH₂)₂—CH(CO₂H)—NH— | FAB-MS(Pos); 528(M⁺ + 1) |
TABLE 39
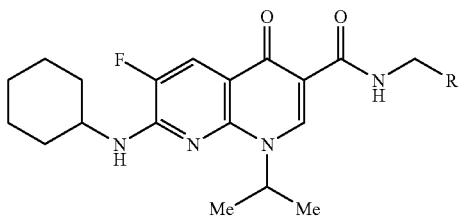
| EX | Syn | R | Data |
|---|---|---|---|
| 598 | 1 | CO₂Et | ESI-MS(Neg); 431(M⁺ − 1) |
| 599 | 6 | CO₂H | FAB-MS(Pos); 405(M⁺ + 1) |

TABLE 40

| Ex | Syn | —R¹—R²— | R³ | Data |
|---|---|---|---|---|
| 600 | 16 | —CH=CH—CH=CH— | $CO_2Et$ | FAB-MS(Pos); 440($M^+$ + 1) |
| 601 | 6 | —CH=CH—CH=CH— | $CO_2H$ | FAB-MS(Pos); 412($M^+$ + 1) |
| 602 | 16 | —(CH$_2$)$_4$— | $CO_2Et$ | FAB-MS(Pos); 444($M^+$ + 1) |
| 603 | 6 | —(CH$_2$)$_4$— | $CO_2H$ | FAB-MS(Pos); 416($M^+$ + 1) |
| 604 | 16 | —C(=CH$_2$)—(CH$_2$)$_2$— | $CO_2Et$ | FAB-MS(Pos); 442($M^+$ + 1) |
| 605 | 6 | —C(=CH$_2$)—(CH$_2$)$_2$— | $CO_2H$ | FAB-MS(Pos); 414($M^+$ + 1) |
| 606 | 16 | —CH(Me)-(CH$_2$)$_2$— | $CO_2Et$ | FAB-MS(Pos); 444($M^+$ + 1) |
| 607 | 6 | —CH(Me)-(CH$_2$)$_2$— | $CO_2H$ | FAB-MS(Pos); 416($M^+$ + 1) |
| 608 | 16 | —(CH$_2$)$_3$— | $CO_2Et$ | FAB-MS(Pos); 430($M^+$ + 1) |
| 609 | 6 | —(CH$_2$)$_3$— | $CO_2H$ | FAB-MS(Pos); 402($M^+$ + 1) |
| 610 | 16 | —CH$_2$—C(=CH$_2$)—(CH$_2$)$_2$— | $CO_2Et$ | FAB-MS(Pos); 456($M^+$ + 1) |
| 611 | 6 | —CH$_2$—C(=CH$_2$)—(CH$_2$)$_2$— | $CO_2H$ | FAB-MS(Pos); 428($M^+$ + 1) |
| 612 | 16 | —CH$_2$—CH(Me)-(CH$_2$)$_2$— | $CO_2Et$ | FAB-MS(Pos); 458($M^+$ + 1) |
| 613 | 6 | —CH$_2$—CH(Me)-(CH$_2$)$_2$— | $CO_2H$ | FAB-MS(Pos); 430($M^+$ + 1) |

TABLE 41

| Ex | Syn | R¹ | R² | A | R³ | Data |
|---|---|---|---|---|---|---|
| 614 | 16 | F | cPen | CMe | $EtO_2C$—$CH_2$— | FAB-MS(Pos); 472($M^+$ + 1) |
| 615 | 6 | F | cPen | CMe | $HO_2C$—$CH_2$— | FAB-MS(Pos); 444($M^+$ + 1) |
| 616 | 1 | F | Et | N | $EtO_2C$—$CH_2$— | FAB-MS(Pos.); 419($M^+$ + 1) |
| 617 | 6 | F | Et | N | $HO_2C$—$CH_2$— | FAB-MS(Pos.); 391($M^+$ + 1) |
| 618 | 1 | F | Et | N | $(EtO)_2(O)P$—$(CH_2)_2$— | FAB-MS(Pos); 497($M^+$ + 1) |
| 619 | 15 | F | Et | N | $(HO)_2(O)P$—$(CH_2)_2$— | ESI-MS(Pos.); 441($M^+$ + 1), Sal: HBr |
| 620 | 16 | OEt | Et | N | $EtO_2C$—$CH_2$— | FAB-MS(Pos); 445($M^+$ + 1) |
| 621 | 6 | OEt | Et | N | $HO_2C$—$CH_2$— | FAB-MS(Pos.); 417($M^+$ + 1) |
| 622 | 16 | F | cPen | N | $EtO_2C$—$CH_2$— | FAB-MS(Pos); 459($M^+$ + 1) |
| 623 | 6 | F | cPen | N | $HO_2C$—$CH_2$— | FAB-MS(Pos); 431($M^+$ + 1) |
| 624 | 16 | F | (Et)$_2$CH— | N | $EtO_2C$—$CH_2$— | FAB-MS(Pos); 461($M^+$ + 1) |
| 625 | 6 | F | (Et)$_2$CH— | N | $HO_2C$—$CH_2$— | FAB-MS(Pos); 433($M^+$ + 1) |
| 626 | 16 | F | (Et)$_2$CH— | N | $(EtO)_2(O)P$—$(CH_2)_2$— | FAB-MS(Pos); 539($M^+$ + 1) |
| 627 | 7 | F | (Et)$_2$CH— | N | $(HO)_2(O)P$—$(CH_2)_2$— | FAB-MS(Pos); 483($M^+$ + 1) |
| 628 | 16 | F | (Et)$_2$CH— | N | (S)-$EtO_2C$—$(CH_2)_2CH(CO_2Et)$- | FAB-MS(Pos); 561($M^+$ + 1) |
| 629 | 6 | F | (Et)$_2$CH— | N | (S)—$HO_2C$—$(CH_2)_2CH(CO_2H)$— | FAB-MS(Pos); 505($M^+$ + 1) |

NMR data of some compounds in the Examples are shown below in Tables 42 to 44.

TABLE 42

| Ex | Data |
|---|---|
| 6 | NMR(DMSO-$d_6$) δ; 1.10-1.25(m, 1H), 1.27-1.50(m, 4H), 1.61-1.70(m, 1H), 1.72-1.85(m, 6H), 1.85-2.01(m, 4H), 2.19-2.32(m, 2H), 3.50-3.63(m, 1H), 4.05(d, J=5.4Hz, 2H), 5.12-5.22(m, 1H), 6.33(dd, J=2.0, 8.3Hz, 1H), 6.85(d, J=7.3Hz, 1H), 7.79(d, J=12.2Hz, 1H), 8.60(s, 1H), 10.32(t, J=5.4Hz, 1H), 12.64(brs, 1H) |

TABLE 42-continued

| Ex | Data |
|---|---|
| 7 | NMR(DMSO-d$_6$) δ; 1.11-1.24(m, 1H), 1.27-1.48(m, 7H), 1.60-1.69(m, 1H), 1.71-1.89(m, 4H), 1.92-2.00(m, 2H), 3.44-3.62(m, 3H), 4.43(q, J=7.0Hz, 2H), 6.29(d, J=6.4Hz, 1H), 6.70(d, J=7.4Hz, 1H), 7.75(d, J=12.2Hz, 1H), 8.65(s, 1H), 10.16(t, J=5.9Hz, 1H) |
| 15 | NMR(DMSO-d$_6$) δ; 1.10-1.24(m, 1H), 1.27-1.50(m, 4H), 1.60-1.70(m, 1H), 1.71-2.00(m, 12H), 2.18-2.32(m, 2H), 3.44-3.64(m, 3H), 5.10-5.25(m, 1H), 6.86(d, J=7.3Hz, 1H), 7.76(d, J=12.2Hz, 1H), 8.62(s, 1H), 10.14(brs, 1H) |
| 18 | NMR(DMSO-d$_6$) δ; 1.10-1.24(m, 1H), 1.25-1.50(m, 7H), 1.51-1.56(s, 3H), 1.60-1.69(m, 1H), 1.71-2.02(m, 6H), 3.40-3.57(m, 3H), 4.02(d, J=13.2Hz, 2H), 4.50(d, J=13.2Hz, 2H), 4.72-4.78(m, 1H), 6.29(d, J=8.3Hz, 1H), 6.58(d, J=6.8Hz, 1H), 7.79(d, J=12.2Hz, 1H), 9.54(s, 1H), 10.14(t, J=5.8Hz, 1H) |
| 22 | NMR(DMSO-d$_6$) δ; 1.09-1.23(m, 1H), 1.24-1.48(m, 4H), 1.59-1.68(m, 1H), 1.70-1.98(m, 6H), 3.38-3.61(m, 3H), 3.75-3.92(m, 4H), 4.80-4.93(m, 1H), 5.13(brs, 2H), 6.21(d, J=7.8Hz, 1H), 6.85(d, J=7.3Hz, 1H), 7.77(d, J=12.2Hz, 1H), 8.69(s, 1H), 10.19(t, J=5.8Hz, 1H) |
| 161 | NMR(DMSO-d$_6$) δ; 1.10-1.25(m, 1H), 1.27-1.49(m, 7H), 1.60-1.69(m, 1H), 1.72-1.80(m, 2H), 1.91-2.00(m, 2H), 3.51-3.62(m, 1H), 4.05(d, J=5.4Hz, 2H), 4.43(q, J=6.9Hz, 2H), 6.31(dd, J=2.4, 8.3Hz, 1H), 6.71(d, J=7.4Hz, 1H), 7.77(d, J=12.2Hz, 1H), 8.65(s, 1H), 10.35(t, J=5.4Hz, 1H), 12.63(brs, 1H) |
| 255 | NMR(DMSO-d$_6$) δ; 1.10-1.25(m, 1H), 1.27-1.49(m, 4H), 1.50(d, J=6.8Hz, 6H), 1.60-1.70(m, 1H), 1.71-1.80(m, 2H), 1.91-2.00(m, 2H), 3.53-3.65(m, 1H), 4.05(d, J=5.4Hz, 2H), 5.12(quintet, J=6.8Hz, 1H), 6.30(dd, J=2.5, 8.3Hz, 1H), 6.87(d, J=6.9Hz, 1H), 7.80(d, J=12.2Hz, 1H), 8.65(s, 1H), 10.34(t, J=5.4Hz, 1H), 12.62(brs, 1H) |
| 259 | NMR(DMSO-d$_6$) δ; 1.10-1.25(m, 1H), 1.23-1.48(m, 5H), 1.53-1.81(m, 8H), 1.85-1.94(m, 2H), 1.94-2.02(m, 2H), 2.04-2.13(m, 2H), 3.50-3.64(m, 1H), 4.05(d, J=5.4Hz, 2H), 4.56-4.67(m, 1H), 6.39(dd, J=2.0, 8.0Hz, 1H), 6.78(d, J=7.4Hz, 1H), 7.79(d, J=12.7Hz, 1H), 8.64(s, 1H), 10.33(t, J=5.4Hz, 1H), 12.63(brs, 1H) |
| 406 | NMR(DMSO-d$_6$) δ; 1.12-1.24(m, 1H), 1.26-1.49(m.4H), 1.59-2.00(m, 13H), 2.18-2.29(m, 2H), 3.36-3.48(m, 2H), 3.50-3.61(m, 1H), 3.94-4.06(m, 1H), 5.10-5.21(m, 1H), 5.33(brs, 1H), 6.31(d, 1H, J=6.9Hz), 6.84(d, J=6.9Hz, 1H), 7.77(d, J=12.2Hz, 1H), 8.62(s, 1H), 10.14(t, J=5.9Hz, 1H), 12.45(brs, 1H) |
| 416 | NMR(DMSO-d$_6$) δ; 1.10-1.24(m, 1H), 1.27-1.50(m, 4H), 1.60-1.70(m, 1H), 1.71-2.00(m, 10H), 2.19-2.31(m, 2H), 3.50-3.63(m, 3H), 3.87-3.96(m, 2H), 5.11-5.22(m, 1H), 6.32(d, J=6.8Hz, 1H), 6.85(d, J=7.3Hz, 1H), 7.78(d, J=12.2Hz, 1H), 8.62(s, 1H), 10.22(t, J=5.8Hz, 1H) |

TABLE 43

| Ex | Data |
|---|---|
| 417 | NMR(DMSO-d$_6$) δ; 1.10-1.24(m, 1H), 1.27-1.50(m, 4H), 1.60-1.70(m, 1H), 1.71-2.00(m, 10H), 2.18-2.33(m, 2H), 2.72-2.88(m, 2H), 3.50-3.66(m, 1H), 4.75-4.82(m, 1H), 5.11-5.21(m, 1H), 6.30(brs, 1H), 6.85(d, J=7.3Hz, 1H), 7.77(d, J=12.2Hz, 1H), 8.60(s, 1H), 10.59(d, J=7.8Hz, 1H) |
| 419 | NMR(DMSO-d$_6$, 80° C.) δ; 1.15-1.28(m, 1H), 1.30-1.50(m, 4H), 1.60-1.69(m, 1H), 1.70-2.02(m, 10H), 2.15-2.30(m, 2H), 2.95-3.30(m, 2H), 3.48-3.65(m, 1H), 4.05(brs, 1H), 4.49(brs, 1H), 4.60-5.10(m, 2H), 5.82(brd, J=6.4Hz, 1H), 6.82(d, J=6.8Hz, 1H), 7.16(brs, 4H), 7.74(d, J=12.7Hz, 1H), 7.89(s, 1H), 12.48(brs, 1H) |
| 425 | NMR(DMSO-d$_6$) δ; 1.10-1.25(m, 1H), 1.27-1.50(m, 4H), 1.60-1.70(m, 1H), 1.71-2.00(m, 11H), 2.04-2.15(m, 1H), 2.20-2.33(m, 4H), 3.52-3.64(m, 1H), 4.48-4.56(m, 1H), 5.12-5.21(m, 1H), 6.34(brd, J=6.4Hz, 1H), 6.85(d, J=6.8Hz, 1H), 7.79(d, J=12.2Hz, 1H), 8.59(s, 1H), 10.48(d, J=7.8Hz, 1H)12.50(brs, 2H) |
| 429 | NMR(DMSO-d$_6$) δ; 1.12-1.24(m, 1H), 1.26-1.48(m, 4H), 1.60-1.68(m, 1H), 1.71-1.99(m, 12H), 2.18-2.30(m, 2H), 2.88(dd, J=7.4, 13.7Hz, 1H), 3.12(dd, J=5.4, 13.7Hz, 1H), 3.50-3.62(m, 1H), 4.38-4.51(m, 1H), 5.10-5.18(m, 1H), 6.30(d, J=6.3Hz, 1H), 6.83(d, J=7.3Hz, 1H), 7.14-7.30(m, 5H), 7.75(d, J=12.2Hz, 1H), 8.57(s, 1H), 10.18(d, J=7.8Hz, 1H) |
| 482 | NMR(DMSO-d$_6$) δ; 0.77(t, J=7.4Hz, 6H), 1.12-1.52(m, 5H), 1.61-2.00(m, 11H), 3.44-3.55(m, 2H), 3.58-3.70(m, 1H), 4.80-4.90(m, 1H), 6.26(d, J=6.8Hz, 1H), 6.93(d, J=6.8Hz, 1H), 7.77 d, J=12.2Hz, 1H), 8.51(s, 1H), 10.16(t, J=5.6Hz, 1H) |
| 485 | NMR(DMSO-d$_6$) δ; 0.74-0.82(m, 6H), 1.11-1.52(m, 5H), 1.60-1.98(m, 10H), 2.05-2.15(m, 1H), 2.23-2.37(m, 2H), 3.60-3.75(m, 1H), 4.48-4.56(m, 1H), 4.80-4.92(m, 1H), 6.30(d, J=6.8H, 1H), 6.94(d, J=6.9Hz, 1H), 7.80(d, J=12.2Hz, 1H), 8.50(s, 1H), 10.51(d, J=7.8Hz, 1H), 12.49(brs, 2H) |
| 492 | NMR(DMSO-d$_6$) δ; 0.78(t, J=7.3Hz, 6H), 1.11-1.51(m, 5H), 1.62-1.98(m, 9H), 2.75(dd, J=5.4, 16.6Hz, 1H), 2.84(dd, J=5.6, 16.6Hz, 1H), 3.60-3.75(m, 1H), 4.76-4.90(m, 2H), 6.28(d, J=6.8H, 1H), 6.93(d, J=6.8Hz, 1H), 7.78(d, J=12.2Hz, 1H), 8.51(s, 1H), 10.62(d, J=8.3Hz, 1H), 12.68(brs, 2H) |
| 501 | NMR(DMSO-d$_6$) δ; 0.78(t, J=7.3Hz, 6H), 1.10-1.50(m, 5H), 1.60-2.00(m, 9H), 3.60-3.70(m, 1H), 3.80-4.05(m, 2H), 4.80-4.93(m, 1H), 6.95(d, J=6.8Hz, 1H), 7.79(d, J=12.3Hz, 1H), 8.54(s, 1H), 10.48(t, J=5.8Hz, 1H) |
| 522 | NMR(DMSO-d$_6$) δ; 0.78(t, J=7.4Hz, 6H), 1.11-1.50(m, 5H), 1.51-2.00(m, 13H), 3.34-3.39(m, 2H), 3.60-3.70(m, 1H), 4.80-4.90(m, 1H), 6.94(d, J=6.9Hz, 1H), 7.79(d, J=12.2Hz, 1H), 8.53(s, 1H), 10.16(t, J=5.6Hz, 1H) |

TABLE 43-continued

| Ex | Data |
|---|---|
| 527 | NMR(DMSO-$d_6$, 80° C.) δ; 0.79(t, J=7.3Hz, 6H), 1.01(d, J=13.7Hz, 6H), 1.13-1.48(m, 5H), 1.58-1.97(m, 9H), 3.25-3.45(m, 2H), 3.54(brs, 1H), 4.65(brs, 1H), 5.70-5.84(m, 1H), 6.82(d, J=6.8Hz, 1H), 7.92(d, J=12.6Hz, 1H), 8.52(s, 1H), 10.05(brs, 1H) |
| 553 | NMR(DMSO-$d_6$) δ; 1.10-1.25(m, 1H), 1.27-1.50(m, 4H), 1.51(d, J=6.3Hz, 6H), 1.60-1.70(m, 1H), 1.71-1.80(m, 2H), 1.81-1.99(m, 4H), 3.45-3.56(m, 2H), 3.56-3.66(m, 1H), 5.07-5.20(m, 1H), 6.88(d, J=7.3Hz, 1H), 7.78(d, J=12.2Hz, 1H), 8.69(s, 1H), 10.15(brs, 1H) |
| 556 | NMR(DMSO-$d_6$) δ; 1.10-1.50(m, 5H), 1.60-1.70(m, 1H), 1.70-1.90(m, 4H), 1.90-2.02(m, 2H), 2.05-2.17(m, 1H), 2.55-2.67(m, 1H), 3.42-3.59(m, 3H), 3.76-3.84(m, 1H), 3.88-3.96(m, 1H), 4.02-4.11(m, 1H), 4.22-4.30(m, 1H), 5.45(brs, 1H), 6.34(brd, J=5.9Hz, 1H), 6.90(d, J=7.3Hz, 1H), 7.76(d, J=12.2Hz, 1H), 8.65(s, 1H), 10.13(t, J=5.8Hz, 1H) |

TABLE 44

| Ex | Data |
|---|---|
| 559 | NMR(DMSO-$d_6$) δ; 1.10-1.50(m, 5H), 1.60-1.70(m, 1H), 1.70-1.90(m, 4H), 1.90-2.02(m, 2H), 2.05-2.17(m, 1H), 2.55-2.67(m, 1H), 3.42-3.59(m, 3H), 3.76-3.84(m, 1H), 3.88-3.96(m, 1H), 4.02-4.11(m, 1H), 4.22-4.30(m, 1H), 5.45(brs, 1H), 6.34(brd, J=6.4Hz, 1H), 6.90(d, J=7.3Hz, 1H), 7.76(d, J=12.2Hz, 1H), 8.65(s, 1H), 10.13(t, J=5.8Hz, 1H) |
| 576 | NMR(DMSO-$d_6$, 80° C.) δ; 1.15-1.30(m, 1H), 1.30-1.50(m, 4H), 1.60-1.70(m, 1H), 1.70-1.82(m, 2H), 1.94-2.03(m, 2H), 2.08-2.22(m, 1H), 2.50-2.64(m, 1H), 2.90-3.35(m, 2H), 3.46-3.58(m, 1H), 3.74-3.86(m, 1H), 3.89-4.00(m, 1H), 4.00-4.25(m, 3H), 4.35-5.10(m, 2H), 5.35(brs, 1H), 5.86(brd, J=6.8Hz, 1H), 6.88(brd, J=6.4Hz, 1H), 7.16(brs, 4H), 7.73(d, J=12.2Hz, 1H), 7.92(s, 1H) |
| 578 | NMR(DMSO-$d_6$, 80° C.) δ; 1.15-1.30(m, 1H), 1.30-1.50(m, 4H), 1.60-1.70(m, 1H), 1.70-1.82(m, 2H), 1.94-2.03(m, 2H), 2.08-2.22(m, 1H), 2.50-2.64(m, 1H), 2.94-3.35(m, 2H), 3.46-3.58(m, 1H), 3.74-3.85(m, 1H), 3.90-4.00(m, 1H), 4.00-4.25(m, 3H), 4.35-5.15(m, 2H), 5.35(brs, 1H), 5.87(brd, J=6.3Hz, 1H), 6.88(brd, J=7.3Hz, 1H), 7.16(brs, 4H), 7.73(d, J=12.2Hz, 1H), 7.92(s, 1H), 12.46(brs, 1H) |
| 583 | NMR(DMSO-$d_6$) δ; 0.84(t, J=7.4Hz, 3H), 1.12-1.46(m, 5H), 1.49(d, J=6.3Hz, 3H), 1.61-1.69(m, 1H), 1.70-1.90(m, 6H), 1.91-2.00(m, 2H), 3.43-3.65(m, 3H), 4.93(q, J=6.5Hz, 1H), 6.29(d, J=6.4Hz, 1H), 6.86(d, J=7.3Hz, 1H), 7.70(d, J=12.2Hz, 1H), 8.58(s, 1H), 10.15(t, J=5.6Hz, 1H) |
| 619 | NMR(DMSO-$d_6$) δ; 1.10-1.23(m, 1H), 1.29-1.50(m, 7H), 1.62-1.69(m, 1H), 1.72-1.80(m, 2H), 1.80-1.90(m, 2H), 1.92-1.99(m, 2H), 3.45-3.56(m, 2H), 3.60-3.70(m, 1H), 4.58(q, J=7.3Hz, 2H), 6.73(d, J=7.3Hz, 1H), 7.70(d, J=11.7Hz, 1H), 10.00(t, J=5.4Hz, 1H) |
| 627 | NMR(DMSO-$d_6$) δ; 0.83(t, J=7.4Hz, 6H), 1.10-1.24(m, 4H), 1.26-1.52(m, 4H), 1.55-2.02(m, 11H), 3.44-3.55(m, 2H), 3.62-3.75(m, 1H), 4.94-5.04(m, 1H), 6.65(d, J=8.3Hz, 1H), 6.91(d, J=6.8Hz, 1H), 7.71(d, J=11.7Hz, 1H), 10.00(t, J=5.6Hz, 1H) |
| 629 | NMR(DMSO-$d_6$) δ; 0.70-0.77(m, 6H), 1.11-1.24(m, 6H), 1.28-1.52(m, 4H), 1.63-1.70(m, 1H), 1.72-1.86(m, 4H), 1.90-2.03(m, 5H), 2.05-2.17(m, 1H), 2.25-2.39(m, 2H), 3.65-3.76(m, 1H), 4.51-4.57(m, 1H), 4.98-5.07(m, 1H), 6.70(d, J=8.3Hz, 1H), 6.93(d, J=6.8Hz, 1H), 7.75(d, J=11.7Hz, 1H), 10.49(d, J=7.3Hz, 1H) |

The structures of alternative compounds of the invention are shown below in Tables 45 to 67. These can be produced readily by the production processes described above, the processes described in the Examples or processes obvious to persons skilled in the art or modified processes thereof.

TABLE 45

| Ex | R |
|---|---|
| A1 | (HO)$_2$(O)P—CF$_2$CH$_2$NH— |
| A2 | (S)-HO$_2$C—(CH$_2$)$_3$CH(CO$_2$H)NH— |

TABLE 45-continued

| Ex | R |
|---|---|
| A3 | (HO$_2$C—CH$_2$)$_2$CH—NH— |
| A4 | (HO$_2$C—(CH$_2$)$_2$)(HO$_2$C—CH$_2$)N— |
| A5 | (HO$_2$C—(CH$_2$)$_3$)(HO$_2$C—CH$_2$)N— |
| A6 | (HO$_2$C—(CH$_2$)$_3$)(HO$_2$C—(CH$_2$)$_2$)N— |
| A7 | (HO$_2$C)$_2$CHNH— |
| A8 | ((HO$_2$C—(CH$_2$)$_2$)$_2$N— |
| A9 | HO$_2$C—CH$_2$CH(CH$_2$OH)CH$_2$NH— |
| A10 | HO$_2$C—(CH$_2$)$_2$—CH(CH$_2$OH)NH— |

TABLE 45-continued

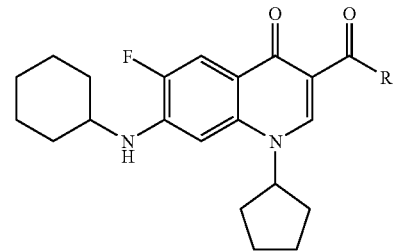

| Ex | R |
|---|---|
| A11 | (HO₂C—CH₂)₂CHCH₂NH— |
| A12 | HO₂C—CH(OH)CH₂NH— |
| A13 | HO₂C—CH₂CH(OH)CH₂NH— |
| A14 | HO—(CH₂)₃—CH(CO₂H)NH— |
| A15 | HO—CH₂CH(CO₂H)CH₂NH— |
| A16 | HO₂C—CF₂CH₂NH— |
| A17 | HO₂C—CH₂CF₂CH₂NH— |
| A18 | HO₂C—CF₂—(CH₂)₂—NH— |
| A19 | HO₂C—CF₂CH₂CH(CO₂H)NH— |
| A20 | HO₂C—CH₂CF₂CH(CO₂H)NH— |
| A21 | HO₂C—CF₂CH(CO₂H)NH— |
| A22 | 2-((HO)₂(O)P)-cHex-NH— |
| A23 | 3-((HO)₂(O)P)-cHex-NH— |
| A24 | 4-((HO)₂(O)P)-1-pipe |
| A25 | (HO)₂(O)P—CHF—CH₂NH— |
| A26 | HO₂C—CHF—CH₂NH— |
| A27 | HO₂C—CH₂—CHF—CH₂NH— |
| A28 | HO₂C—CHF—(CH₂)₂—NH— |
| A29 | HO₂C—CHF—CH₂CH(CO₂H)NH— |
| A30 | HO₂C—CH₂—CHF—CH(CO₂H)NH— |
| A31 | HO₂C—CHF—CH(CO₂H)NH— |

TABLE 46

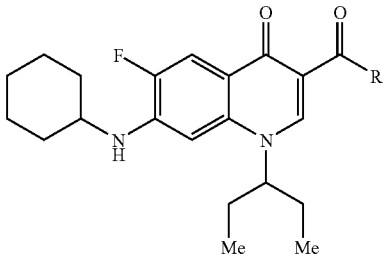

| Ex | R |
|---|---|
| B1 | (HO)₂(O)P—O—(CH₂)₂—NH— |
| B2 | (HO₂C—(CH₂)₂)HO₂C—CH₂)N— |
| B3 | (HO₂C—(CH₂)₃)(HO₂C—CH₂)N— |
| B4 | (HO₂C—(CH₂)₃)(HO₂C—(CH₂)₂)N— |
| B5 | (HO₂C)₂CHNH— |
| B6 | ((HO₂C—(CH₂)₂)₂N— |
| B7 | HO₂C—CH₂CH(CH₂OH)CH₂NH— |
| B8 | HO₂C—(CH₂)₂—CH(CH₂OH)NH— |
| B9 | (HO₂C—CH₂)₂CHCH₂NH— |
| B10 | HO₂C—CH(OH)CH₂NH— |
| B11 | HO₂C—CH₂CH(OH)CH₂NH— |
| B12 | HO—(CH₂)₃—CH(CO₂H)NH— |
| B13 | HO—CH₂CH(CO₂H)CH₂NH— |
| B14 | HO₂C—CF₂CH₂NH— |
| B15 | HO₂C—CH₂CF₂CH₂NH— |
| B16 | HO₂C—CF₂—(CH₂)₂—NH— |
| B17 | HO₂C—CF₂CH₂CH(CO₂H)NH— |
| B18 | HO₂C—CH₂CF₂CH(CO₂H)NH— |
| B19 | HO₂C—CF₂CH(CO₂H)NH— |
| B20 | 2-((HO)₂(O)P)-cHex-NH— |
| B21 | 3-((HO)₂(O)P)-cHex-NH— |
| B22 | 4-((HO)₂(O)P)-1-pipe |
| B23 | (HO)₂(O)P—CHF—CH₂NH— |

TABLE 46-continued

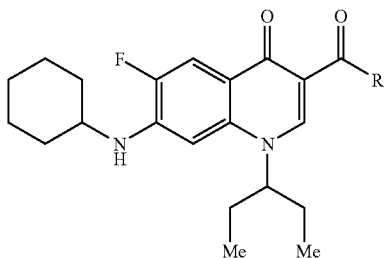

| Ex | R |
|---|---|
| B24 | HO₂C—CHF—CH₂NH— |
| B25 | HO₂C—CH₂—CHF—CH₂NH— |
| B26 | HO₂C—CHF—(CH₂)₂—NH— |
| B27 | HO₂C—CHF—CH₂CH(CO₂H)NH— |
| B28 | HO₂C—CH₂—CHF—CH(CO₂H)NH— |
| B29 | HO₂C—CHF—CH(CO₂H)NH— |

TABLE 47

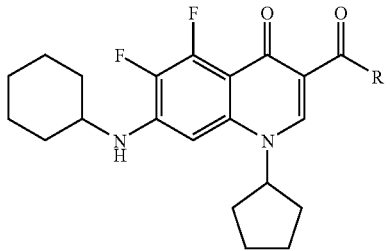

| Ex | R |
|---|---|
| C1 | HO₂C—CH₂NH— |
| C2 | (S)—HO₂C—(CH₂)₂CH(CO₂H)NH— |
| C3 | (HO)₂(O)P—(CH₂)₂NH— |
| C4 | (HO)₂(O)P—CF₂CH₂NH— |
| C5 | (S)—HO₂C—CH₂CH(CO₂H)NH— |
| C6 | (S)—HO₂C—(CH₂)₃CH(CO₂H)NH— |
| C7 | (HO₂C—CH₂)₂CH—NH— |
| C8 | (HO)₂(O)P—O—(CH₂)₂—NH— |
| C9 | (HO₂C—(CH₂)₂)(HO₂C—CH₂)N— |
| C10 | (HO₂C—(CH₂)₃)(HO₂C—CH₂)N— |
| C11 | (HO₂C—(CH₂)₃)(HO₂C(CH₂)₂)N— |
| C12 | (HO₂C)₂CHNH— |
| C13 | ((HO₂C—(CH₂)₂)₂N— |
| C14 | HO₂C—CH₂CH(CH₂OH)CH₂NH— |
| C15 | HO₂C—(CH₂)₂—CH(CH₂OH)NH— |
| C16 | (HO₂C—(CH₂)₂)₂CHCH₂NH— |
| C17 | HO₂C—CH(OH)CH₂NH— |
| C18 | HO₂C—CH₂CH(OH)CH₂NH— |
| C19 | HO—(CH₂)₃—CH(CO₂H)NH— |
| C20 | HO—CH₂CH(CO₂H)CH₂NH— |
| C21 | HO₂C—CF₂CH₂NH— |
| C22 | HO₂C—CH₂CF₂CH₂NH— |
| C23 | HO₂C—CF₂—(CH₂)₂—NH— |
| C24 | HO₂C—CF₂CH₂CH(CO₂H)NH— |
| C25 | HO₂C—CH₂CF₂CH(CO₂H)NH— |
| C26 | HO₂C—CF₂CH(CO₂H)NH— |
| C27 | 2-((HO)₂(O)P)-cHex-NH— |
| C28 | 3-((HO)₂(O)P)-cHex-NH— |
| C29 | 4-((HO)₂(O)P)-1-pipe |
| C30 | (HO)₂(O)P—CHF—CH₂NH— |
| C31 | HO₂C—CHF—CH₂NH— |
| C32 | HO₂C—CH₂—CHF—CH₂NH— |
| C33 | HO₂C—CHF—(CH₂)₂—NH— |
| C34 | HO₂C—CHF—CH₂CH(CO₂H)NH— |
| C35 | HO₂C—CH₂—CHF—CH(CO₂H)NH— |
| C36 | HO₂C—CHF—CH(CO₂H)NH— |

TABLE 48

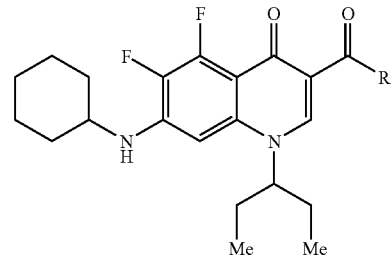

| Ex | R |
|---|---|
| D1 | (S)—HO$_2$C—(CH$_2$)$_2$CH(CO$_2$H)NH— |
| D2 | (HO)$_2$(O)P—(CH$_2$)$_2$NH— |
| D3 | (HO)$_2$(O)P—CF$_2$CH$_2$NH— |
| D4 | (S)-HO$_2$C—CH$_2$CH(CO$_2$H)NH— |
| D5 | (S)-HO$_2$C—(CH$_2$)$_3$CH(CO$_2$H)NH— |
| D6 | (HO$_2$C—CH$_2$)$_2$CH—NH— |
| D7 | (HO)$_2$(O)P—O—(CH$_2$)$_2$—NH— |
| D8 | (HO$_2$C—(CH$_2$)$_2$)(HO$_2$C—CH$_2$)N— |
| D9 | (HO$_2$C—(CH$_2$)$_3$)(HO$_2$C—CH$_2$)N— |
| D10 | (HO$_2$C—(CH$_2$)$_3$)(HO$_2$C—(CH$_2$)$_2$)N— |
| D11 | (HO$_2$C)$_2$CHNH— |
| D12 | ((HO$_2$C—(CH$_2$)$_2$)$_2$N— |
| D13 | HO$_2$C—CH$_2$CH(CH$_2$OH)CH$_2$NH— |
| D14 | HO$_2$C—(CH$_2$)$_2$—CH(CH$_2$OH)NH— |
| D15 | (HO$_2$C—CH$_2$)$_2$CHCH$_2$NH— |
| D16 | HO$_2$C—CH(OH)CH$_2$NH— |
| D17 | HO$_2$C—CH$_2$CH(OH)CH$_2$NH— |
| D18 | HO—(CH$_2$)$_3$—CH(CO$_2$H)NH— |
| D19 | HO—CH$_2$CH(CO$_2$H)CH$_2$NH— |
| D20 | HO$_2$C—CF$_2$CH$_2$NH— |
| D21 | HO$_2$C—CH$_2$CF$_2$CH$_2$NH— |
| D22 | HO$_2$C—CF$_2$—(CH$_2$)$_2$—NH— |
| D23 | HO$_2$C—CF$_2$CH$_2$CH(CO$_2$H)NH— |
| D24 | HO$_2$C—CH$_2$CF$_2$CH(CO$_2$H)NH— |
| D25 | HO$_2$C—CF$_2$CH(CO$_2$H)NH— |
| D26 | 2-((HO)$_2$(O)P)-cHex-NH— |
| D27 | 3-((HO)$_2$(O)P)-cHex-NH— |
| D28 | 4-((HO)$_2$(O)P)-1-pipe |
| D29 | (HO)$_2$(O)P—CHF—CH$_2$NH— |
| D30 | HO$_2$C—CHF—CH$_2$NH— |
| D31 | HO$_2$C—CH$_2$—CHF—CH$_2$NH— |
| D32 | HO$_2$C—CHF—(CH$_2$)$_2$—NH— |
| D33 | HO$_2$C—CHF—CH$_2$CH(CO$_2$H)NH— |
| D34 | HO$_2$C—CH$_2$—CHF—CH(CO$_2$H)NH— |
| D35 | HO$_2$C—CHF—CH(CO$_2$H)NH— |

TABLE 49

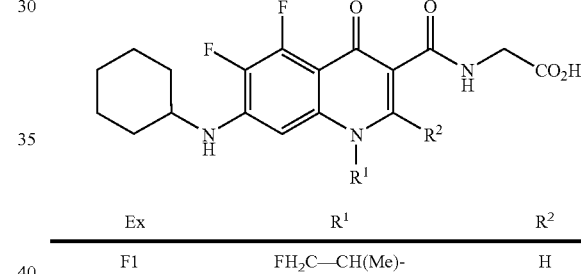

| Ex | R$^1$ | R$^1$ |
|---|---|---|
| E1 | 3,4-diMe-cPen | H |
| E2 | 3-Me-cPen | H |
| E3 | 3,4-diMe-cyclopent-3-en-1-yl | H |
| E4 | 3,3-diMe-cPen | H |
| E5 | 3,4-diF-cPen | H |
| E6 | 3-F-cPen | H |
| E7 | 3,3-diF-cPen | H |
| E8 | 3,4-diF-cyclopent-3-en-1-yl | H |
| E9 | 3-F-cyclopent-3-en-1-yl | H |
| E10 | 3-THP | H |
| E11 | 2-Py | H |

TABLE 49-continued

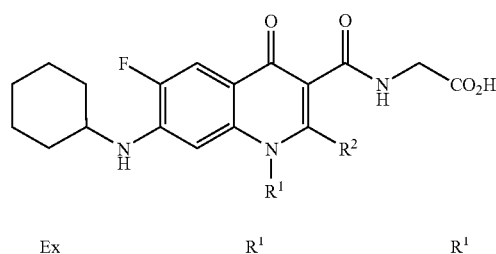

| Ex | R$^1$ | R$^1$ |
|---|---|---|
| E12 | 3-Py | H |
| E13 | 4-Py | H |
| E14 | —CH(Et)-(CH$_2$)$_3$— | |
| E15 | —CH(Et)-(CH$_2$)$_2$— | |
| E16 | —CH$_2$—C(Me)$_2$-(CH$_2$)$_2$— | |
| E17 | —CH$_2$—CHF—CH$_2$)$_2$— | |
| E18 | —CH$_2$—CF$_2$—CH$_2$)$_2$— | |
| E19 | (Et)$_2$CH— | Cl |
| E20 | cPen | Cl |
| E21 | (Et)$_2$CH— | CF$_3$ |
| E22 | cPen | CF$_3$ |

TABLE 50

| Ex | R$^1$ | R$^2$ |
|---|---|---|
| F1 | FH$_2$C—CH(Me)- | H |
| F2 | F$_2$HC—CH(Me)- | H |
| F3 | iPr | H |
| F4 | (HO—CH$_2$)$_2$CH— | H |
| F5 | 1-Me-3-pyrr | H |
| F6 | 3-THF | H |
| F7 | 2,2-diMe-1,3-dioxan-5-yl | H |
| F8 | 2,2-diEt-1,3-dioxan-5-yl | H |
| F9 | 3,4-diMe-cPen | H |
| F10 | 3-Me-cPen | H |
| E11 | 3,4-diMe-cyclopent-3-en-1-yl | H |
| F12 | 3-Me-cyclopent-3-en-1-yl | H |
| F13 | 3,3-diMe-cPen | H |
| F14 | 3,4-diF-cPen | H |
| F15 | 3-F-cPen | H |
| F16 | 3,3-diF-cPen | H |
| F17 | 3,4-diF-cyclopent-3-en-1-yl | H |
| F18 | 3-F-cyclopent-3-en-1-yl | H |
| F19 | 3-THP | H |
| F20 | 2-Py | H |
| F21 | 3-Py | H |
| F22 | 4-Py | H |
| F23 | —CH(Et)-(CH$_2$)$_3$— | |
| F24 | —CH(Et)-(CH$_2$)$_2$— | |
| F25 | —CH$_2$—C(=CH$_2$)—(CH$_2$)$_2$— | |
| F26 | —CH$_2$—CH(Me)-(CH$_2$)$_2$— | |
| F27 | —CH$_2$—C(Me)$_2$-(CH$_2$)$_2$— | |
| F28 | —CH$_2$—CHF—(CH$_2$)$_2$— | |
| F29 | —CH$_2$—CF$_2$—CH$_2$)$_2$— | |
| F30 | (Et)$_2$CH— | Cl |
| F31 | cPen | Cl |
| F32 | (Et)$_2$CH— | CF$_3$ |
| F33 | cPen | CF$_3$ |

TABLE 51

| Ex | R¹ | R² |
|---|---|---|
| G1 | FH₂C—CH(Me)- | H |
| G2 | F₂HC—CH(Me)- | H |
| G3 | iPr | H |
| G4 | Et | H |
| G5 | (HO—CH₂)₂CH— | H |
| G6 | 1-Me-3-pyrr | H |
| G7 | 3-THF | H |
| G8 | 2,2-diMe-1,3-dioxan-5-yl | H |
| G9 | 2,2-diEt-1,3-dioxan-5-yl | H |
| G10 | 3,4-diMe-cPen | H |
| G11 | 3-Me-cPen | H |
| G12 | 3,4-diMe-cyclopent-3-en-1-yl | H |
| G13 | 3-Me-cyclopent-3-en-1-yl | H |
| G14 | 3,3-diMe-cPen | H |
| G15 | 3,4-diF-cPen | H |
| G16 | 3-F-cPen | H |
| G17 | 3,3-diF-cPen | H |
| G18 | 3,4-diF-cyclopent-3-en-1-yl | H |
| G19 | 3-F-cyclopent-3-en-1-yl | H |
| G20 | 3-THP | H |
| G21 | 2-Py | H |
| G22 | 3-Py | H |
| G23 | 4-Py | H |
| G24 | —CH(Et)-(CH₂)₃— | |
| G25 | —CH(Et)-(CH₂)₂— | |
| G26 | —CH₂—C(=CH₂)—(CH₂)₂— | |
| G27 | —CH₂—CH(Me)-(CH₂)₂— | |
| G28 | —CH₂—C(Me)₂-(CH₂)₂— | |
| G29 | —CH₂—CHF—(CH₂)₂ | |
| G30 | —CH₂—CF₂—(CH₂)₂ | |
| G31 | (Et)₂CH— | Cl |
| G32 | cPen | Cl |
| G33 | (Et)₂CH— | CF₃ |
| G34 | cPen | CF₃ |

TABLE 52

| Ex | R¹ | R² |
|---|---|---|
| H1 | FH₂C—CH(Me)- | H |
| H2 | F₂HC—CH(Me)- | H |
| H3 | iPr | H |
| H4 | Et | H |
| H5 | (HO—CH₂)₂CH— | H |
| H6 | 1-Me-3-pyrr | H |
| H7 | 3-THF | H |
| H8 | 2,2-diMe-1,3-dioxan-5-yl | H |
| H9 | 2,2-diEt-1,3-dioxan-5-yl | H |
| H10 | 3,4-diMe-cPen | H |
| H11 | 3-Me-cPen | H |
| H12 | 3,4-diMe-cyclopent-3-en-1-yl | H |
| H13 | 3-Me-cyclopent-3-en-1-yl | H |
| H14 | 3,3-diMe-cPen | H |
| H15 | 3,4-diF-cPen | H |
| H16 | 3-F-cPen | H |
| H17 | 3,3-diF-cPen | H |
| H18 | 3,4-diF-cyclopent-3-en-1-yl | H |
| H19 | 3-F-cyclopent-3-en-1-yl | H |
| H20 | 3-THP | H |
| H21 | 2-Py | H |
| H22 | 3-Py | H |
| H23 | 4-Py | H |
| H24 | —CH(Et)-(CH₂)₃— | |
| H25 | —CH(Et)-(CH₂)₂— | |
| H26 | —CH₂—C(=CH₂)—(CH₂)₂— | |
| H27 | —CH₂—CH(Me)-(CH₂)₂— | |
| H28 | —CH₂—C(Me)₂-(CH₂)₂— | |
| H29 | —CH₂—CHF—(CH₂)₂— | |
| H30 | —CH₂—CF₂—(CH₂)₂— | |
| H31 | (Et)₂CH— | Cl |
| H32 | cPen | Cl |
| H33 | (Et)₂CH— | CF₃ |
| H34 | cPen | CF₃ |

TABLE 53

| Ex | R¹ | R² |
|---|---|---|
| I1 | FH₂C—CH(Me)- | H |
| I2 | F₂HC—CH(Me)- | H |
| I3 | 3,4-diMe-cPen | H |
| I4 | 3-Me-cPen | H |
| I5 | 3,4-diMe-cyclopent-3-en-1-yl | H |
| I6 | 3-Me-cyclopent-3-en-1-yl | H |
| I7 | 3,3-diMe-cPen | H |
| I8 | 2,2-diEt-1,3-dioxan-5-yl | H |
| I9 | 3,4-diF-cPen | H |
| I10 | 3-F-cPen | H |
| I11 | 3,3-diF-cPen | H |
| I12 | 3,4-diF-cyclopent-3-en-1-yl | H |
| I13 | 3-F-cyclopent-3-en-1-yl | H |
| I14 | 3-THP | H |
| I15 | 2-Py | H |
| I16 | 3-Py | H |
| I17 | 4-Py | H |
| I18 | —CH(Et)-(CH₂)₃— | |
| I19 | —CH(Et)-(CH₂)₂— | |
| I20 | —CH₂—C(=CH₂)—(CH₂)₂— | |
| I21 | —CH₂—CH(Me)-(CH₂)₂— | |
| I22 | —CH₂—C(Me)₂-(CH₂)₂— | |
| I23 | —CH₂—CHF—(CH₂)₂— | |
| I24 | —CH₂—CF₂—(CH₂)₂— | |
| I25 | (Et)₂CH— | Cl |
| I26 | cPen | Cl |
| I27 | (Et)₂CH— | CF₃ |
| I28 | cPen | CF₃ |

TABLE 54

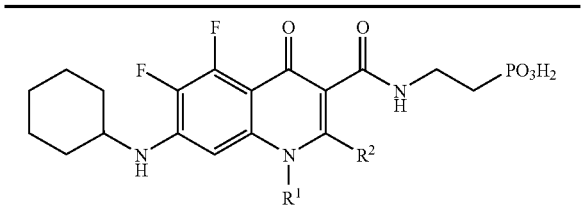

| Ex | R¹ | R² |
|---|---|---|
| J1 | FH₂C—CH(Me)- | H |
| J2 | F₂HC—CH(Me)- | H |
| J3 | iPr | H |
| J4 | Et | H |
| J5 | (HO—CH₂)₂CH— | H |
| J6 | 1-Me-3-pyrr | H |
| J7 | 3-THF | H |
| J8 | 2,2-diMe-1,3-dioxan-5-yl | H |
| J9 | 2,2-diEt-1,3-dioxan-5-yl | H |
| J10 | 3,4-diMe-cPen | H |
| J11 | 3-Me-cPen | H |
| J12 | 3,4-diMe-cyclopent-3-en-1-yl | H |
| J13 | 3-Me-cyclopent-3-en-1-yl | H |
| J14 | 3,3-diMe-cPen | H |
| J15 | 3,4-diF-cPen | H |
| J16 | 3-F-cPen | H |
| J17 | 3,3-diF-cPen | H |
| J18 | 3,4-diF-cyclopent-3-en-1-yl | H |
| J19 | 3-F-cyclopent-3-en-1-yl | H |
| J20 | 3-THP | H |
| J21 | 2-Py | H |
| J22 | 3-Py | H |
| J23 | 4-Py | H |
| J24 | —CH(Et)-(CH₂)₃— | |
| J24 | —CH(Et)-(CH₂)₂— | |
| J25 | —CH₂—C(=CH₂)—(CH₂)₂— | |
| J26 | —CH₂—CH(Me)-(CH₂)₂— | |
| J27 | —CH₂—C(Me)₂-(CH₂)₂— | |
| J28 | —CH₂—CHF—(CH₂)₂— | |
| J29 | —CH₂—CF₂—(CH₂)₂— | |
| J30 | (Et)₂CH— | Cl |
| J31 | cPen | Cl |
| J32 | (Et)₂CH— | CF₃ |
| J33 | cPen | CF₃ |

TABLE 55

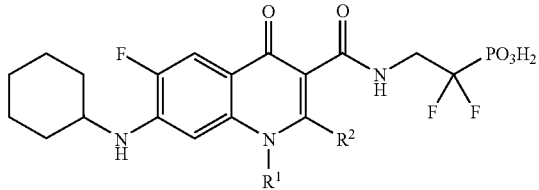

| Ex | R¹ | R² |
|---|---|---|
| K1 | FH₂C—CH(Me)- | H |
| K2 | F₂HC—CH(Me)- | H |
| K3 | iPr | H |
| K4 | Et | H |
| K5 | (HO—CH₂)₂CH— | H |
| K6 | 1-Me-3-pyrr | H |
| K7 | 3-THF | H |
| K8 | 2,2-diMe-1,3-dioxan-5-yl | H |
| K9 | 2,2-diEt-1,3-dioxan-5-yl | H |
| K10 | 3,4-diMe-cPen | H |
| K11 | 3-Me-cPen | H |
| K12 | 3,4-diMe-cyclopent-3-en-1-yl | H |
| K13 | 3-Me-cyclopent-3-en-1-yl | H |
| K14 | 3,3-diMe-cPen | H |
| K15 | 3,4-diF-cPen | H |

TABLE 55-continued

| Ex | R¹ | R² |
|---|---|---|
| K16 | 3-F-cPen | H |
| K17 | 3,3-diF-cPen | H |
| K18 | 3,4-diF-cyclopent-3-en-1-yl | H |
| K19 | 3-F-cyclopent-3-en-1-yl | H |
| K20 | 3-THP | H |
| K21 | 2-Py | H |
| K22 | 3-Py | H |
| K23 | 4-Py | H |
| K24 | —CH(Et)-(CH₂)₃— | |
| K25 | —CH(Et)-(CH₂)₂— | |
| K26 | —CH₂—C(=CH₂)—(CH₂)₂— | |
| K27 | —CH₂—CH(Me)-(CH₂)₂— | |
| K28 | —CH₂—C(Me)₂-(CH₂)₂— | |
| K29 | —CH₂—CHF—(CH₂)₂— | |
| K30 | —CH₂—CF₂—(CH₂)₂— | |
| K31 | (Et)₂CH— | Cl |
| K32 | cPen | Cl |
| K33 | (Et)₂CH— | CF₃ |
| K34 | cPen | CF₃ |

TABLE 56

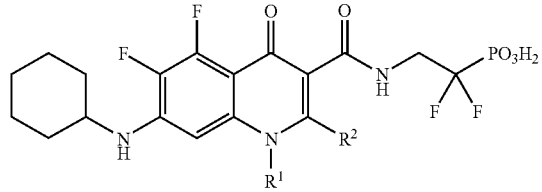

| Ex | R¹ | R² |
|---|---|---|
| L1 | FH₂C—CH(Me)- | H |
| L2 | F₂HC—CH(Me)- | H |
| L3 | iPr | H |
| L4 | Et | H |
| L5 | (HO—CH₂)₂CH— | H |
| L6 | 1-Me-3-pyrr | H |
| L7 | 3-THF | H |
| L8 | 2,2-diMe-1,3-dioxan-5-yl | H |
| L9 | 2,2-diEt-1,3-dioxan-5-yl | H |
| L10 | 3,4-diMe-cPen | H |
| L11 | 3-Me-cPen | H |
| L12 | 3,4-diMe-cyclopent-3-en-1-yl | H |
| L13 | 3-Me-cyclopent-3-en-1-yl | H |
| L14 | 3,3-diMe-cPen | H |
| L15 | 3,4-diF-cPen | H |
| L16 | 3-F-cPen | H |
| L17 | 3,3-diF-cPen | H |
| L18 | 3,4-diF-cyclopent-3-en-1-yl | H |
| L19 | 3-F-cyclopent-3-en-1-yl | H |
| L20 | 3-THP | H |
| L21 | 2-Py | H |
| L22 | 3-Py | H |
| L23 | 4-Py | H |
| L24 | —CH(Et)-(CH₂)₃— | |
| L25 | —CH(Et)-(CH₂)₂— | |
| L26 | —CH₂—C(=CH₂)—(CH₂)₂— | |
| L27 | —CH₂—CH(Me)-(CH₂)₂— | |
| L28 | —CH₂—C(Me)₂-(CH₂)₂— | |
| L29 | —CH₂—CHF—(CH₂)₂— | |
| L30 | —CH₂—CF₂—(CH₂)₂— | |

TABLE 56-continued

[Structure: cyclohexylamino-difluoro-quinolone with N-R¹, R² substituents, and carboxamide-CF₂-PO₃H₂ side chain]

| Ex | R¹ | R² |
|---|---|---|
| L31 | (Et)₂CH— | Cl |
| L32 | cPen | Cl |
| L33 | (Et)₂CH— | CF₃ |
| L34 | cPen | CF₃ |

TABLE 57

[Structure: cyclohexylamino-fluoro-quinolone with R substituent, N-cyclopentyl, and glycine carboxamide]

| Ex | R |
|---|---|
| M1 | Cl |
| M2 | Br |
| M3 | Me |
| M4 | NC— |
| M5 | CF₃ |
| M6 | HO— |
| M7 | H₂N— |
| M8 | 4-mor |
| M9 | 1-pipe |
| M10 | Me₂N— |
| M11 | Et₂N— |
| M12 | AcN(Me)- |
| M13 | AcNH— |

TABLE 58

[Structure: cyclohexylamino-fluoro-quinolone with R substituent, N-(1-ethylpropyl), and glycine carboxamide]

| Ex | R |
|---|---|
| O1 | Cl |
| O2 | Br |
| O3 | Me |
| O4 | NC— |
| O5 | CF₃ |
| O6 | H₂N— |
| O7 | 4-mor |
| O8 | 1-pipe |
| O9 | Et₂N— |

TABLE 58-continued

| Ex | R |
|---|---|
| O10 | AcN(Me)- |
| O11 | AcNH— |

TABLE 59

[Structure: cyclohexylamino-fluoro-quinolone with R substituent, N-cyclopentyl, and glutamic acid carboxamide]

| Ex | R |
|---|---|
| P1 | Cl |
| P2 | Br |
| P3 | Me |
| P4 | NC— |
| P5 | CF₃ |
| P6 | HO— |
| P7 | H₂N— |
| P8 | 4-mor |
| P9 | 1-pipe |
| P10 | Me₂N— |
| P11 | Et₂N— |
| P12 | AcN(Me)- |
| P13 | AcNH— |

TABLE 60

[Structure: cyclohexylamino-fluoro-quinolone with R substituent, N-(1-ethylpropyl), and glutamic acid carboxamide]

| Ex | R |
|---|---|
| Q1 | Cl |
| Q2 | Br |
| Q3 | Me |
| Q4 | NC— |
| Q5 | CF₃ |
| Q6 | HO— |
| Q7 | H₂N— |

TABLE 60-continued

| Ex | R |
|---|---|
| Q8 | 4-mor |
| Q9 | 1-pipe |
| Q10 | Me₂N— |
| Q11 | Et₂N— |
| Q12 | AcN(Me)- |
| Q13 | AcNH— |

TABLE 61

| Ex | R |
|---|---|
| R1 | Cl |
| R2 | Br |
| R3 | Me |
| R4 | NC— |
| R5 | CF₃ |
| R6 | HO— |
| R7 | H₂N— |
| R8 | 4-mor |
| R9 | 1-pipe |
| R10 | Me₂N— |
| R11 | Et₂N— |
| R12 | AcN(Me)- |
| R13 | AcNH— |

TABLE 62

| Ex | R |
|---|---|
| S1 | Cl |
| S2 | Br |
| S3 | Me |
| S4 | NC— |
| S5 | CF₃ |

TABLE 62-continued

| Ex | R |
|---|---|
| S6 | HO— |
| S7 | H₂N— |
| S8 | 4-mor |
| S9 | 1-pipe |
| S10 | Me₂N— |
| S11 | Et₂N— |
| S12 | AcN(Me)- |
| S13 | AcNH— |

TABLE 63

| Ex | R |
|---|---|
| T1 | Cl |
| T2 | Br |
| T3 | Me |
| T4 | NC— |
| T5 | CF₃ |
| T6 | HO— |
| T7 | H₂N— |
| T8 | 4-mor |
| T9 | 1-pipe |
| T10 | Me₂N— |
| T11 | Et₂N— |
| T12 | AcN(Me)- |
| T13 | AcNH— |

TABLE 64

| Ex | R |
|---|---|
| U1 | Cl |
| U2 | Br |
| U3 | Me |

TABLE 64-continued

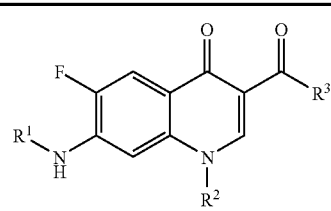

| Ex | R |
|---|---|
| U4 | NC— |
| U5 | $CF_3$ |
| U6 | HO— |
| U7 | $H_2N$— |
| U8 | 4-mor |
| U9 | 1-pipe |
| U10 | $Me_2N$— |
| U11 | $Et_2N$— |
| U12 | AcN(Me)- |
| U13 | AcNH— |

TABLE 65

| Ex | $R^1$ | $R^2$ | $R^3$ |
|---|---|---|---|
| V1 | 4-F-cHex | cPen | $HO_2C$—$CH_2NH$— |
| V2 | 4-F-cHex | cPen | (S)—$HO_2C$—$(CH_2)_2CH(CO_2H)NH$— |
| V3 | 4-F-cHex | cPen | $(HO)_2(O)P$—$(CH_2)_2NH$— |
| V4 | 4-F-cHex | cPen | $(HO)_2(O)P$—$CF_2CH_2NH$— |
| V5 | 4-F-cHex | $(Et)_2CH$— | $HO_2C$—$CH_2NH$— |
| V6 | 4-F-cHex | $(Et)_2CH$— | (S)—$HO_2C$—$(CH_2)_2CH(CO_2H)NH$— |
| V7 | 4-F-cHex | $(Et)_2CH$— | $(HO)_2(O)P$—$(CH_2)_2NH$— |
| V8 | 4-F-cHex | $(Et)_2CH$— | $(HO)_2(O)P$—$CF_2CH_2NH$— |
| V9 | 4,4-diF-cHex | cPen | (S)—$HO_2C$—$(CH_2)_2CH(CO_2H)NH$— |
| V10 | 4,4-diF-cHex | cPen | $(HO)_2(O)P$—$(CH_2)_2NH$— |
| V11 | 4,4-diF-cHex | cPen | $(HO)_2(O)P$—$CF_2CH_2NH$— |
| V12 | 4,4-diF-cHex | $(Et)_2CH$— | $HO_2C$—$CH_2NH$— |
| V13 | 4,4-diF-cHex | $(Et)_2CH$— | (S)—$HO_2C$—$(CH_2)_2CH(CO_2H)NH$— |
| V14 | 4,4-diF-cHex | $(Et)_2CH$— | $(HO)_2(O)P$—$(CH_2)_2NH$— |
| V15 | 4,4-diF-cHex | $(Et)_2CH$— | $(HO)_2(O)P$—$CF_2CH_2NH$— |
| V16 | 3-THP | cPen | (S)—$HO_2C$—$(CH_2)_2CH(CO_2H)NH$— |
| V17 | 3-THP | cPen | $(HO)_2(O)P$—$(CH_2)_2NH$— |
| V18 | 3-THP | cPen | $(HO)_2(O)P$—$CF_2CH_2NH$— |
| V19 | 3-THP | $(Et)_2CH$— | $HO_2C$—$CH_2NH$— |
| V20 | 3-THP | $(Et)_2CH$— | (S)—$HO_2C$—$(CH_2)_2CH(CO_2H)NH$— |
| V21 | 3-THP | $(Et)_2CH$— | $(HO)_2(O)P$—$(CH_2)_2NH$— |
| V22 | 3-THP | $(Et)_2CH$— | $(HO)_2(O)P$—$CF_2CH_2NH$— |

TABLE 66

| Ex | $R^1$ | $R^2$ | $R^3$ |
|---|---|---|---|
| W1 | 4-F-cHex | cPen | $HO_2C$—$CH_2NH$— |
| W2 | 4-F-cHex | cPen | (S)—$HO_2C$—$(CH_2)_2CH(CO_2H)NH$— |
| W3 | 4-F-cHex | cPen | $(HO)_2(O)P$—$(CH_2)_2NH$— |
| W4 | 4-F-cHex | cPen | $(HO)_2(O)P$—$CF_2CH_2NH$— |
| W5 | 4-F-cHex | $(Et)_2CH$— | $HO_2C$—$CH_2NH$— |
| W6 | 4-F-cHex | $(Et)_2CH$— | (S)—$HO_2C$—$(CH_2)_2CH(CO_2H)NH$— |
| W7 | 4-F-cHex | $(Et)_2CH$— | $(HO)_2(O)P$—$(CH_2)_2NH$— |
| W8 | 4-F-cHex | $(Et)_2CH$— | $(HO)_2(O)P$—$CF_2CH_2NH$— |
| W9 | 4,4-diF-cHex | cPen | $HO_2C$—$CH_2NH$— |
| W10 | 4,4-diF-cHex | cPen | (S)—$HO_2C$—$(CH_2)_2CH(CO_2H)NH$— |
| W11 | 4,4-diF-cHex | cPen | $(HO)_2(O)P$—$(CH_2)_2NH$— |
| W12 | 4,4-diF-cHex | cPen | $(HO)_2(O)P$—$CF_2CH_2NH$— |
| W13 | 4,4-diF-cHex | $(Et)_2CH$— | $HO_2C$—$CH_2NH$— |
| W14 | 4,4-diF-cHex | $(Et)_2CH$— | (S)—$HO_2C$—$(CH_2)_2CH(CO_2H)NH$— |
| W15 | 4,4-diF-cHex | $(Et)_2CH$— | $(HO)_2(O)P$—$(CH_2)_2NH$— |
| W16 | 4,4-diF-cHex | $(Et)_2CH$— | $(HO)_2(O)P$—$CF_2CH_2NH$— |
| W17 | 3-THP | cPen | (S)—$HO_2C$—$(CH_2)_2CH(CO_2H)NH$— |
| W18 | 3-THP | cPen | $(HO)_2(O)P$—$(CH_2)_2NH$— |
| W19 | 3-THP | cPen | $(HO)_2(O)P$—$CF_2CH_2NH$— |
| W20 | 3-THP | $(Et)_2CH$— | $HO_2C$—$CH_2NH$— |
| W21 | 3-THP | $(Et)_2CH$— | (S)—$HO_2C$—$(CH_2)_2CH(CO_2H)NH$— |
| W22 | 3-THP | $(Et)_2CH$— | $(HO)_2(O)P$—$(CH_2)_2NH$— |
| W23 | 3-THP | $(Et)_2CH$— | $(HO)_2(O)P$—$CF_2CH_2NH$— |

TABLE 67

| Ex | $R^1$ | $R^2$ | $R^3$ |
|---|---|---|---|
| X1 | H | Et | (S)—$HO_2C$—$(CH_2)_2CH(CO_2H)NH$— |
| X2 | H | Et | $(HO)_2(O)P$—$CF_2CH_2NH$— |
| X3 | H | $(Et)_2CH$— | $(HO)_2(O)P$—$CF_2CH_2NH$— |
| X4 | H | c-Pen | (S)—$HO_2C$—$(CH_2)_2CH(CO_2H)NH$— |
| X5 | H | c-Pen | $(HO)_2(O)P$—$(CH_2)_2NH$— |
| X6 | H | c-Pen | $(HO)_2(O)P$—$CF_2CH_2NH$— |
| X7 | F | Et | $HO_2C$—$CH_2NH$— |
| X8 | F | Et | (S)—$HO_2C$—$(CH_2)_2CH(CO_2H)NH$— |
| X9 | F | Et | $(HO)_2(O)P$—$(CH_2)_2NH$— |
| X10 | F | Et | $(HO)_2(O)P$—$CF_2CH_2NH$— |
| X11 | F | $(Et)_2CH$— | $HO_2C$—$CH_2NH$— |
| X12 | F | $(Et)_2CH$— | (S)—$HO_2C$—$(CH_2)_2CH(CO_2H)NH$— |
| X13 | F | $(Et)_2CH$— | $(HO)_2(O)P$—$(CH_2)_2NH$— |
| X14 | F | $(Et)_2CH$— | $(HO)_2(O)P$—$CF_2CH_2NH$— |
| X15 | F | c-Pen | $HO_2C$—$CH_2NH$— |
| X16 | F | c-Pen | (S)—$HO_2C$—$(CH_2)_2CH(CO_2H)NH$— |
| X17 | F | c-Pen | $(HO)_2(O)P$—$(CH_2)_2NH$— |
| X18 | F | c-Pen | $(HO)_2(O)P$—$CF_2CH_2NH$— |

What is claimed is:

1. A platelet aggregation inhibitor comprising a quinolone derivative represented by the formula (I) or a pharmaceutically acceptable salt thereof as an active ingredient:

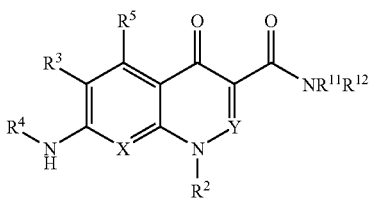

[the symbols in the formula have the following meanings:
X: C—$R^7$ or N;
Y: C—$R^6$ or N;
$R^{11}$: —H;
$R^{12}$: a lower alkyl which is substituted;
$R^2$: a lower alkyl or a cycloalkyl;
$R^3$: a halogen;
$R^4$: a cycloalkyl;
$R^5$: —H;
$R^6$: —H;
$R^7$: —H.

2. A P2Y12 inhibitor comprising the compound according to claim 1 as an active ingredient.

3. A method for inhibiting platelet aggregation in an individual, comprising administering a therapeutically effective amount of the compound of claim 1, and at least one pharmaceutically acceptable carrier, to the individual.

4. A method for inhibiting P2Y12 in an individual needing therapy for circulatory diseases involving thrombosis via platelet aggregation, comprising administering a therapeutically effective amount of the compound of claim 1, and at least one pharmaceutically acceptable carrier, to the individual.

5. A quinolone derivative represented by the formula (I-a) or a pharmaceutically acceptable salt thereof:

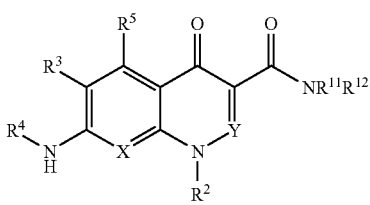

[the symbols in the formula have the following meanings:
X: C—$R^7$ or N;
Y: C—$R^6$ or N;
$R^{11}$: —H;
$R^{12}$: a lower alkyl, which is substituted;
$R^2$: a lower alkyl or a cycloalkyl;
$R^3$: a halogen;
$R^4$: a cycloalkyl;
$R^5$: —H;
$R^6$: —H;
$R^7$: —H.

6. The compound according to claim 5, wherein X is CH.

7. The compound according to claim 6, wherein $R^{12}$ is a lower alkyl substituted with one or more substituent groups selected from Group Q, wherein at least one of the substituent groups is selected from Group P:
Group P: —$CO_2H$, —$SO_3H$, —$P(O)(OH)_2$, and —$OP(O)(OH)_2$; and
Group Q: —F, —OH, —$CO_2H$, —$SO_3H$, —$P(O)(OH)_2$, and —$OP(O)(OH)_2$.

8. The compound according to claim 5, which is
(2S)-2-({[7-(cyclohexylamino)-1-cyclopentyl-6-fluoro-4-oxo-1,4-dihydroquinolin-3-yl]carbonyl}amino)butanedioic acid,
(2S)-2-({[7-(cyclohexylamino)-1-cyclopentyl-6-fluoro-4-oxo-1,4-dihydroquinolin-3-yl]carbonyl}amino)pentanedioic acid,
(2S)-2-({[7-(cyclohexylamino)-1-(1-ethylpropyl)-6-fluoro-4-oxo-1,4-dihydroquinolin-3-yl]carbonyl}amino)pentanedioic acid or
(2S)-2-({[7-(cyclohexylamino)-1-(1-ethylpropyl)-6-fluoro-4-oxo-1,4-dihydrocinnolin-3-yl]carbonyl}amino)pentanedioic acid,
or a pharmaceutically acceptable salt thereof.

9. A pharmaceutical composition comprising a compound according to any one of claims 5, 6, 7 or 8 and a pharmaceutically acceptable carrier.

10. The pharmaceutical composition according to claim 9, which is a platelet aggregation inhibitor.

11. The pharmaceutical composition according to claim 9, which is a P2Y12 inhibitor.

12. A method for inhibiting platelet aggregation in an individual, comprising administering a therapeutically effective amount of the compound of any one of claims 5, 6, 7 or 8, and at least one pharmaceutically acceptable carrier, to the individual.

13. A method for inhibiting P2Y12 in an individual needing therapy for circulatory diseases involving thrombosis via platelet aggregation, comprising administering a therapeutically effective amount of the compound of any one of claims 5, 6, 7 or 8, and at least one pharmaceutically acceptable carrier, to the individual.

14. The compound according to claim 5, which is
[2-({[7-(cyclohexylamino)-1-cyclopentyl-6-fluoro-4-oxo-1,4-dihydroquinolin-3-yl]carbonyl}amino)ethyl] phosphonic acid,
2-({[7-(cyclohexylamino)-1-cyclopentyl-6-fluoro-4-oxo-1,4-dihydroquinolin-3-yl]carbonyl}amino)ethyl dihydrogen phosphate,
[2-({[7-(cyclohexylamino)-1-(1-ethylpropyl)-6-fluoro-4-oxo-1,4-dihydroquinolin-3-yl]carbonyl}amino)-1,1-difluoroethyl]phosphonic acid,
[2-({[7-(cyclohexylamino)-1-ethyl-6-fluoro-4-oxo-1,4-dihydrocinnolin-3-yl]carbonyl}amino)ethyl]phosphonic acid,
[2-({[7-(cyclohexylamino)-1-(1-ethylpropyl)-6-fluoro-4-oxo-1,4-dihydrocinnolin-3-yl]carbonyl}amino)ethyl] phosphonic acid, or
[2-({[7-(cyclohexylamino)-1-(1-ethylpropyl)-6-fluoro-4-oxo-1,4-dihydroquinolin-3-yl]carbonyl}amino)ethyl] phosphonic acid,
or a pharmaceutically acceptable salt thereof.

* * * * *